US012318093B2

(12) United States Patent
Armenteros et al.

(10) Patent No.: US 12,318,093 B2
(45) Date of Patent: *Jun. 3, 2025

(54) POLYMER OVERMOLDED BARIATRIC CLAMP AND METHOD OF INSTALLING

(71) Applicant: Advanced Bariatric Technology, LLC, Coral Gables, FL (US)

(72) Inventors: Jesus R. Armenteros, Santo Domingo (DO); C. Kenneth French, Clifton, TX (US); Moises Jacobs, Miami, FL (US)

(73) Assignee: Advanced Bariatric Technology, LLC, Coral Gables, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/739,672

(22) Filed: Jun. 11, 2024

(65) Prior Publication Data

US 2024/0325027 A1      Oct. 3, 2024

Related U.S. Application Data

(63) Continuation of application No. 17/403,645, filed on Aug. 16, 2021, now Pat. No. 12,023,039, which is a
(Continued)

(51) Int. Cl.
*A61B 17/122*      (2006.01)
*A61B 17/064*      (2006.01)
(Continued)

(52) U.S. Cl.
CPC ........ *A61B 17/122* (2013.01); *A61B 17/0643* (2013.01); *A61B 17/128* (2013.01);
(Continued)

(58) Field of Classification Search
CPC .............. A61B 17/122; A61B 17/1227; A61B 17/1285; A61B 17/128; A61B 17/1225;
(Continued)

(56) References Cited

U.S. PATENT DOCUMENTS 350,850 A    10/1886  Tatum
422,906 A     3/1890  Booth
(Continued)

FOREIGN PATENT DOCUMENTS

AU          201399422         2/2017
AU       2018247195 A1       11/2018
(Continued)

OTHER PUBLICATIONS

"A Pathway to Endoscopic Bariatric Therapies" Gastrointestinal Endoscopy Journal, www.giejournal.org, vol. 74, No. 5 (2011), pp. 943-953.
(Continued)

*Primary Examiner* — Majid Jamialahmadi
(74) *Attorney, Agent, or Firm* — Foley & Lardner LLP

(57) ABSTRACT

A bariatric clamp including a partition-forming section including first and second elongated members separated by a first distance; and a passage-forming section including a bight portion. The bight portion includes a first bend section and a second bend section each having a member extending away from the axis of the clamp; and third and fourth members separated by a second distance; and a flexible hinge joining the third and fourth members. When the bariatric clamp is in the closed position, the second distance is greater than the first distance. The flexible hinge may be stretchable to accommodate different stomach thicknesses.

12 Claims, 68 Drawing Sheets

Related U.S. Application Data continuation of application No. 16/664,447, filed on Oct. 25, 2019, now Pat. No. 11,317,924, which is a continuation of application No. 13/963,998, filed on Aug. 9, 2013, now Pat. No. 10,456,141.

(60) Provisional application No. 61/798,128, filed on Mar. 15, 2013, provisional application No. 61/681,601, filed on Aug. 9, 2012.

(51) Int. Cl.

| | | |
|---|---|---|
| *A61B 17/128* | (2006.01) | |
| *A61B 17/00* | (2006.01) | |
| *A61B 17/04* | (2006.01) | |
| *A61B 17/29* | (2006.01) | |

(52) U.S. Cl.
CPC ..... *A61B 17/1285* (2013.01); *A61B 2017/00336* (2013.01); *A61B 2017/00424* (2013.01); *A61B 2017/00477* (2013.01); *A61B 2017/00818* (2013.01); *A61B 2017/00876* (2013.01); *A61B 17/0482* (2013.01); *A61B 2017/2927* (2013.01)

(58) Field of Classification Search
CPC ... A61B 17/1222; A61B 17/10; A61B 17/068; A61B 17/0682
See application file for complete search history.

(56) References Cited

U.S. PATENT DOCUMENTS

| | | |
|---|---|---|
| 600,887 A | 3/1898 | Pettit |
| 758,449 A | 4/1904 | Jeralds |
| 823,068 A | 6/1906 | Mosley |
| 860,344 A | 7/1907 | Towne |
| 1,190,039 A | 7/1916 | Tatum |
| 1,211,718 A | 1/1917 | Kuehner |
| 1,213,504 A | 1/1917 | Kuehner |
| 1,275,898 A | 8/1918 | Frey |
| 1,297,456 A | 3/1919 | Frey |
| 2,519,909 A | 8/1950 | Johnson |
| 3,247,852 A | 4/1966 | Schneider |
| 3,254,651 A | 6/1966 | Collito |
| 3,316,914 A | 5/1967 | Collito |
| 3,417,752 A | 12/1968 | Butler |
| 3,766,925 A | 10/1973 | Rubricius |
| 3,822,052 A | 7/1974 | Lange |
| 4,060,089 A | 11/1977 | Noiles |
| 4,274,415 A | 6/1981 | Kanamoto et al. |
| 4,346,869 A | 8/1982 | MacNeill |
| 4,390,019 A | 6/1983 | LeVeen et al. |
| 4,414,721 A | 11/1983 | Hufnagel |
| 4,428,374 A | 1/1984 | Auburn |
| 4,453,295 A | 6/1984 | Laszczower |
| 4,457,756 A | 7/1984 | Kern et al. |
| 4,458,681 A | 7/1984 | Hopkins |
| 4,548,202 A | 10/1985 | Duncan |
| 4,556,060 A | 12/1985 | Perlin |
| 4,558,699 A | 12/1985 | Bashour |
| 4,588,160 A | 5/1986 | Flynn et al. |
| 4,589,626 A | 5/1986 | Kurtz et al. |
| 4,610,250 A | 9/1986 | Green |
| 4,673,161 A | 6/1987 | Flynn et al. |
| 4,803,985 A | 2/1989 | Hill |
| 4,834,096 A | 5/1989 | Oh et al. |
| 4,950,284 A | 8/1990 | Green et al. |
| 4,976,721 A | 12/1990 | Blasnik et al. |
| 5,062,846 A | 11/1991 | Oh et al. |
| 5,074,868 A | 12/1991 | Kuzmak |
| 5,127,915 A | 7/1992 | Mattson |
| 5,147,378 A | 9/1992 | Markham |
| 5,156,609 A | 10/1992 | Nakao et al. |
| 5,163,945 A | 11/1992 | Ortiz et al. |
| 5,226,429 A | 7/1993 | Kuzmak |
| 5,234,454 A | 8/1993 | Bangs |
| 5,236,437 A | 8/1993 | Wilk et al. |
| 5,250,058 A | 10/1993 | Miller et al. |
| 5,327,914 A | 7/1994 | Shlain |
| 5,345,949 A | 9/1994 | Shlain |
| 5,423,831 A | 6/1995 | Nates |
| 5,428,871 A | 7/1995 | Iosif |
| 5,456,714 A | 10/1995 | Owen |
| 5,464,416 A | 11/1995 | Steckel |
| 5,549,621 A | 8/1996 | Bessler et al. |
| 5,575,802 A | 11/1996 | McQuilkin et al. |
| 5,609,181 A | 3/1997 | Evans |
| 5,674,231 A | 10/1997 | Green et al. |
| 5,766,189 A | 6/1998 | Matsuno |
| 5,901,993 A | 5/1999 | Lowery et al. |
| 6,015,417 A | 1/2000 | Reynolds, Jr. |
| 6,036,704 A | 3/2000 | Yoon |
| 6,089,527 A | 7/2000 | Utterberg |
| 6,102,922 A | 8/2000 | Jakobsson et al. |
| 6,161,812 A | 12/2000 | Guala et al. |
| 6,179,850 B1 | 1/2001 | Goradia |
| 6,273,903 B1 | 8/2001 | Wilk |
| 6,454,700 B1 | 9/2002 | Forsell |
| 6,464,710 B1 | 10/2002 | Foster |
| 6,503,258 B1 | 1/2003 | Filho |
| 6,537,289 B1 | 3/2003 | Kayan et al. |
| 6,572,629 B2 | 6/2003 | Kalloo et al. |
| 6,694,982 B2 | 2/2004 | Latour |
| 6,716,226 B2 | 4/2004 | Sixto, Jr. et al. |
| 6,814,742 B2 | 11/2004 | Kimura et al. |
| 6,869,438 B2 | 3/2005 | Chao |
| 6,926,724 B1 | 8/2005 | Chu |
| 6,981,978 B2 | 1/2006 | Gannoe |
| 7,022,126 B2 | 4/2006 | De Canniere |
| 7,105,000 B2 | 9/2006 | McBrayer |
| 7,135,032 B2 | 11/2006 | Åkerfeldt |
| 7,214,233 B2 | 5/2007 | Gannoe et al. |
| 7,223,229 B2 | 5/2007 | Inman et al. |
| 7,232,445 B2 | 6/2007 | Kortenbach et al. |
| 7,234,677 B2 | 6/2007 | Zerfas |
| 7,261,725 B2 | 8/2007 | Binmoeller |
| 7,288,100 B2 | 10/2007 | Molina Trigueros |
| 7,320,701 B2 | 1/2008 | Haut et al. |
| 7,338,503 B2 | 3/2008 | Rosenberg et al. |
| 7,416,528 B2 | 8/2008 | Crawford et al. |
| 7,645,285 B2 | 1/2010 | Cosgrove et al. |
| 7,691,053 B2 | 4/2010 | Viola |
| 7,758,493 B2 | 7/2010 | Gingras |
| 7,871,416 B2 | 1/2011 | Phillips |
| 7,892,244 B2 | 2/2011 | Monassevitch et al. |
| 8,287,559 B2 | 10/2012 | Barker et al. |
| 8,382,775 B1 | 2/2013 | Bender et al. |
| 8,529,585 B2 | 9/2013 | Jacobs et al. |
| 8,920,305 B2 | 12/2014 | Jacobs et al. |
| 9,808,257 B2 | 11/2017 | Armenteros et al. |
| 9,814,614 B2 | 11/2017 | Jacobs et al. |
| 10,369,036 B2 | 8/2019 | Jacobs et al. |
| 10,390,943 B2 | 8/2019 | Hernandez |
| 10,420,664 B2 | 9/2019 | Armenteros et al. |
| 10,456,141 B2 | 10/2019 | Armenteros et al. |
| 10,932,938 B2 | 3/2021 | French |
| 2001/0034536 A1 | 10/2001 | Looper et al. |
| 2002/0022844 A1* | 2/2002 | Vom Berg ........... A61B 17/688 606/71 |
| 2002/0022851 A1 | 2/2002 | Kalloo et al. |
| 2002/0055757 A1 | 5/2002 | Torre et al. |
| 2002/0082625 A1 | 6/2002 | Huxel et al. |
| 2002/0138086 A1 | 9/2002 | Sixto et al. |
| 2004/0010271 A1 | 1/2004 | Kortenbach |
| 2004/0059289 A1 | 3/2004 | Garza Alvarez |
| 2004/0082963 A1 | 4/2004 | Gannoe et al. |
| 2004/0092887 A1 | 5/2004 | Nickels |
| 2004/0097989 A1 | 5/2004 | Molina Trigueros |
| 2004/0116945 A1 | 6/2004 | Sharkawy et al. |
| 2004/0147942 A1 | 7/2004 | Chao |
| 2005/0075652 A1 | 4/2005 | Byrum et al. |
| 2005/0119674 A1 | 6/2005 | Gingras |
| 2005/0125014 A1 | 6/2005 | Duluco et al. |
| 2005/0149069 A1 | 7/2005 | Bertolero et al. |

(56) References Cited

U.S. PATENT DOCUMENTS

| | | |
|---|---|---|
| 2005/0192599 A1 | 9/2005 | Demarais |
| 2005/0197714 A1 | 9/2005 | Sayet |
| 2005/0216042 A1 | 9/2005 | Gertner |
| 2005/0250980 A1 | 11/2005 | Swanstrom et al. |
| 2005/0251158 A1 | 11/2005 | Saadat et al. |
| 2005/0277959 A1 | 12/2005 | Cosgrove et al. |
| 2006/0011699 A1 | 1/2006 | Olson et al. |
| 2006/0074440 A1 | 4/2006 | Garner |
| 2006/0157067 A1 | 7/2006 | Saadat et al. |
| 2006/0178564 A1 | 8/2006 | Jones et al. |
| 2006/0200179 A1 | 9/2006 | Barker et al. |
| 2006/0217757 A1 | 9/2006 | Horndeski |
| 2006/0235468 A1 | 10/2006 | Huitema et al. |
| 2006/0241653 A1 | 10/2006 | Jones et al. |
| 2006/0252983 A1 | 11/2006 | Lembo et al. |
| 2006/0264981 A1 | 11/2006 | Viola |
| 2006/0264982 A1 | 11/2006 | Viola et al. |
| 2006/0264987 A1 | 11/2006 | Sgro |
| 2007/0016231 A1 | 1/2007 | Jambor et al. |
| 2007/0021761 A1 | 1/2007 | Phillips |
| 2007/0032807 A1 | 2/2007 | Ortiz et al. |
| 2007/0088190 A1 | 4/2007 | Appel |
| 2007/0088191 A1 | 4/2007 | Appel |
| 2007/0149989 A1 | 6/2007 | Santilli et al. |
| 2007/0167962 A1 | 7/2007 | Gannoe et al. |
| 2007/0185373 A1 | 8/2007 | Tsonton |
| 2007/0213747 A1 | 9/2007 | Monassevitch et al. |
| 2007/0233005 A1 | 10/2007 | McMichael et al. |
| 2007/0250090 A1 | 10/2007 | Makower et al. |
| 2007/0265644 A1 | 11/2007 | Ichihara et al. |
| 2007/0282356 A1 | 12/2007 | Sonnenschein et al. |
| 2008/0033457 A1 | 2/2008 | Francischelli et al. |
| 2008/0039879 A1 | 2/2008 | Chin et al. |
| 2008/0082114 A1 | 4/2008 | McKenna et al. |
| 2008/0092910 A1 | 4/2008 | Brooks |
| 2008/0177292 A1 | 7/2008 | Jacobs et al. |
| 2008/0208324 A1 | 8/2008 | Glithero et al. |
| 2008/0269788 A1 | 10/2008 | Phillips |
| 2008/0275480 A1 | 11/2008 | Jacobs et al. |
| 2008/0287975 A1 | 11/2008 | Weaner et al. |
| 2008/0287976 A1 | 11/2008 | Weaner et al. |
| 2008/0294178 A1 | 11/2008 | Kortenbach et al. |
| 2008/0312670 A1 | 12/2008 | Sampica et al. |
| 2008/0319435 A1 | 12/2008 | Rioux et al. |
| 2009/0012542 A1 | 1/2009 | N'diaye et al. |
| 2009/0088783 A1 | 4/2009 | Kennedy et al. |
| 2009/0137870 A1 | 5/2009 | Bakos et al. |
| 2009/0138009 A1 | 5/2009 | Viswanathan et al. |
| 2009/0198266 A1 | 8/2009 | Cesare |
| 2009/0240105 A1 | 9/2009 | Smit et al. |
| 2009/0281377 A1 | 11/2009 | Newell et al. |
| 2009/0292163 A1 | 11/2009 | Kassab et al. |
| 2010/0010511 A1 | 1/2010 | Harris et al. |
| 2010/0030017 A1 | 2/2010 | Baker et al. |
| 2010/0082050 A1 | 4/2010 | Kassab et al. |
| 2010/0096570 A1 | 4/2010 | Kashmirian et al. |
| 2010/0168768 A1 | 7/2010 | Sonnenschein et al. |
| 2010/0174295 A1 | 7/2010 | Kassab et al. |
| 2010/0249510 A1 | 9/2010 | Yamada |
| 2010/0268161 A1 | 10/2010 | Traversaz |
| 2010/0274268 A1 | 10/2010 | Singh et al. |
| 2010/0312050 A1 | 12/2010 | Forsell |
| 2011/0046641 A1 | 2/2011 | Kassab et al. |
| 2011/0092993 A1 | 4/2011 | Jacobs |
| 2011/0092998 A1 | 4/2011 | Hirszowicz et al. |
| 2011/0093007 A1 | 4/2011 | Abbott et al. |
| 2011/0098732 A1 | 4/2011 | Jacobs |
| 2011/0112434 A1 | 5/2011 | Ghabrial et al. |
| 2011/0172767 A1 | 7/2011 | Rathi et al. |
| 2011/0190791 A1 | 8/2011 | Jacobs et al. |
| 2011/0245593 A1 | 10/2011 | Kassab et al. |
| 2011/0270016 A1 | 11/2011 | Snow et al. |
| 2012/0095484 A1 | 4/2012 | Dominguez |
| 2012/0123463 A1 | 5/2012 | Jacobs |
| 2012/0215061 A1 | 8/2012 | Fridez et al. |
| 2013/0261382 A1 | 10/2013 | Acosta |
| 2014/0012293 A1 | 1/2014 | Bertolero et al. |
| 2014/0046345 A1 | 2/2014 | Armenteros et al. |
| 2014/0074131 A1 | 3/2014 | Armenteros et al. |
| 2014/0200598 A1 | 7/2014 | Kassab et al. |
| 2014/0350664 A1 | 11/2014 | Tozzi et al. |
| 2015/0038794 A1 | 2/2015 | Pattison et al. |
| 2015/0051624 A1 | 2/2015 | Jacobs et al. |
| 2015/0150595 A1 | 6/2015 | Pattison et al. |
| 2016/0058594 A1 | 3/2016 | Armenteros et al. |
| 2017/0258619 A1 | 9/2017 | Jacobs et al. |
| 2017/0360447 A1 | 12/2017 | Armenteros et al. |
| 2018/0008447 A1 | 1/2018 | Jacobs et al. |
| 2019/0021892 A1 | 1/2019 | French |
| 2019/0358067 A1 | 11/2019 | Jacobs et al. |
| 2019/0358068 A1 | 11/2019 | Armenteros et al. |
| 2020/0054340 A1 | 2/2020 | Armenteros et al. |
| 2021/0177633 A1 | 6/2021 | French |
| 2021/0369281 A1 | 12/2021 | Armenteros et al. |

FOREIGN PATENT DOCUMENTS

| | | |
|---|---|---|
| AU | 2017200911 | 12/2018 |
| AU | 2015306617 | 2/2020 |
| CA | 2880155 | 2/2014 |
| CN | 1652725 A | 8/2005 |
| CN | 1923148 A | 8/2006 |
| CN | 1895186 A | 1/2007 |
| CN | 101011272 A | 8/2007 |
| CN | 202027648 U | 4/2011 |
| CN | 102415910 A | 4/2012 |
| CN | 105007838 | 10/2015 |
| CN | 107072660 | 8/2017 |
| CN | 109316221 A | 2/2019 |
| CN | 109805978 A | 5/2019 |
| CO | 30415 | 12/2016 |
| DE | 19751733 | 12/1998 |
| DE | 29822558 | 2/1999 |
| EP | 0 201 344 | 11/1986 |
| EP | 0 220 643 | 5/1987 |
| EP | 1 397 998 | 3/2004 |
| EP | 1 547 529 | 6/2005 |
| EP | 1 600 108 | 11/2005 |
| EP | 1 749 506 | 2/2007 |
| EP | 1 806 101 | 7/2007 |
| EP | 1 882 451 | 1/2008 |
| EP | 2 528 512 B1 | 12/2012 |
| EP | 3 185 784 | 7/2017 |
| EP | 3 398 538 | 11/2018 |
| EP | 2 882 354 B2 | 9/2020 |
| EP | 3 777 719 A1 | 2/2021 |
| JP | 9289989 | 11/1997 |
| JP | 2002085414 | 3/2002 |
| JP | 3425417 B2 | 7/2003 |
| JP | 2007044517 | 2/2007 |
| JP | 2007097664 | 4/2007 |
| JP | 2007159794 | 6/2007 |
| MX | 371177 | 1/2020 |
| NZ | 704680 | 5/2017 |
| RU | 2213529 C2 | 10/2003 |
| RU | 2262896 C2 | 10/2005 |
| RU | 2386455 | 4/2010 |
| RU | 2626875 | 8/2017 |
| RU | 2703508 A | 10/2019 |
| RU | 2019131501 A | 11/2019 |
| RU | 2742019 C2 | 2/2021 |
| SA | 6733 B | 12/2019 |
| TH | 158414 | 12/2016 |
| TH | 174586 | 3/2018 |
| WO | WO-80/01752 A1 | 9/1980 |
| WO | WO-1998/033437 | 8/1998 |
| WO | WO-1999/011179 | 3/1999 |
| WO | WO-00/76432 | 12/2000 |
| WO | WO-00/78234 | 12/2000 |
| WO | WO-2000/078234 | 12/2000 |
| WO | WO-02/064041 | 8/2002 |
| WO | WO-2004017839 | 3/2004 |
| WO | WO-2005/046453 A2 | 5/2005 |
| WO | WO-2006/033385 | 3/2006 |

(56) References Cited

FOREIGN PATENT DOCUMENTS

| WO | WO-2006/044640 | 4/2006 |
|---|---|---|
| WO | WO-2007/009099 A2 | 1/2007 |
| WO | WO-2007013995 | 2/2007 |
| WO | WO-2008081436 | 7/2008 |
| WO | WO-2008091537 | 7/2008 |
| WO | WO-2008101048 | 8/2008 |
| WO | WO-2008/147582 A2 | 12/2008 |
| WO | WO-2011/094700 | 8/2011 |
| WO | WO-2014/026170 | 2/2014 |
| WO | WO-2016/033221 | 3/2016 |
| WO | WO-2018/009669 | 1/2018 |
| WO | WO-2019/023279 A1 | 1/2019 |

OTHER PUBLICATIONS

An espace English abstract of DE-19751733 (Dec. 10, 1998).
An espace English abstract of JP-2007097664-A (Apr. 19, 2007).
An espace English abstract of JP-2007159794-A (Jun. 28, 2007).
An espace English abstract of JP-9289989-A (Nov. 11, 1997).
Certificate of Grant of copending Singapore Application No. SG11201500782R, dated Jun. 15, 2017.
Copending U.S. Appl. No. 62/042,117, filed Aug. 26, 2014; first named inventor: Jesús R. Armenteros.
Copending U.S. Appl. No. 62/118,455, filed Feb. 19, 2015; first named inventor: Jesús R. Armenteros.
Copending U.S. Appl. No. 62/536,364, filed Jul. 24, 2017; first named inventor: C. Kenneth French.
Copending U.S. Appl. No. 62/359,529, filed Jul. 7, 2016; first named inventor: Jesús R. Armenteros.
freedictionary.com definition of "stretchable", accessed on Aug. 2, 2017, http://www.thefreedictionary.com/stretchable.
Geoffrey W.J. Vertical Ligated Gastroplasty by Clamp, Cut and Suture: A Series of 504 Cases Dating Back to 1977.0bes Surg. Nov. 1994;4(4):344-348, PMID: 10742799 [PubMed—as supplied by publisher], 5 pgs.
Helmut Kapczynski, Surgical Instruments 101, An Introduction to Kmedic Certified Instruments, Kmedic, Inc., 1997, Northvale, New Jersey (181 Pages).
International Pat. Appl. No. PCT/US2018/043562, International Preliminary Report on Patentability dated Jan. 28, 2020, 9 pgs.
International Preliminary Report on Patentability cited in PCT/US2008/000644, dated Nov. 17, 2009 (4 pgs).
International Preliminary Report on Patentability cited in PCT/US2011/023205, dated Jul. 31, 2012 (10 pgs).
International Preliminary Report on Patentability cited in PCT/US2013/054435, dated Jun. 9, 2015 (9 pgs).
International Preliminary Report on Patentability of PCT/US2015/047005, mailed Mar. 9, 2017.
International Search Report and Written Opinion of PCT/US17/40908, Sep. 11, 2017.
International Search Report and Written Opinion of PCT/US18/43562, Nov. 21, 2018, 17 pgs.
International Search Report and Written Opinion of PCT/US2015/047005, Nov. 27, 2015.
International Search Report cited in PCT/US2013/54435, dated Jan. 16, 2014 (2 pgs).
International Search Report mailed Nov. 27, 2015 in corresponding PCT Appln. PCT/US2015/047005, 13 pages.
Jacobs, Moises, et al., Presentation, "A Novel Procedure for Bariatric and Metabolic Surgery, a weight loss clamp" Apr. 2015 (20 pgs).
Machine Translation of DE29822558 U1.
Patent Abstract of Japan of JP-2002085414-A (Mar. 26, 2002).
Patent Abstract of Japan of JP-2007044517-A (Feb. 22, 2007).
PCT International Patent Application No. PCT/US2017/040908, International Preliminary Report on Patentability and Notification dated Jan. 17, 2019, 9 pgs.
PCT International Search Report and Written Opinion cited in Patent Application No. PCT/US2011/023205, dated Apr. 5, 2011 (13 pgs).
PCT International Search Report cited in Patent Application No. PCT/US2008/000644, dated Jul. 1, 2008 (1 pg).
Publication of Co-Pending Singapore Patent Application No. 10201704073T, Jun. 29, 2017, 1 pg.
Shalimov, et al., Intestinal Track Surgery, Kiev, "Dzorovya", 1987, c. 558, 2 pgs.
Written Opinion cited in PCT/US2008/000644, dated Jul. 7, 2008 (3 pgs).
Written Opinion cited in PCT/US2013/54435 dated Jan. 16, 2014 (8 pgs).
Written Opinion Dated Apr. 17, 2018 in Singapore Pat. App. No. 11201701503Y, 8 pgs.
Written Opinion of copending Singapore Application No. SG11201500782R, dated Oct. 12, 2015.

* cited by examiner

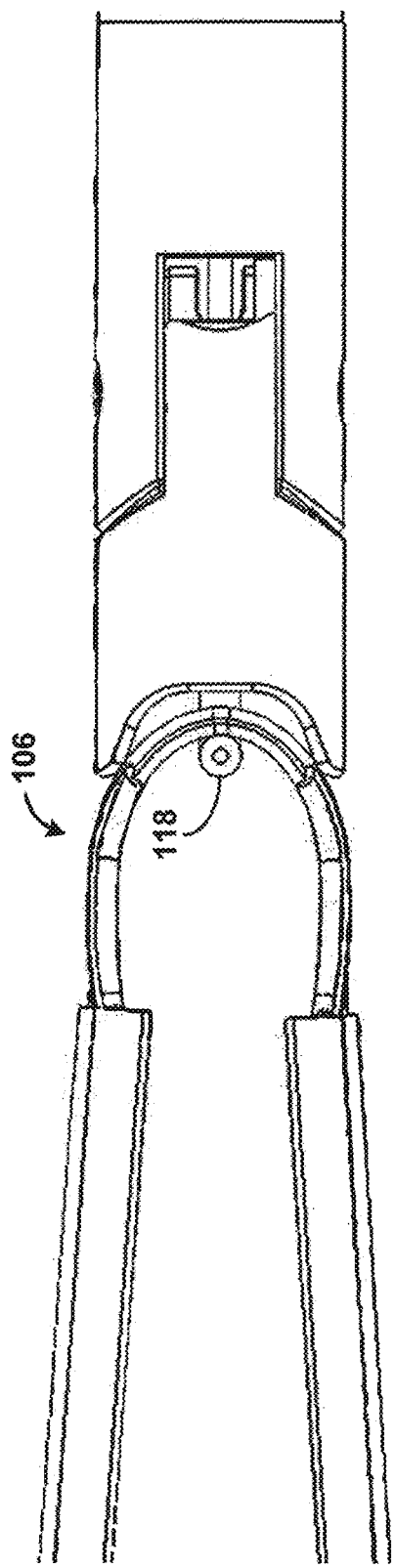
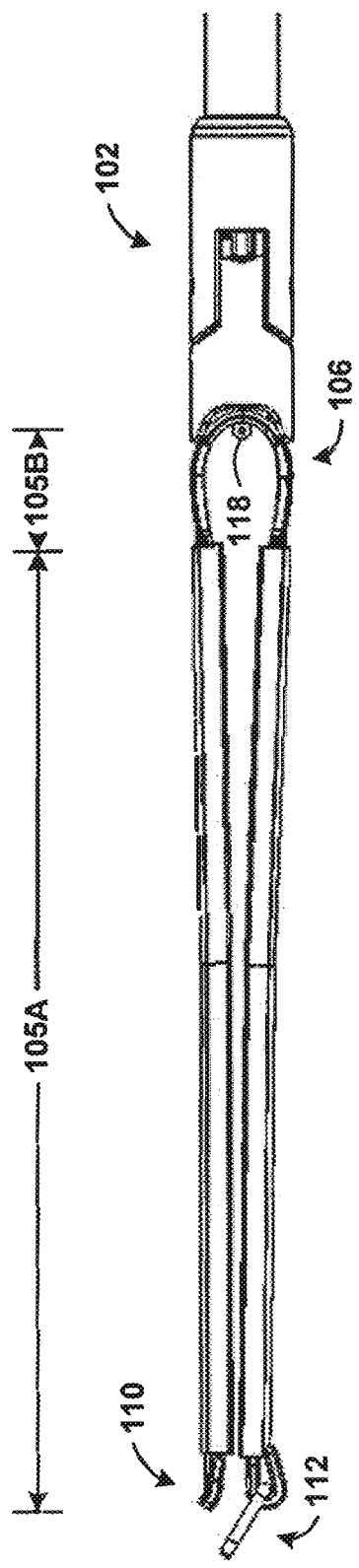
Figure - 2(d)
Figure - 2(e)

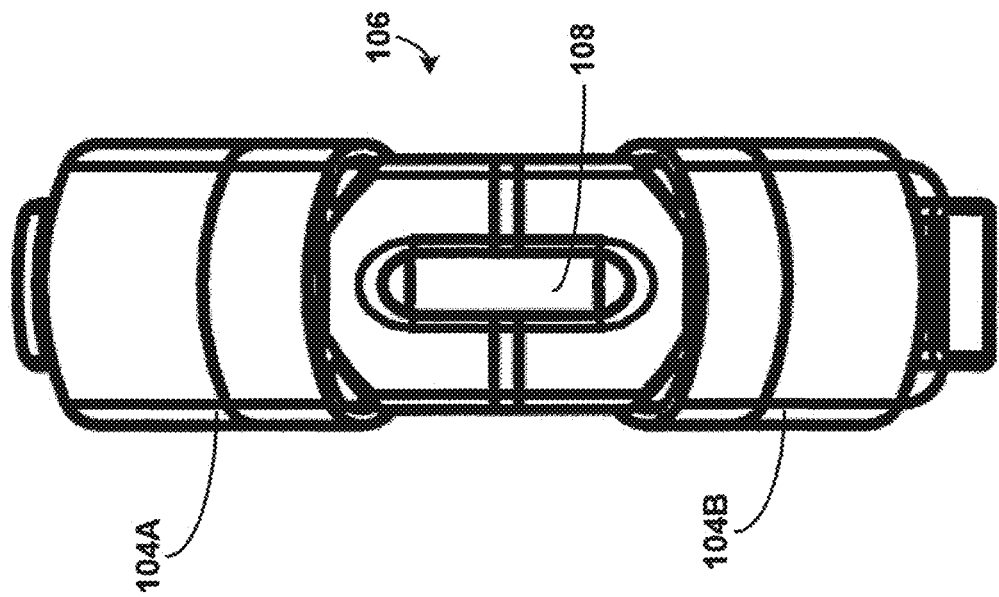
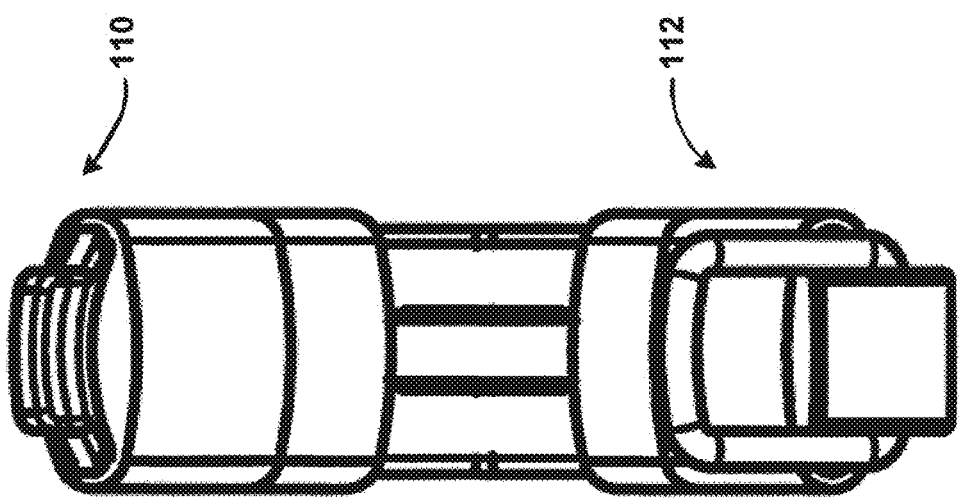

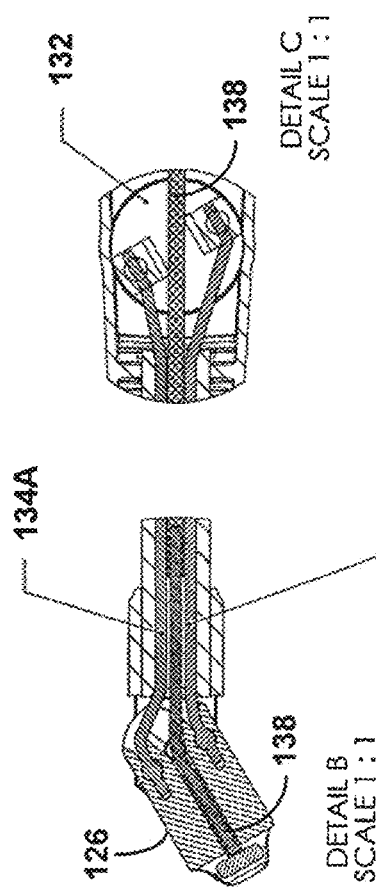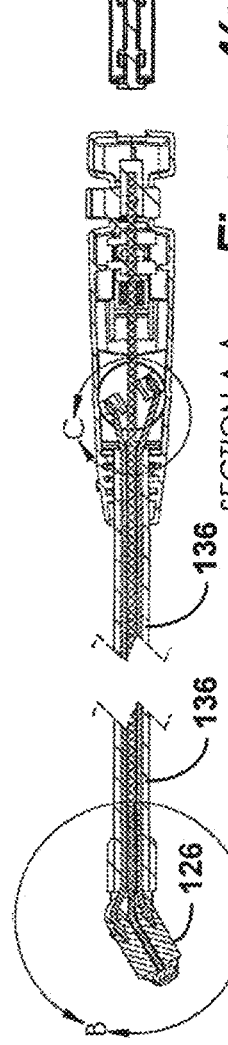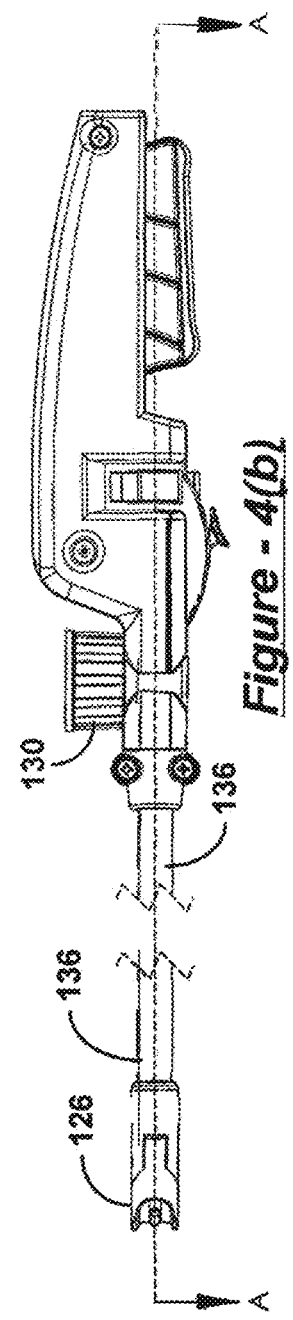

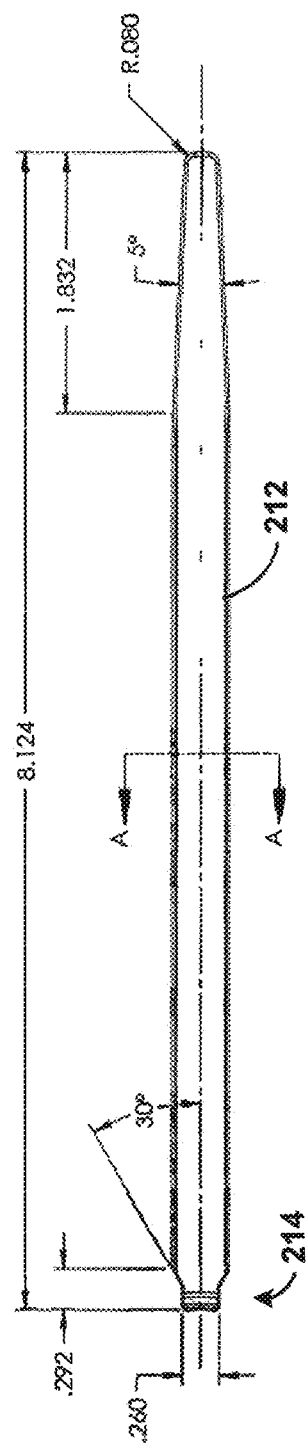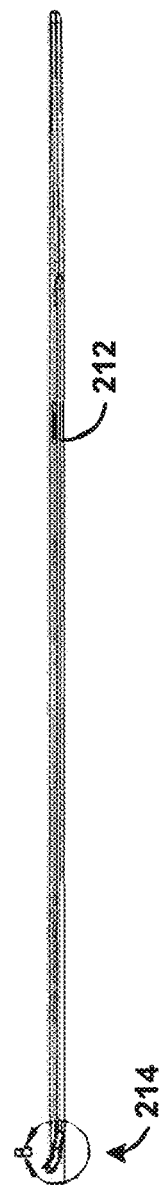
Figure – 6A
Figure – 6B

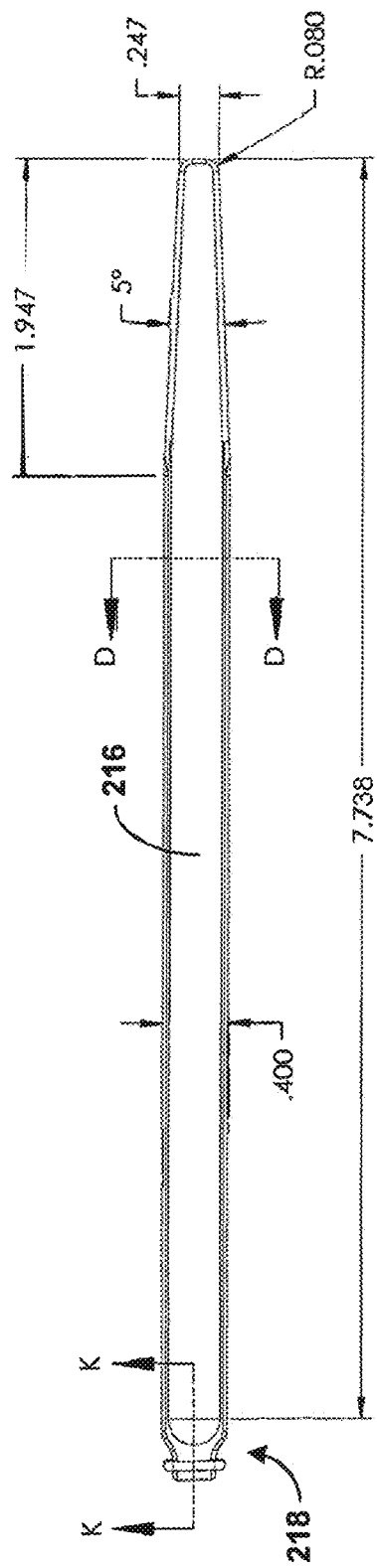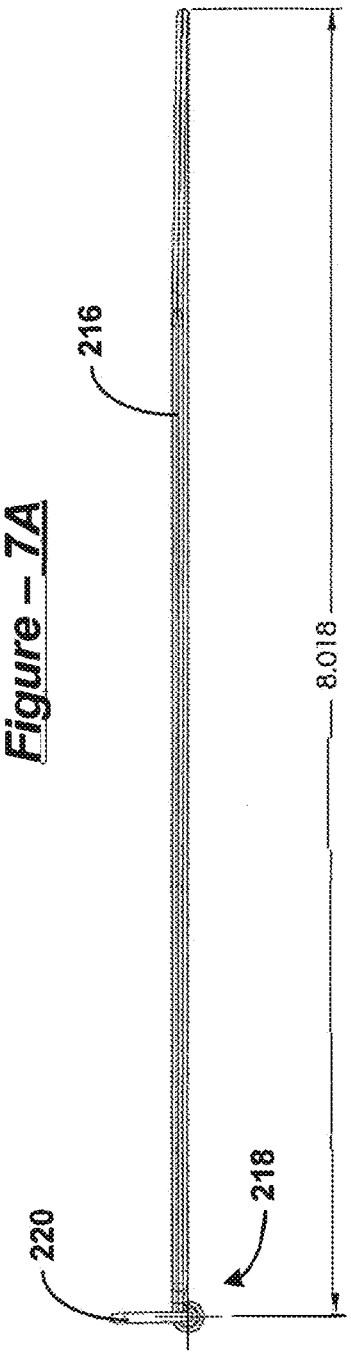
Figure – 7A
Figure – 7B

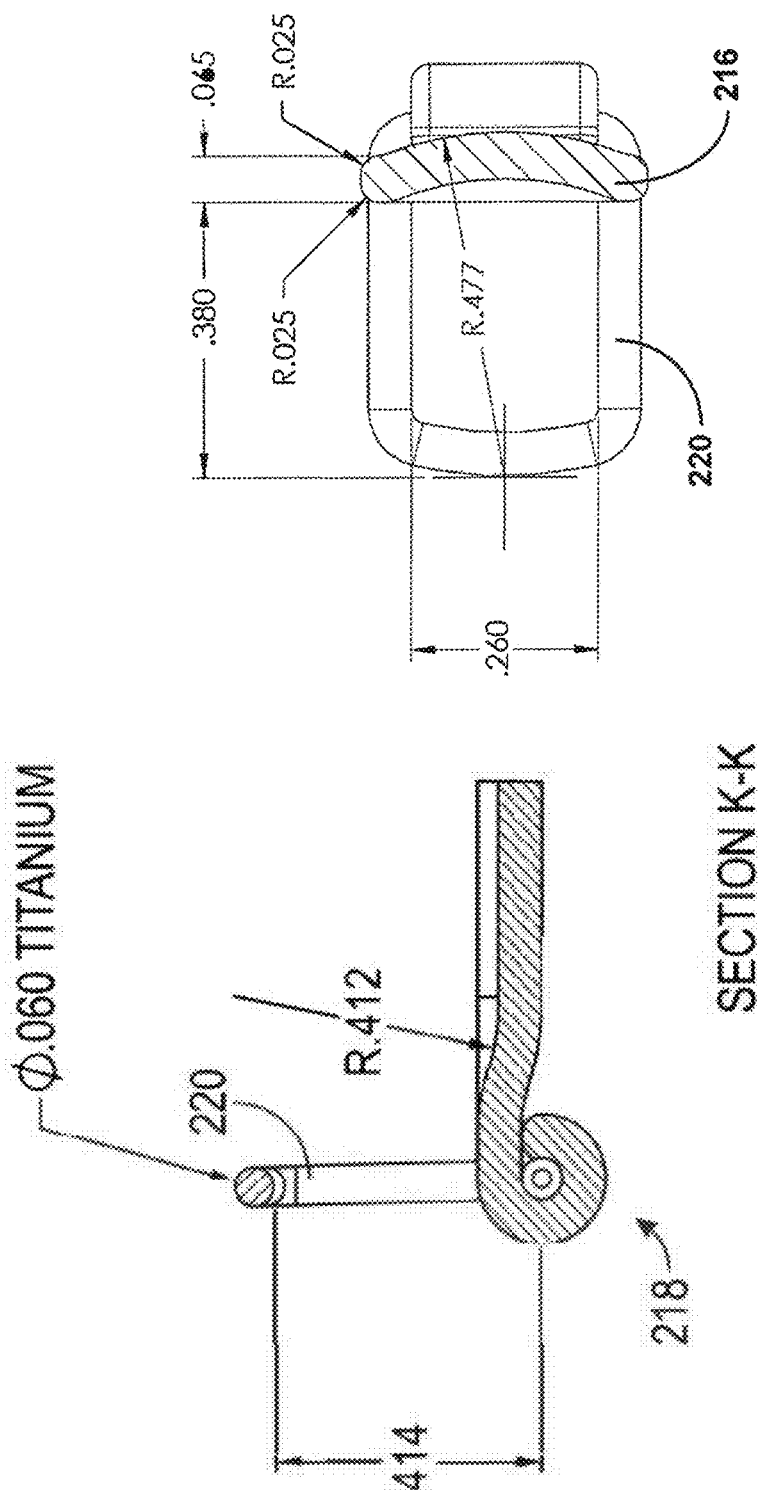

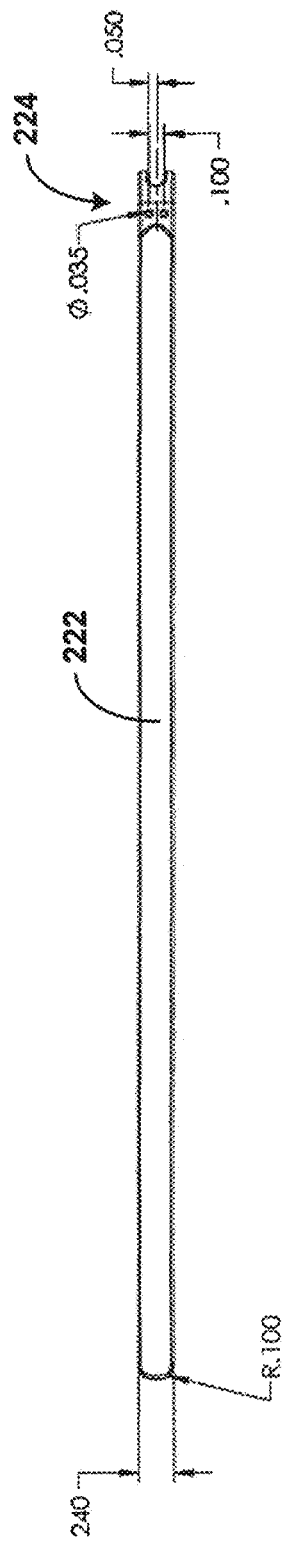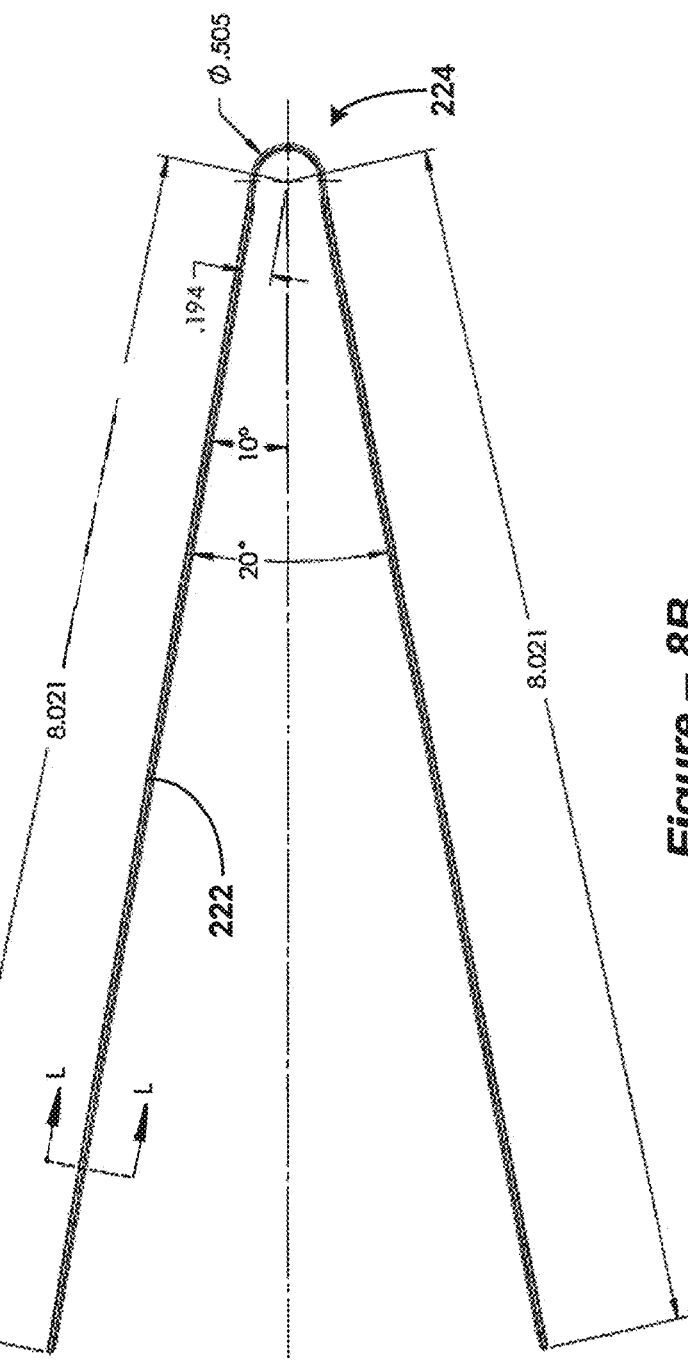
*Figure – 8A*
*Figure – 8B*

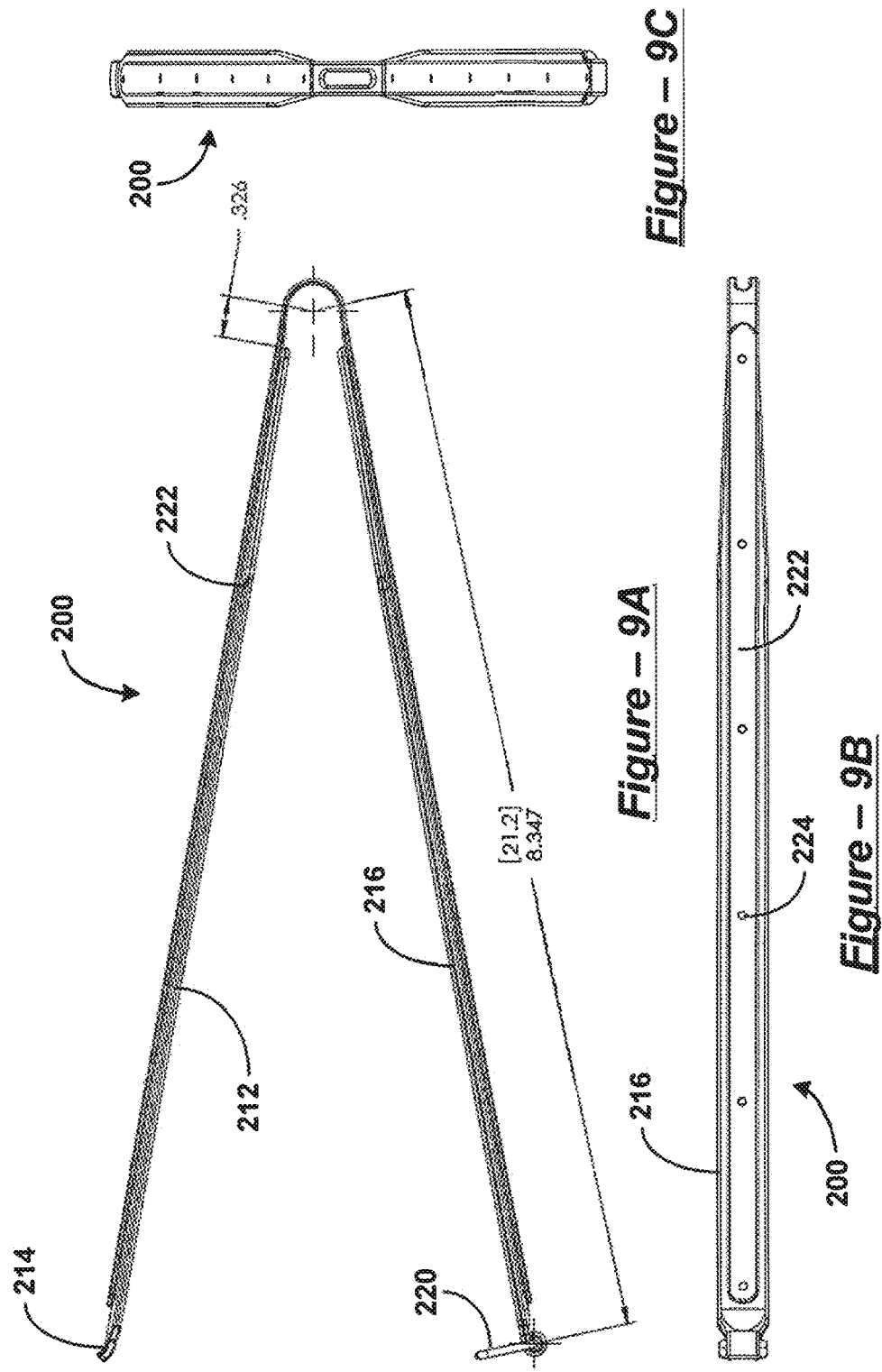

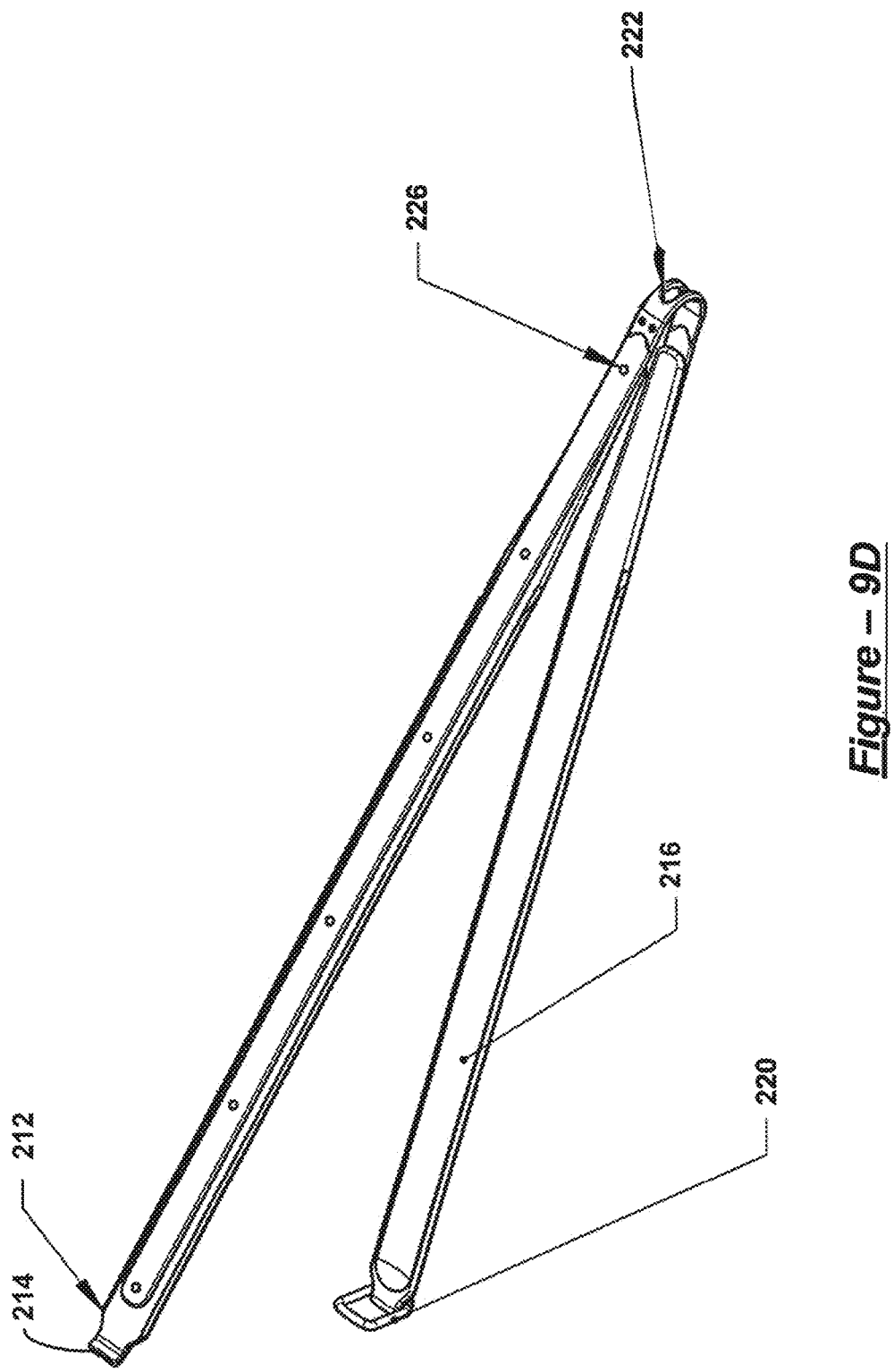
Figure — 9D

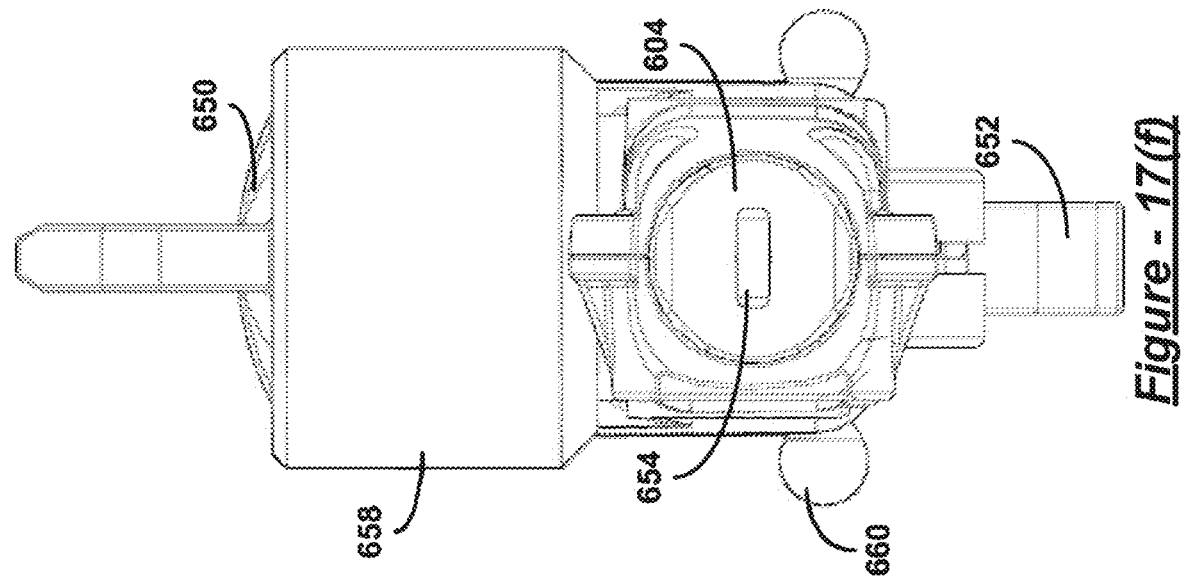
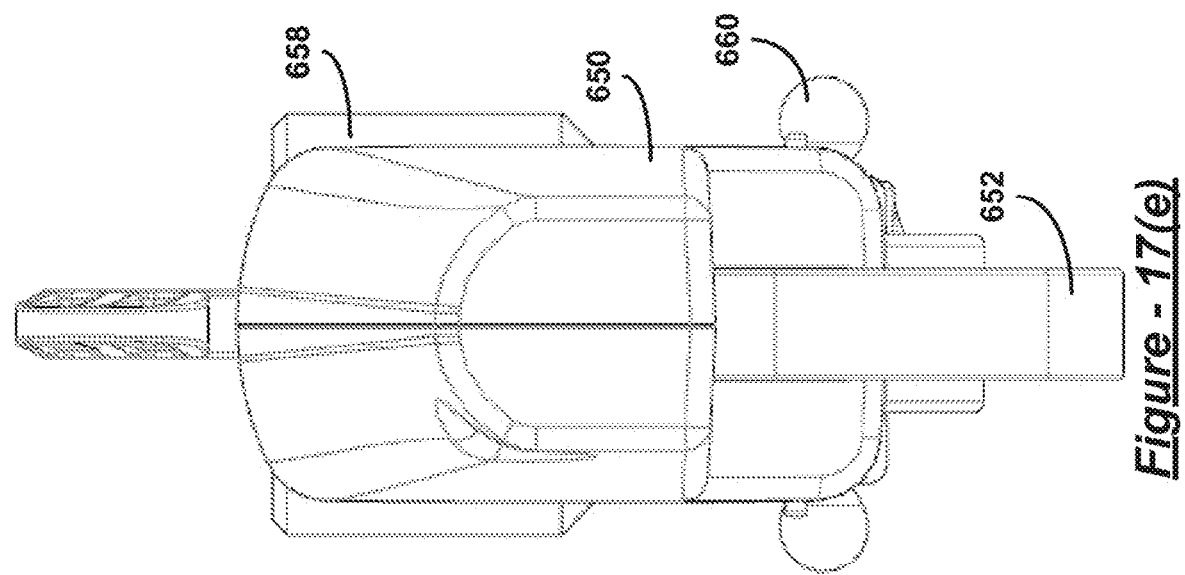

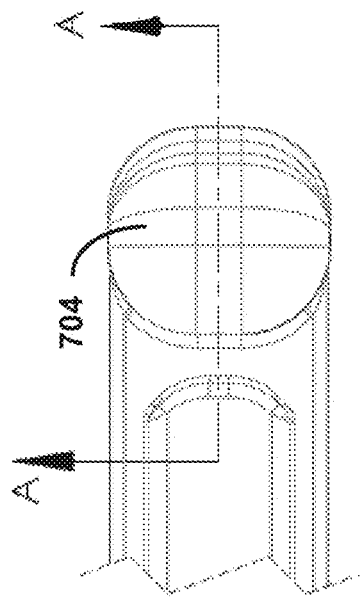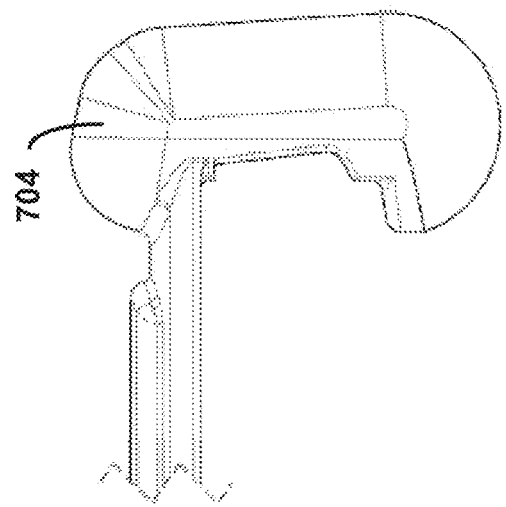
Figure - 23
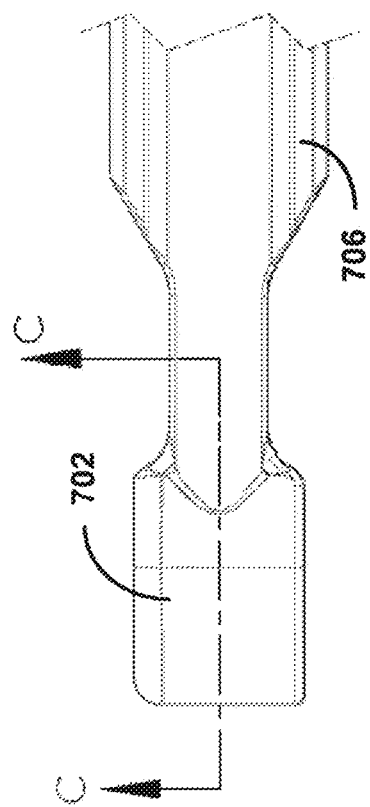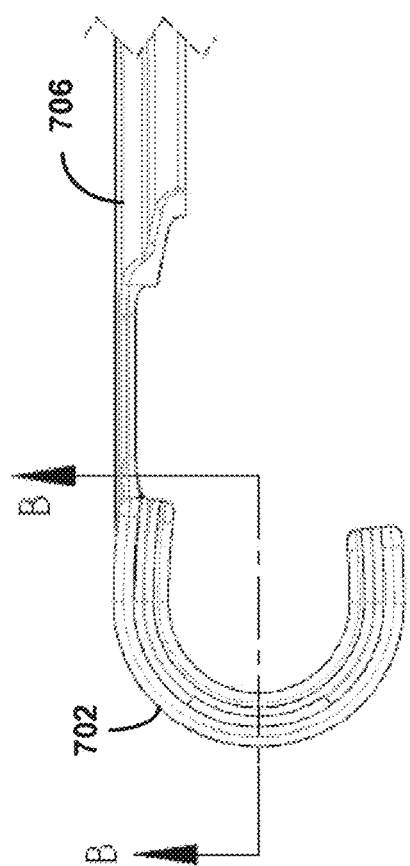
Figure - 24

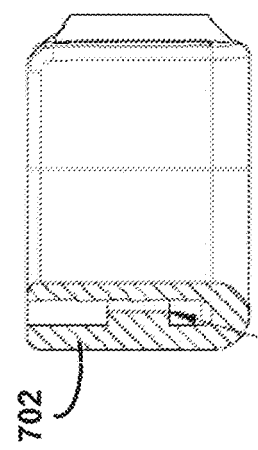
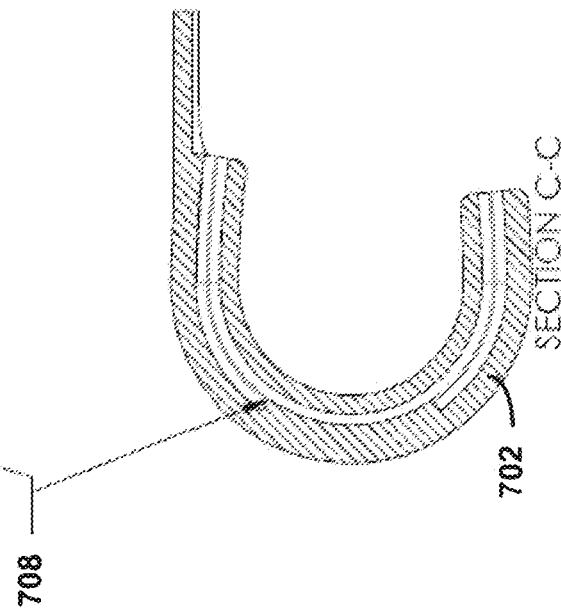
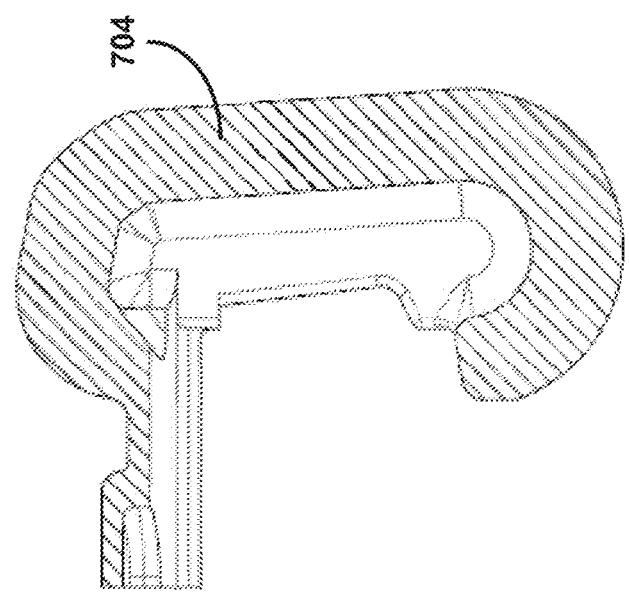

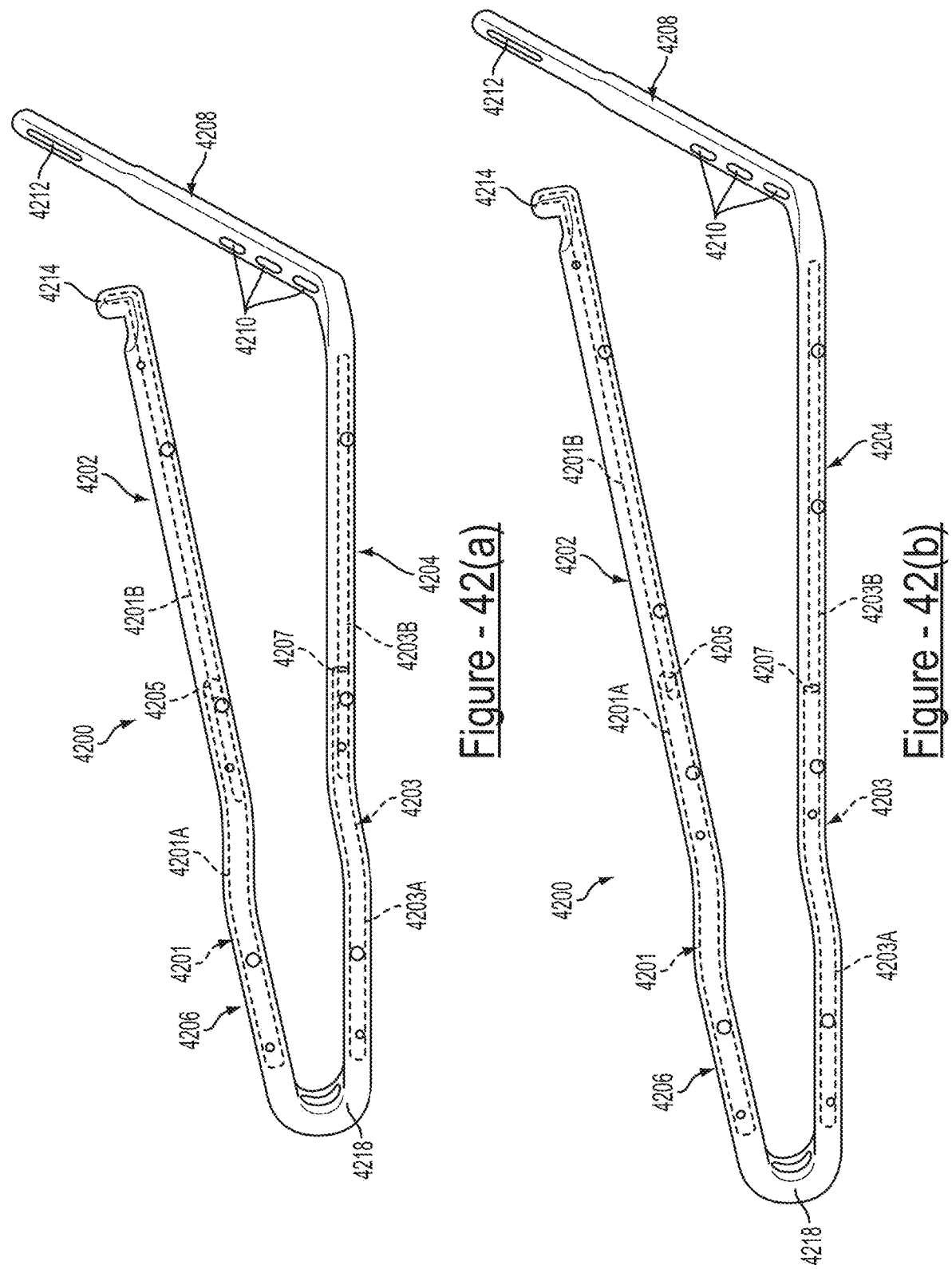

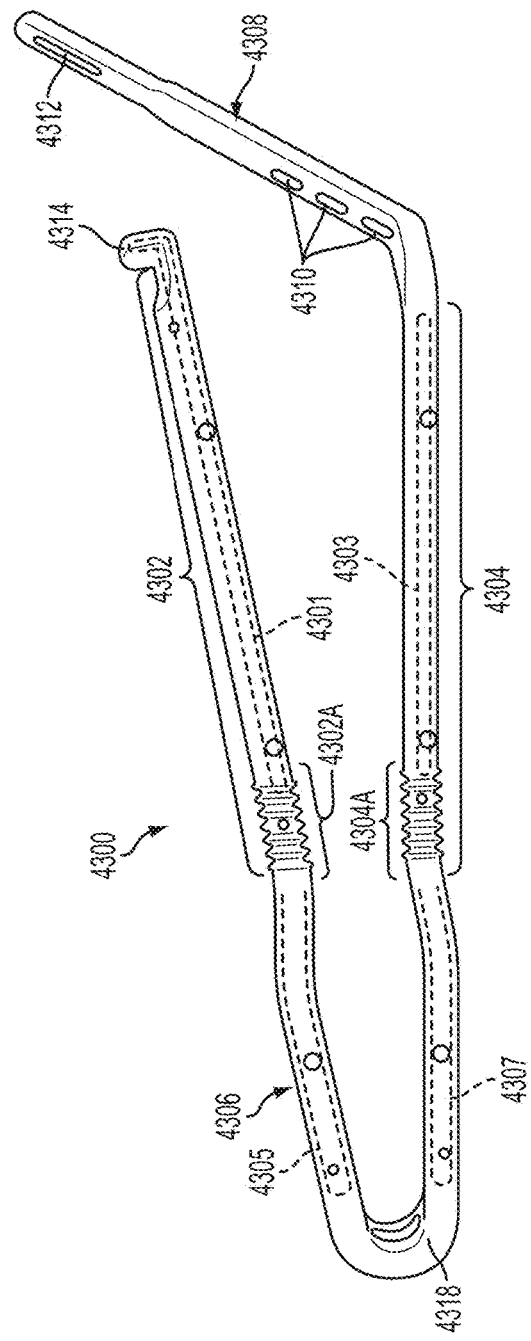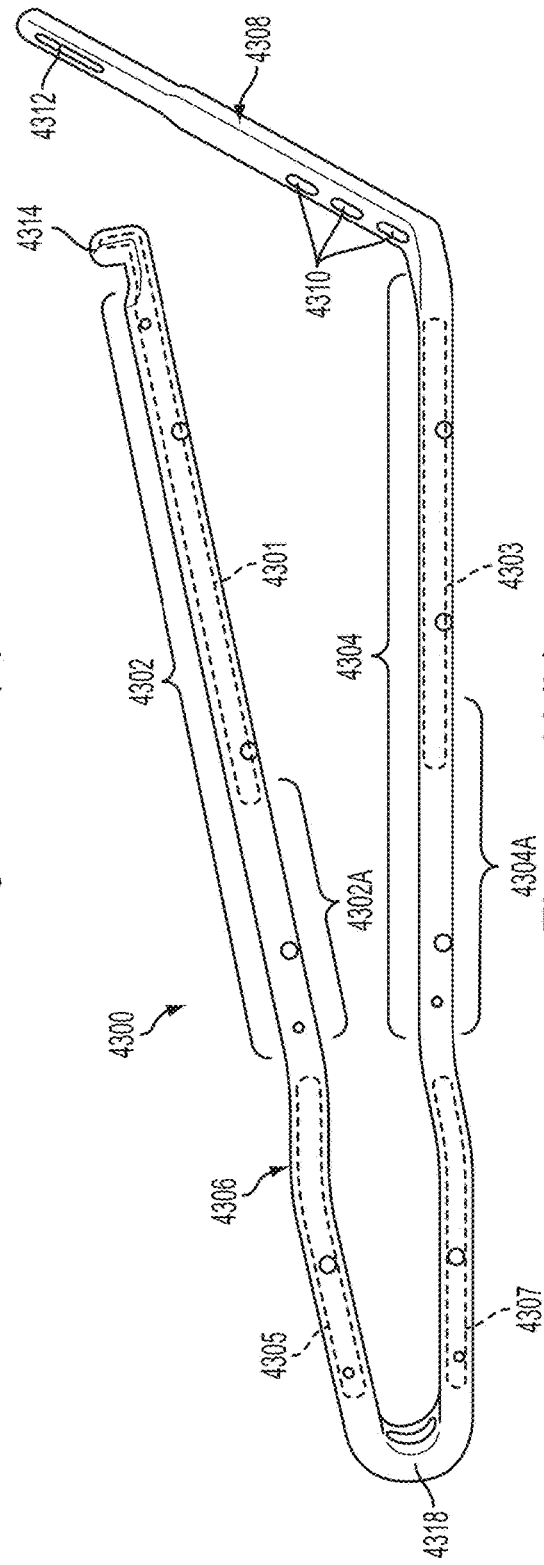
Figure – 43(a)
Figure – 43(b)

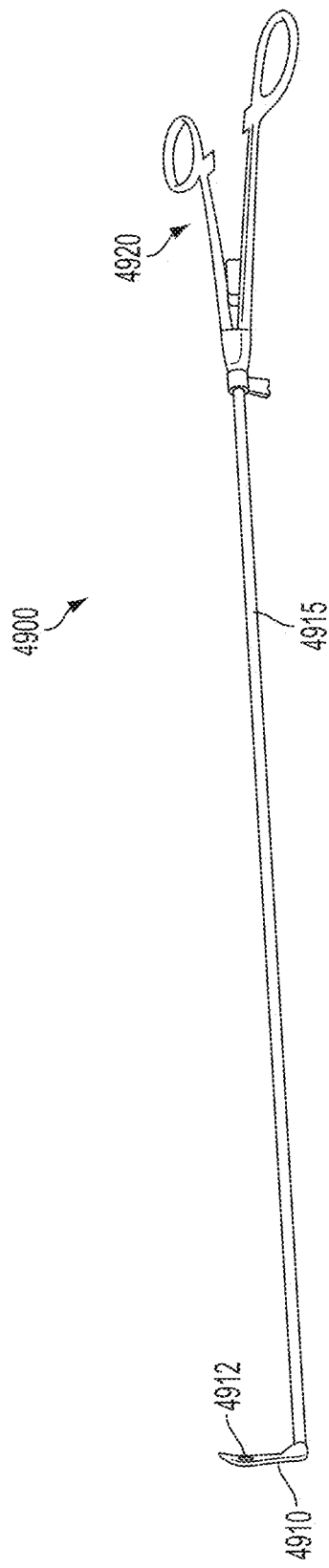
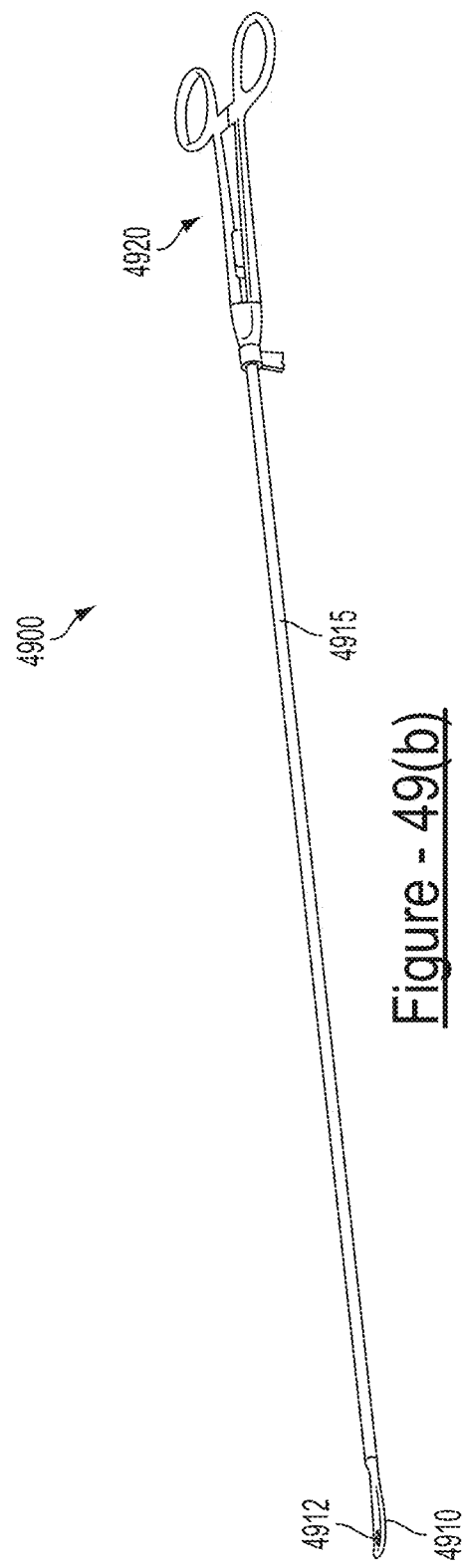
Figure - 49(a)
Figure - 49(b)

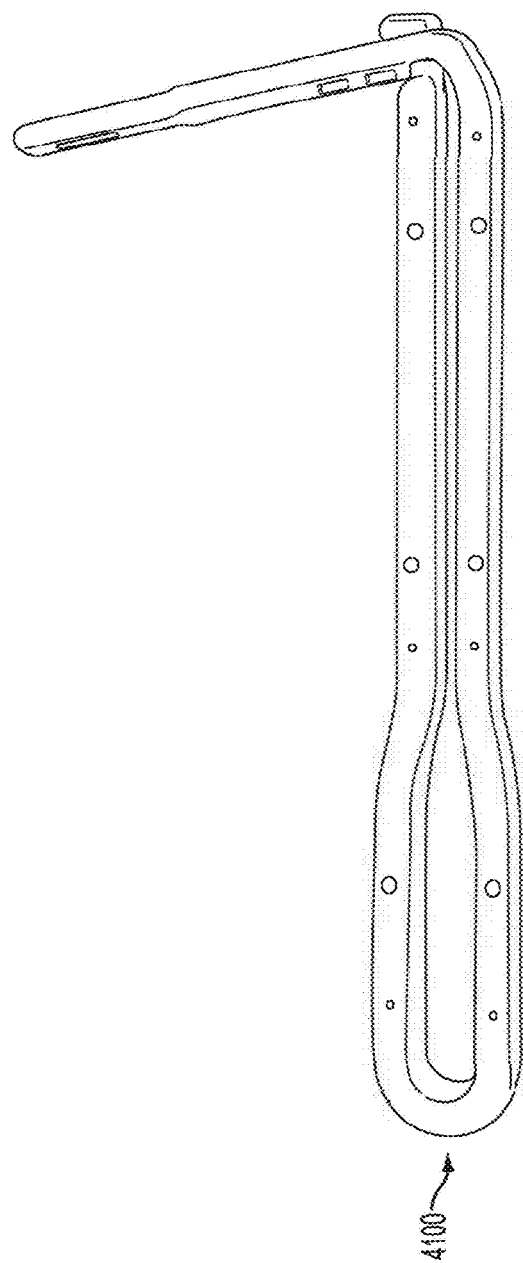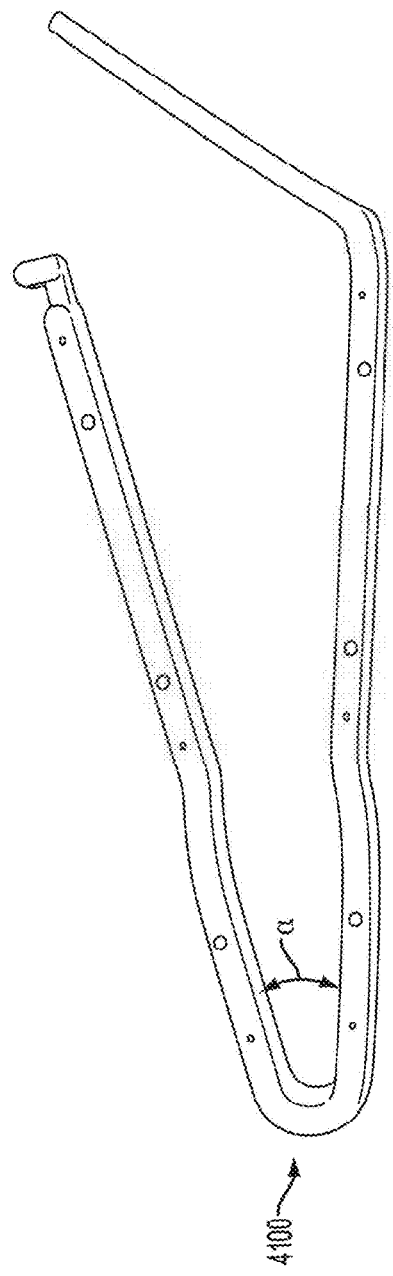
Figure - 50(a)
Figure - 50(b)

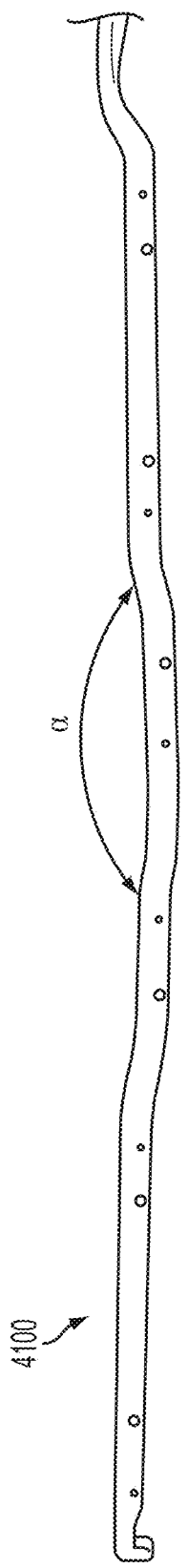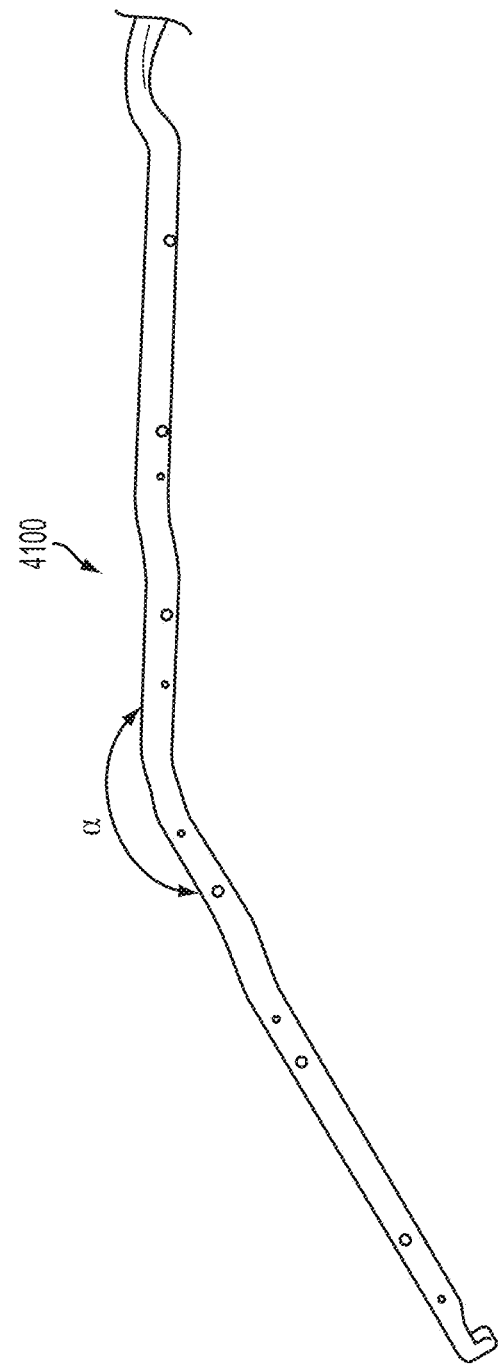
Figure - 50(c)
Figure - 50(d)

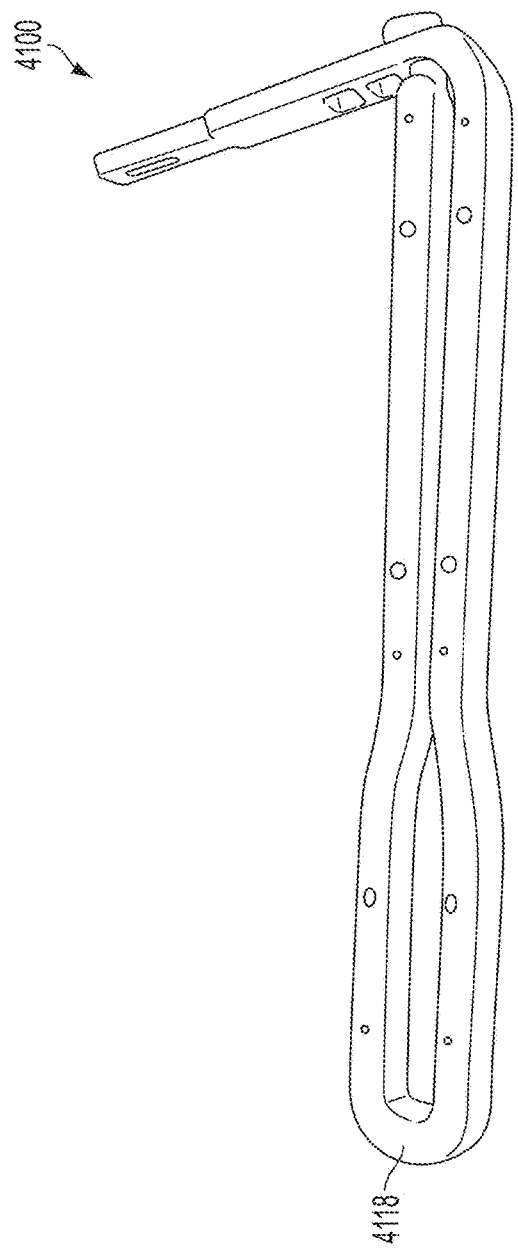
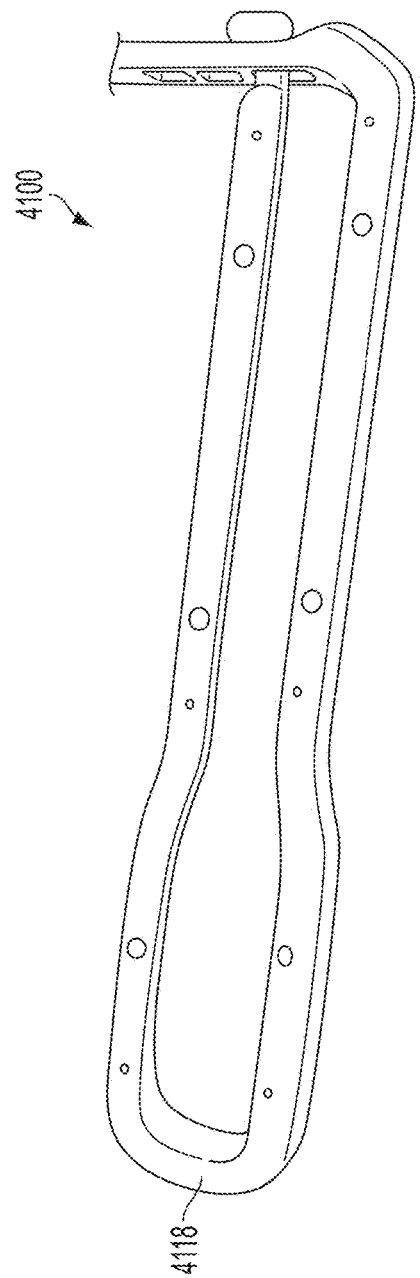
Figure - 52(a)
Figure - 52(b)

POLYMER OVERMOLDED BARIATRIC CLAMP AND METHOD OF INSTALLING

CROSS-REFERENCE TO RELATED APPLICATIONS

Pursuant to 35 U.S.C. § 119 (e), this application is a continuation of U.S. patent application Ser. No. 17/403,645, entitled "Polymer Overmolded Bariatric Clamp and Method of Installing," filed Aug. 16, 2021, and naming Jesús R. Armenteros, Moises Jacobs, and C. Kenneth French as inventors, which claims priority from U.S. patent application Ser. No. 16/664,447, entitled "Polymer Overmolded Bariatric Clamp and Method of Installing," filed Oct. 25, 2019, and naming Jesus R. Armenteros, Moises Jacobs, and C. Kenneth French as inventors, which claims priority from U.S. patent application Ser. No. 13/963,998, entitled "Polymer Overmolded Bariatric Clamp and Method of Installing," filed Aug. 9, 2013, and naming Jesus R. Armenteros, Moises Jacobs, and C. Kenneth French as inventors, which claims priority from U.S. Provisional Patent Application No. 61/681,601, entitled "Polymer Overmolded Bariatric Clamp and Installation Tool," filed Aug. 9, 2012, naming Jesús R. Armenteros, C. Kenneth French, Moises Jacobs, and Garrett Barker as inventors, and U.S. Provisional Patent Application Ser. No. 61/798,128, entitled "Polymer Overmolded Bariatric Clamp and Method of Installing," filed Mar. 15, 2013, naming Jesus R. Armenteros, C. Kenneth French, Moises Jacobs, and Garrett Barker as inventors, the disclosures of which are incorporated herein by reference in their entirety.

FIELD

The present disclosure relates generally to surgical clamps and surgical clamp installation tools.

BACKGROUND

The statements in this section merely provide background information related to the present disclosure and may not constitute prior art.

Recently, there has been increased interest in employing surgical clamps to partition sections of a stomach. An example of a bariatric surgical clamp can be found in Jacobs et al., U.S. patent application Ser. No. 11/984,452, Jacobs et al., U.S. patent application Ser. No. 11/797,537 and Jacobs et al. U.S. patent application Ser. No. 13/017,666. The aforementioned patent applications are incorporated by reference herein in their entirety for any purpose.

SUMMARY

In one embodiment, a method for installing a bariatric clamp having at least a first elongated portion, a second elongated portion, and a flexible hinge, the method comprising: creating an opening in an abdominal cavity of a patient to access a stomach of the patient; removing tissue connected to an exterior surface of the stomach adjacent areas where the bariatric clamp is to be positioned; positioning the bariatric clamp in an open position such that a first end of the first elongated portion and a first end of the second elongated portion are open relative to one another, and a second end of the first elongated portion and the second end of the second elongated portion are linked through one or more members that include the flexible hinge; inserting the bariatric clamp into the abdominal cavity through the opening while the clamp is positioned in the open position, and wherein the first elongated portion and the second elongated portion of the bariatric clamp separately pass through the opening in the abdominal cavity; positioning the second elongated portion of the bariatric clamp adjacent a portion of the exterior surface of a second side of the stomach; positioning the first elongated portion of the bariatric clamp adjacent a portion of the exterior surface of a first side of the stomach; and closing the bariatric clamp to apply pressure to the portions of the exterior surfaces of the stomach to at least partially partition a cavity inside the stomach.

In another embodiment, a bariatric clamp having a polymer overmold comprises: a first elongated portion having a first substrate member disposed, at least partially, within the first elongated portion, the first elongated portion including a first adjustable portion; a second elongated portion having a second substrate member disposed, at least partially, within the second elongated portion, the second elongated portion including a second adjustable portion; a bight portion having a first bight substrate member, a second bight substrate member and a flexible hinge formed from the polymer overmold at a proximal end of the bariatric clamp, the bight portion joining the first and second elongated portions; a fastener portion disposed towards a distal end of the second elongated portion; and an engagement portion disposed towards a distal end of the first elongated portion, the engagement portion operable to engage the fastener portion to retain the surgical clamp in a closed position.

Another embodiment provides a bariatric clamp comprising: a first elongated member having an engagement portion disposed at a first end of the first elongated member and a first receiving portion disposed towards a second end of the first elongated member; a second elongated member having a fastener portion disposed at a first end of the second elongated member and a second receiving portion disposed towards a second end of the second elongated member; and a bight member having a first retention feature operable to couple the bight member to the first receiving portion of the first elongated member, and having a second retention feature operable to couple the bight member to the second receiving portion of the second elongated member; wherein the first elongated member and second elongated member comprise a partition-forming section of the bariatric clamp, and the bight member comprises a passage-forming section of the bariatric clamp.

In yet another embodiment, the present disclosure provides a bariatric clamp having a polymer overmold, the bariatric clamp comprising: a first elongated portion having a first adjustable substrate member disposed, at least partially, within the first elongated portion; a second elongated portion having a second adjustable substrate member disposed, at least partially, within the second elongated portion; a bight portion having a flexible hinge formed from the polymer overmold at a proximal end of the bariatric clamp, the bight portion joining the first and second elongated portions; a fastener portion disposed towards a distal end of the second elongated portion; and an engagement portion disposed towards a distal end of the first elongated portion, the engagement portion operable to engage the fastener portion to retain the surgical clamp in a closed position.

Further embodiments and apparatuses, including other areas of applicability, will become apparent from the description provided herein. It should be understood that the description and specific examples are intended for purposes of illustration only and are not intended to limit the scope of the present disclosure in any manner.

BRIEF DESCRIPTION OF THE DRAWINGS

For a more complete understanding of various embodiments of the present invention and the advantages thereof, reference is now made to the following brief description, taken in connection with the accompanying drawings and detailed description, wherein like reference numerals represent like parts, and in which:

FIGS. 4(b), 4(c), 4(d), and 4(e) provide side cutaway views of various aspects of an embodiment of the surgical clamp installation tool;

FIG. 6A is a top view of a rigid member having a male clasp end for the clamp of FIG. 5;

FIG. 6B is a side view of the rigid member of FIG. 6A having the male clasp end for the clamp of FIG. 5;

FIG. 7A is a top view of a rigid member having a female clasp end for the clamp of FIG. 5;

FIG. 7B is a side view of the rigid member of FIG. 7A having the female clasp end for the clamp of FIG. 5;

FIG. 7C is a side view showing the female clasp end of FIG. 7B in greater detail;

FIG. 7D is a cross-sectional view showing a cross-section of the rigid member of FIG. 7A;

FIG. 8A is a top view of a spring member for the clamp of FIG. 5;

FIG. 8B is a side view of the spring member for the clamp of FIG. 5;

FIG. 9A is a side view of the clamp of FIG. 5;
FIG. 9B is a bottom view of the clamp of FIG. 5;
FIG. 9C is a proximal end view of the clamp of FIG. 5;
FIG. 9D is a perspective view of the clamp of FIG. 5;

FIG. 17(e) is a proximal handle end on view of the surgical clamp installation tool of FIG. 13;
FIG. 17(f) is a distal head end on view of the surgical clamp installation tool of FIG. 13;

FIG. 23 is a top view of the silicone sleeve of FIG. 20;
FIG. 24 is a left side view of the silicone sleeve of FIG. 20;
FIG. 25 is a cross-sectional view of a distal end of the silicone sleeve of FIG. 23;
FIG. 26 is a cross-sectional view of a proximal end of the silicone sleeve of FIG. 24;
FIG. 27 is a cross sectional view of a proximal end of FIG. 23;

FIGS. 42(a) and 42(b) illustrate an embodiment of an adjustable bariatric clamp in a retracted position and an extended position, respectively;

FIGS. 43(a) and 43(b) illustrate an embodiment of an adjustable bariatric clamp in a retracted position and an extended position, respectively;

FIGS. 49(a) and 49(b) illustrate various views of an example embodiment of an alignment device;

FIGS. 50(a), 50(b), 50(c) and 50(d) illustrate an embodiment of the disclosed bariatric clamp in various closed and opened positions;

FIG. 52(a) illustrates an embodiment of the disclosed clamp in a closed position, wherein the flexible hinge is in a compressed, or non-expanded position;

FIG. 52(b) illustrates an embodiment of the disclosed clamp in the closed position wherein the flexible hinge is stretched or expanded;

For FIGS. 5-9, dimensions are given in inches. However, it should be understood that various embodiments are not limited to the dimensions provided. Such dimensions are purely illustrative.

For FIGS. 4(b), 4(c), 17(a)-17(d), 21, 23, and 24, broken lines indicate variability in length of the discontinuous portions.

DETAILED DESCRIPTION OF THE DRAWINGS

The following description is merely exemplary in nature and is not intended to limit the present disclosure, application, or uses. It should be understood at the outset that although an exemplary implementation of the present invention is illustrated below, the present invention may be implemented using any number of techniques, whether currently known or in existence. The present invention should in no way be limited to the exemplary implementations, drawings, and techniques illustrated below, including the exemplary design and implementations illustrated and described herein. Additionally, the drawings contained herein are not necessarily drawn to scale, and may be provided in a variety of different dimensions, shapes and configurations. Any provided dimensions are provided only to illustrate a particular exemplary implementation, and should in no way be construed to limit the present invention absent an explicit recitation of such dimensions and then only with respect to the claim or claims reciting the dimension or dimensions.

Figure 1:
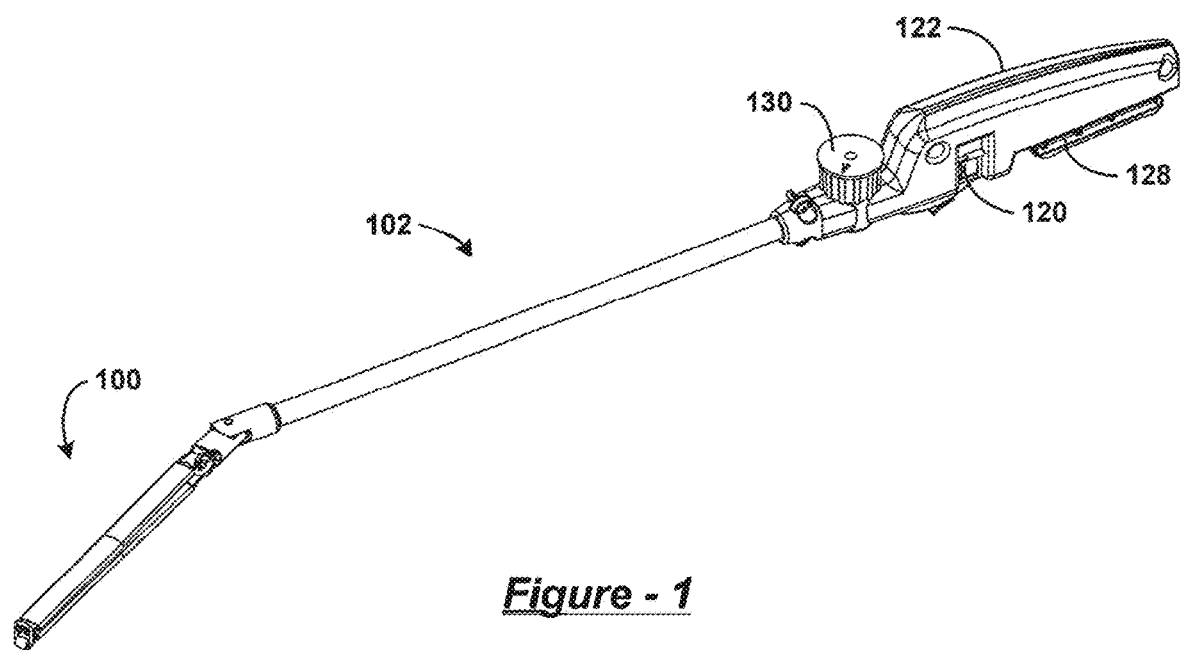
FIG. 1 is a view of an embodiment of a surgical clamp engaged with an embodiment of a surgical clamp installation tool having an articulating head.

Referring to FIG. 1, an embodiment of a surgical clamp 100 (also referred to herein as a bariatric clamp) engages with an embodiment of a surgical clamp installation tool 102. In these embodiments, the clamp 100 and the installation tool 102 are designed for performing bariatric surgery through a surgical trocar. The clamp 100, in a preferred embodiment, may be approximately fifteen to thirty centimeters in length to accommodate partitioning of a human stomach. To accommodate insertion through a trocar, the closed clamp 100 will preferably have a diameter or circumference less than fifteen millimeters over the entirety of its length or along the majority of its length. A non-handle section of the installation tool 102 intended for insertion through the trocar has a similar diameter or a smaller diameter. It is envisioned that other embodiments of the clamp and installation tool can be of other sizes. It is additionally envisioned that the clamp may be articulated in at least one plane to provide different angles and lengths of partition to the stomach. It is also envisioned that other embodiments of the clamp and installation tool can be used for clamping other parts of the human body and/or for clamping other types of bodies or structures. Finally, it should be understood that the installation tool 102 may be used to install embodiments of the surgical clamp other than those explicitly illustrated in the figures.

Figure 2A:
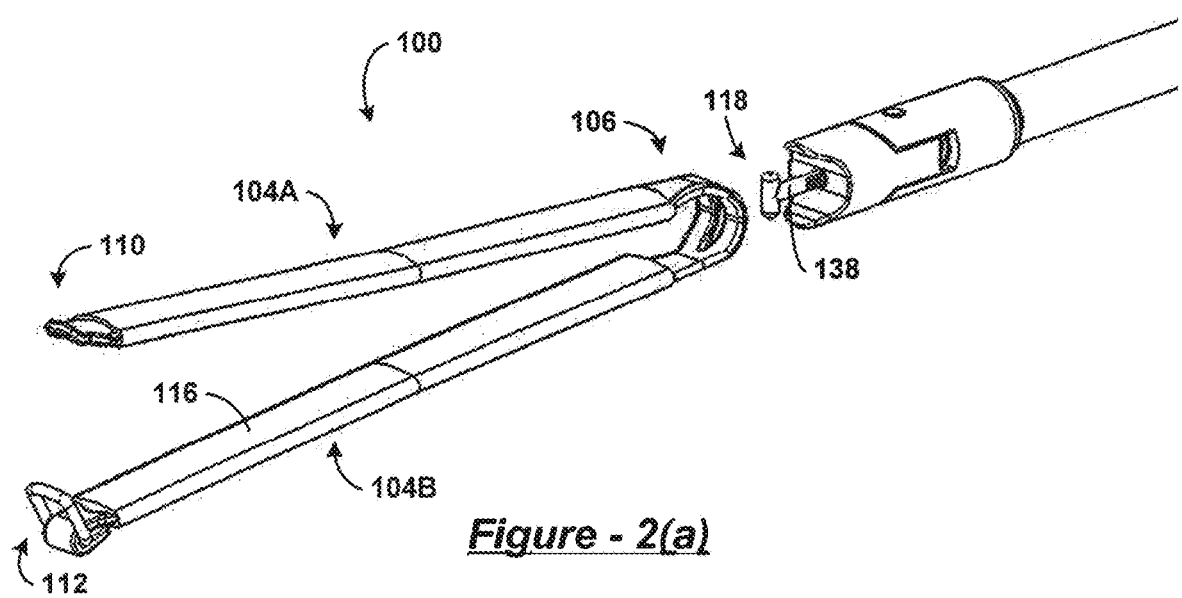
FIG. 2 is a set of views illustrating engagement of the surgical clamp to the articulating head of the surgical clamp installation tool at FIGS. 2(a), 2(b), and 2(c), and actuation of the clamp at FIG. 2(d) to a closed position at FIG. 2(e), and illustrating a six-sided view of the clamp, including a top view at FIG. 2(f), a left side view at FIG. 2(g), a bottom view at FIG. 2(h), a right side view at FIG. 2(i), a view facing the distal end at FIG. 2(j), and a view facing the proximal end at FIG. 2(k)

Referring to FIG. 2(a), the surgical clamp 100 has two elongated members 104A and 104B. A bight portion 106 joins the two elongated members at a proximal end of the clamp 100 and biases the two elongated members in an open position at a distal end of the clamp 100. As used herein, a bight is a loop, bend, hinge, corner angle, hollow, fold, or similar structure. In some embodiments, the bight portion has one or more engagement features, such as, for example, a slotted aperture 108 such as that shown in FIG. 2(b). It should be understood that, in some embodiments, the engagement feature(s) of the bight portion may be referred to as an attachment feature. A clasp mechanism, in one embodiment, has a male component 110 disposed on one of the two elongated members at the distal end, and a female component 112 disposed on the other of the two elongated members at the distal end.

Particularly to partially partition a stomach in performing bariatric surgery, spacing between the two elongated members 104A and 104B effects two or more clamp sections as best shown in FIG. 2(e). At least one of the sections is a partition forming section 105A located nearer the distal end of the clamp 100 than the proximal end of the clamp 100. At least another of the sections is a passage forming section 105B located nearer the proximal end of the clamp 100, such as near the bight portion 106, than the distal end of the clamp 100.

In order to reduce injury to the partitioned organ, a padding material 116 can be connected to one or more of the two elongated members. For example, padding material 116 can connect to the elongated member 104B at least at a location corresponding to at least part of the partition forming section. In some embodiments, the padding material can be composed predominantly of silicone or fully of silicone, or other polymer material. It is also envisioned that the opposing limbs of the clamp may be fitted with magnets to facilitate closure.

Figure 2B:
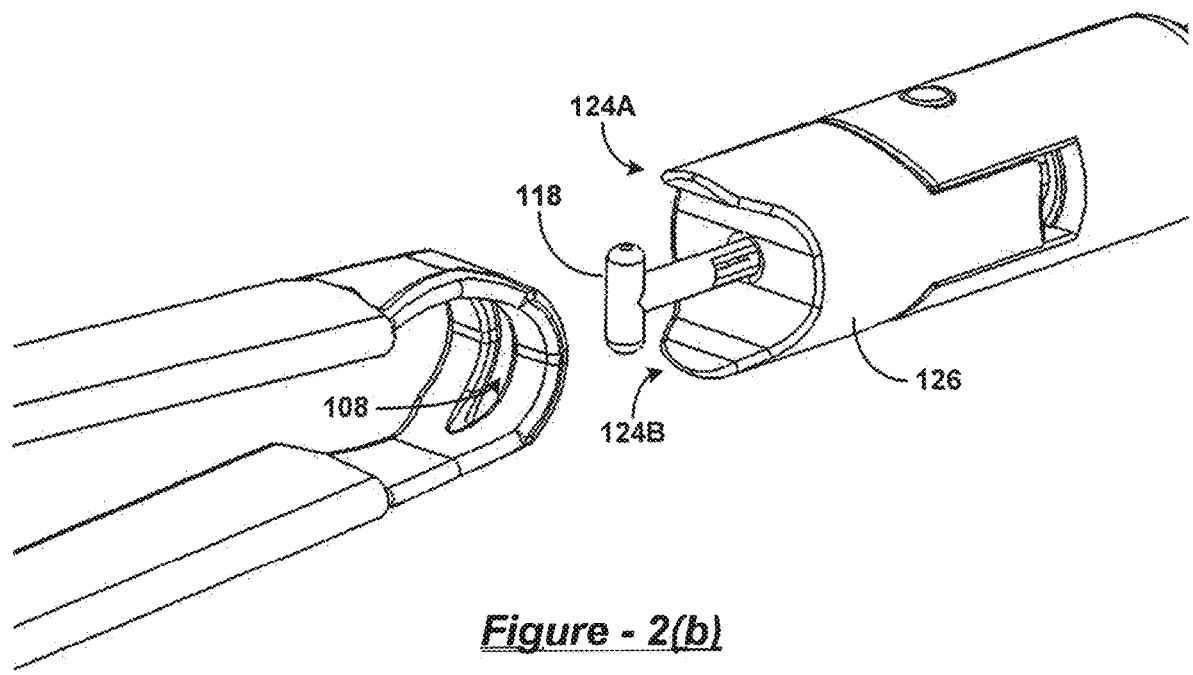
Figure 2C:
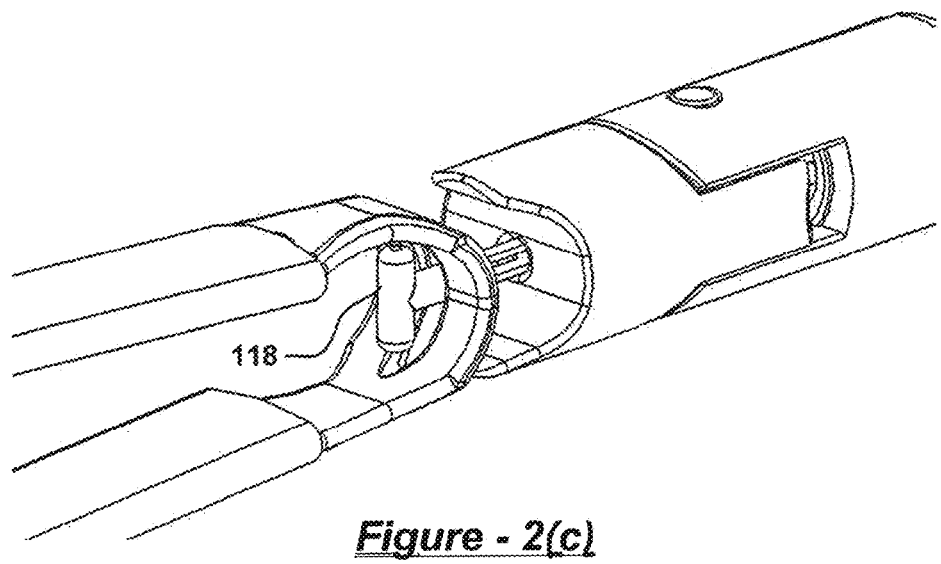
Figure 2F:
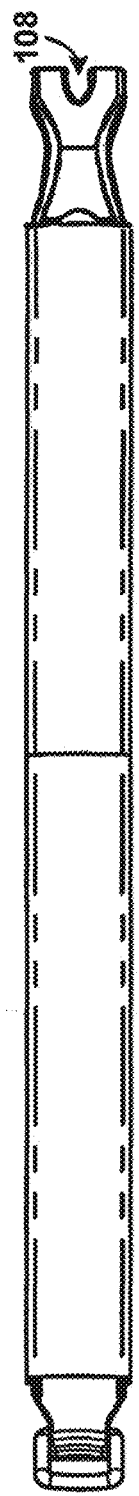
Figure 2G:
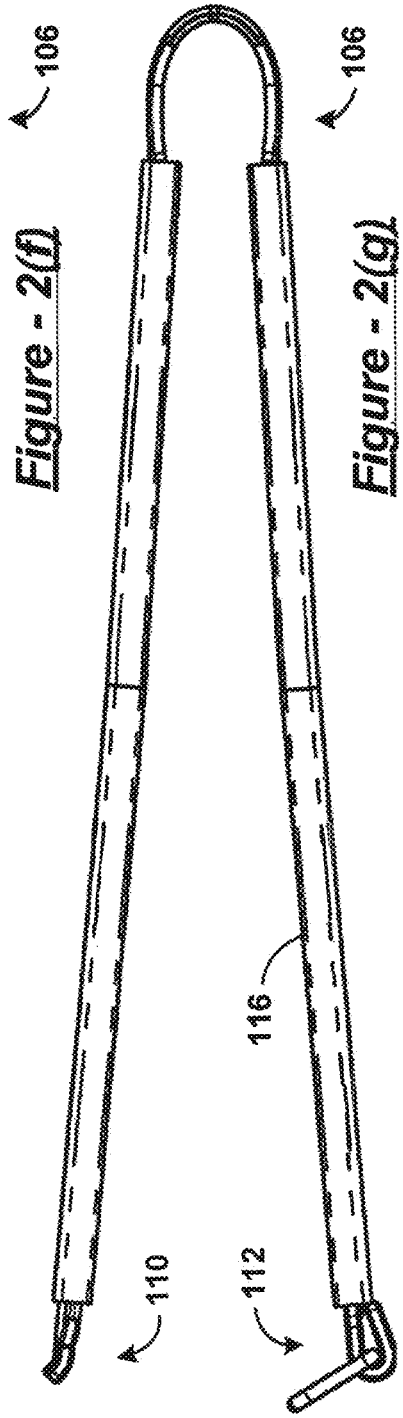
Figure 2H:
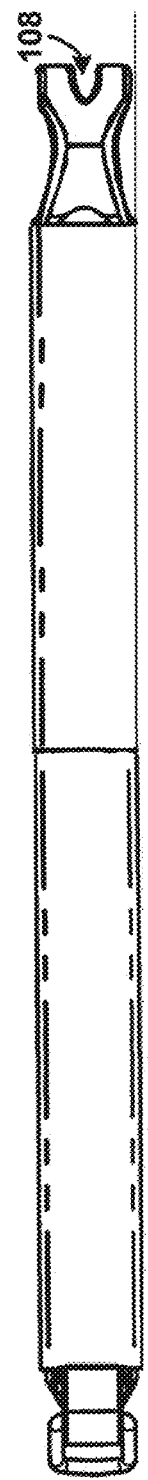
Figure 2I:
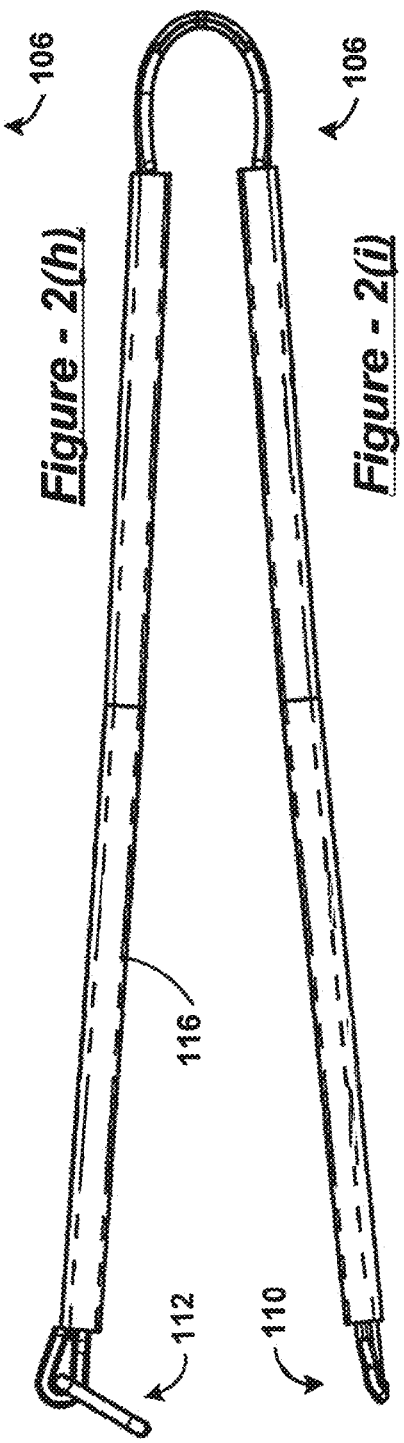
Figure 3A:
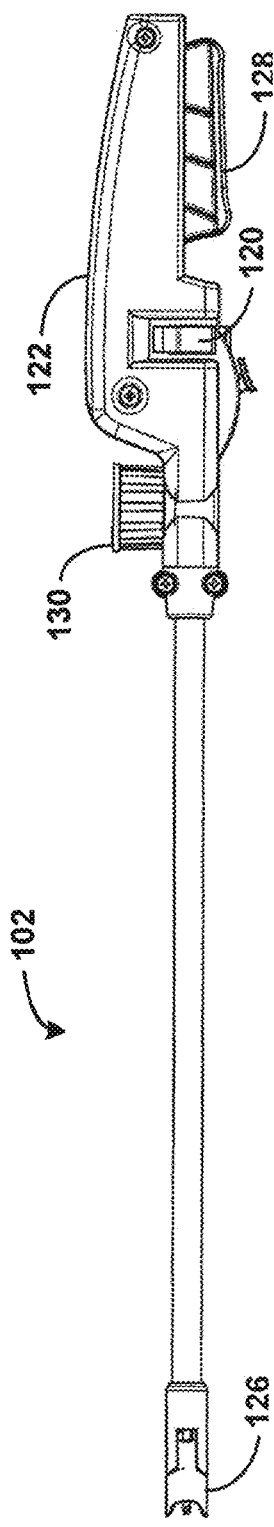
FIG. 3 is a set of views illustrating the surgical clamp installation tool from six sides with the right side of the housing of the handle shown removed, including a left side view at FIG. 3(a), a top view at FIG. 3(b), a right side view at FIG. 3(c), a bottom view at FIG. 3(d), a view facing the distal end at FIG. 3(e), and a view facing the proximal end at FIG. 3(f)
Figure 3B:
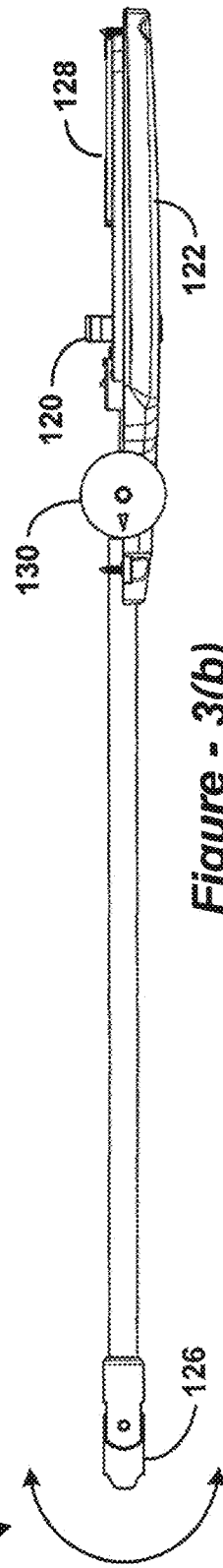
Figure 3C:
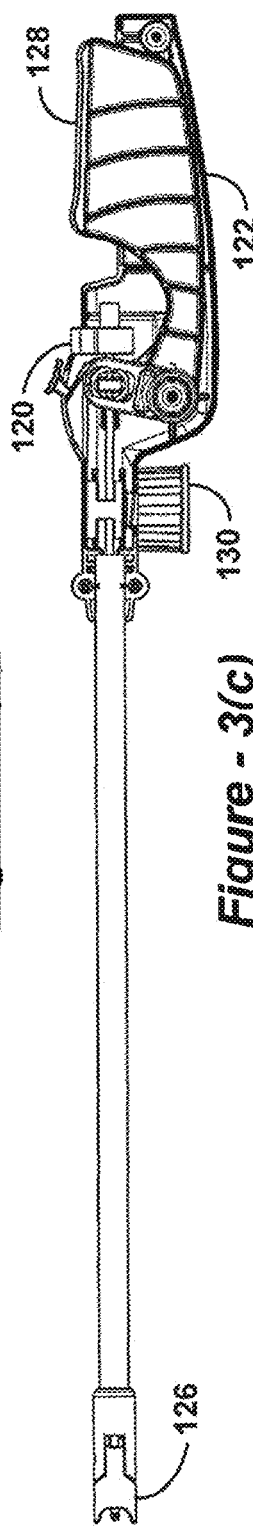
Figure 3D:
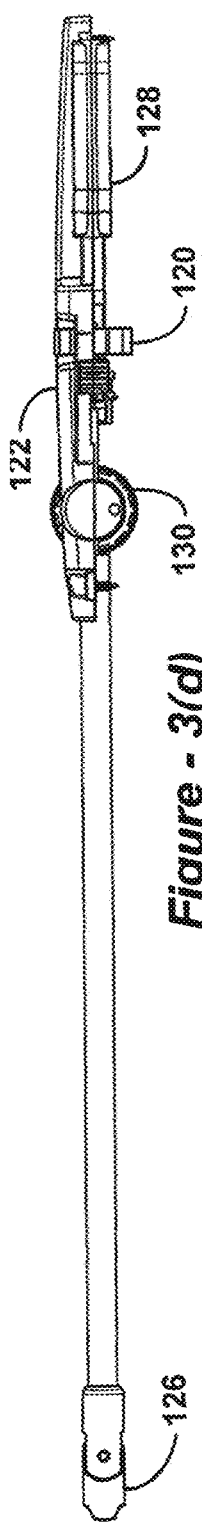
Figure 3F:
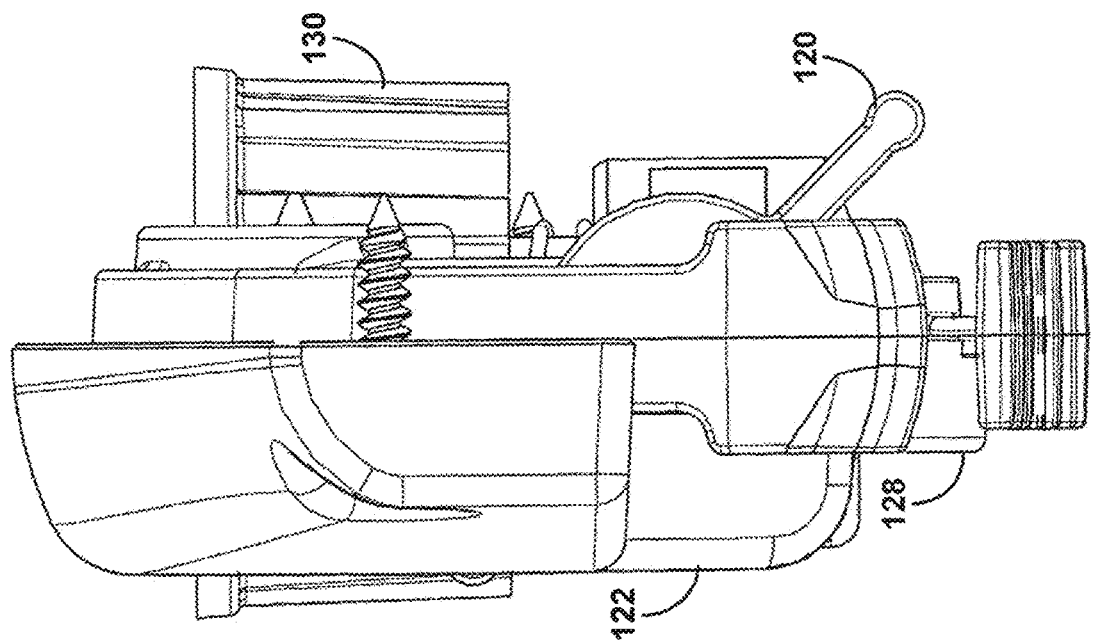
Figure 3E:
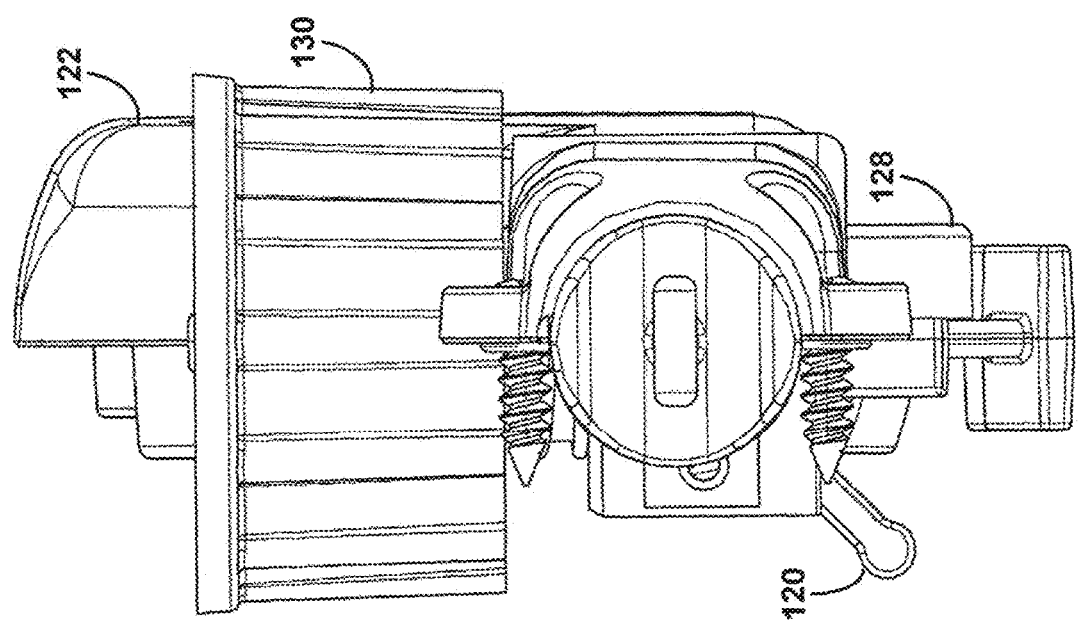

In some embodiments, the engagement feature at the proximal end of the clamp 100 can be a slotted aperture 108 as shown in FIG. 2(b) having a width and a length larger in size than the width. The length of the slotted aperture can be oriented perpendicular or angled with reference to a longitudinal axis of the clamp 100. It is envisioned that other types engagement features can be employed, such as a socket, a loop, a hook, a clasp, a string, magnet, etc.

In some embodiments, the male component 110 of the clasp at the distal end of the clamp can be an end of the elongated member 104A that flares away from a longitudinal axis of the clamp when the clamp is forced to a closed position. Accordingly, the female component 112 can be a loop attached to the end of the elongated member 104B and disposed to engage the male component 110 of the elongated member 104A when the clamp is forced to the closed position. This can be seen more clearly in connection with FIG. 2(e). It is envisioned that other types of clasp components can be employed, such as those found in a hinge, such as a living hinge, hook and loop, spring ring, lobster or trigger, toggle, tube, bolt and bolt hole, screw and threaded aperture, or any other type of closure arrangement.

Returning to FIG. 1 and referring generally to both FIG. 1 and FIG. 2, the clamp 100, in use, engages with the installation tool by the slotted aperture 108. For example, the installation tool 102 has an elongated member, such as a pull-rod 138, having a proximal end and a distal end that has an engagement feature. The distal end of the elongated member of the installation tool 102 engages with the proximal end of the clamp 100 through the slotted aperture 108 of the bight portion 106. In some embodiments, the engagement feature takes the form of a T-bar 118. This T-bar 118 is sized and shaped to allow insertion thereof through the slotted aperture 108 to engage the clamp 100. It is envisioned that another engagement features may have an X-shape, and be sized for insertion through an X-shaped slot in the clamp. Other shapes are also possible.

The installation tool 102 may include a lever radially engaged with the pull-rod at its proximal end at a handle 122 that may be configured as a thumbwheel 120 that extends out of the handle 122 of the installation tool 102 through an aperture. While the T-bar 118 is inserted through the slotted aperture 108, actuating the thumbwheel 120 can cause the T-bar 118 to rotate ninety degrees as illustrated in one embodiment from a first position shown in FIG. 2(c) and in a second position as shown in FIG. 2(d).

At this point, retracting the pull rod, which may be achieved by squeezing a trigger 128 to retract the pull rod, forces the proximal end of the clamp 100 up against and progressively further between guide members of the surgical clamp installation tool 102, such as a pair of wedges 124A and 124B, formed in the articulating head 126 of the installation tool 102(see FIG. 2(b)). A curvature or incline imparted to the articulating head of the installation tool 102 by the pair of wedges can be keyed to a curvature or incline of the bight portion 106 of the clamp 100 in such a way that fully or more fully retracting the pull-rod forces the normally open clamp 100 to a closed position such as that shown in FIG. 2(e).

Turning to FIGS. 2(f)-2(k), the various clamp features can be readily appreciated. These features include bight portion 106, slotted aperture 108, male component 110, female component 112, and padding material 116. It should be readily understood that the padding material 116 can be configured as a pair of sleeves as shown, but that other configurations may also be employed. Moreover, non-linear shapes may be utilized for various types of applications in clamping various types of organs, as desired.

Turning now to FIG. 3 and referring generally to FIG. 1 and FIG. 3, retraction of the pull-rod of the installation tool 102 is accomplished by actuation or movement of another lever or trigger that is engaged to the proximal end of the pull-rod, such as through an axial engagement. This lever can be configured as the trigger 128 that extends out of the handle 122 through an aperture or slotted opening. The shape of the handle and disposition of the trigger are, preferably, ergonomically configured to allow the surgeon to hold the installation tool parallel to the ground near waist level to grip the handle 122 and the trigger 128 in one hand. The thumbwheel 120 is disposed to be within easy reach of the thumb of that hand to facilitate holding of the clamp 100 by the surgeon in the other hand while engaging the clamp to the articulating head 126. The thumbwheel 120 may be conveniently adjusted to rotate the T-bar 118 to a desired position to lock the T-bar 118 to the clamp 100 at the bight portion 106 through the slotted aperture 108. In one embodiment, the thumbwheel 120 may rotate the T-bar 118 by ninety degrees.

Once the surgeon has rotated and retracted the pull-rod using T-bar 118 and trigger 128 with one hand, the surgeon's other hand becomes free for other tasks, such as actuating yet another lever protruding from the handle 122 and configured, for example, as a dial 130. With the clamp 100 pulled closed or partially closed against the pair of wedges, the head 126 can be articulated from side to side by rotating this dial 130. The motion of the articulating head 126 through rotation of the dial 130 is illustrated in one embodiment in the top view of the installation tool 102 in FIG. 3(b) at arrow 300 showing a range of motion or articulation in one embodiment.

Figure 4A:
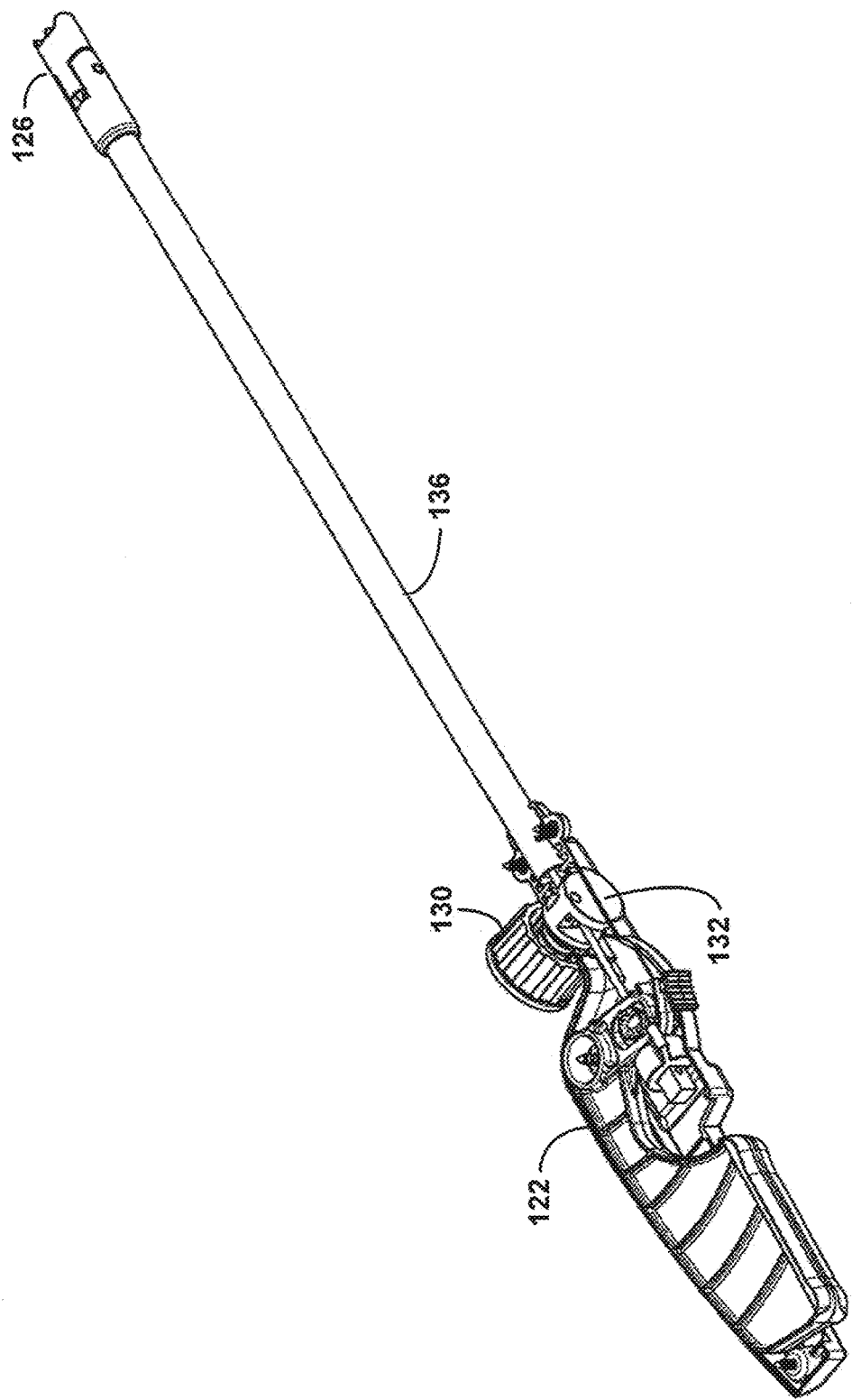
FIG. 4(a) is a perspective view illustrating an exemplary surgical clamp installation tool with the right side of the housing of the handle shown removed.

Turning now to FIG. 4, in some embodiments, turning the dial 130 can turn a hub 132 or connector inside or adjacent the handle 122 that is connected to a pair of guidelines 134A and 134B. These guidelines 134A and 134B, together with pull-rod 138, may extend through an elongated, rigid sleeve, such as a cylindrical tube 136, for connection on either side of a swivel mount of the articulating head 126. It is envisioned that the guidelines can be flexible or rigid, that the cylindrical tube 136 can be rigid or semi-rigid, and that the pull-rod 138 can be rigid or semi-rigid. By semi-rigid, it is meant that the pull-rod 138 can be flexible or partially flexible at least in the plane of articulation along at least part of its length near the distal end of the installation tool 102, but still axially and rotationally rigid or semi-rigid along its length. Thus, when the installation tool 102 and clamp 100 are held parallel to the ground, the pull-rod 138 can be rotated and retracted by actuation of the thumbwheel 120 and trigger 128, and the head 126 can be articulated in a plane orthogonal to the gravity vector by manipulation of the dial 130. The plane of articulation may be adjustable in certain embodiments, or may be set in a desired plane that is not orthogonal to the gravity vector.

Figure 5:
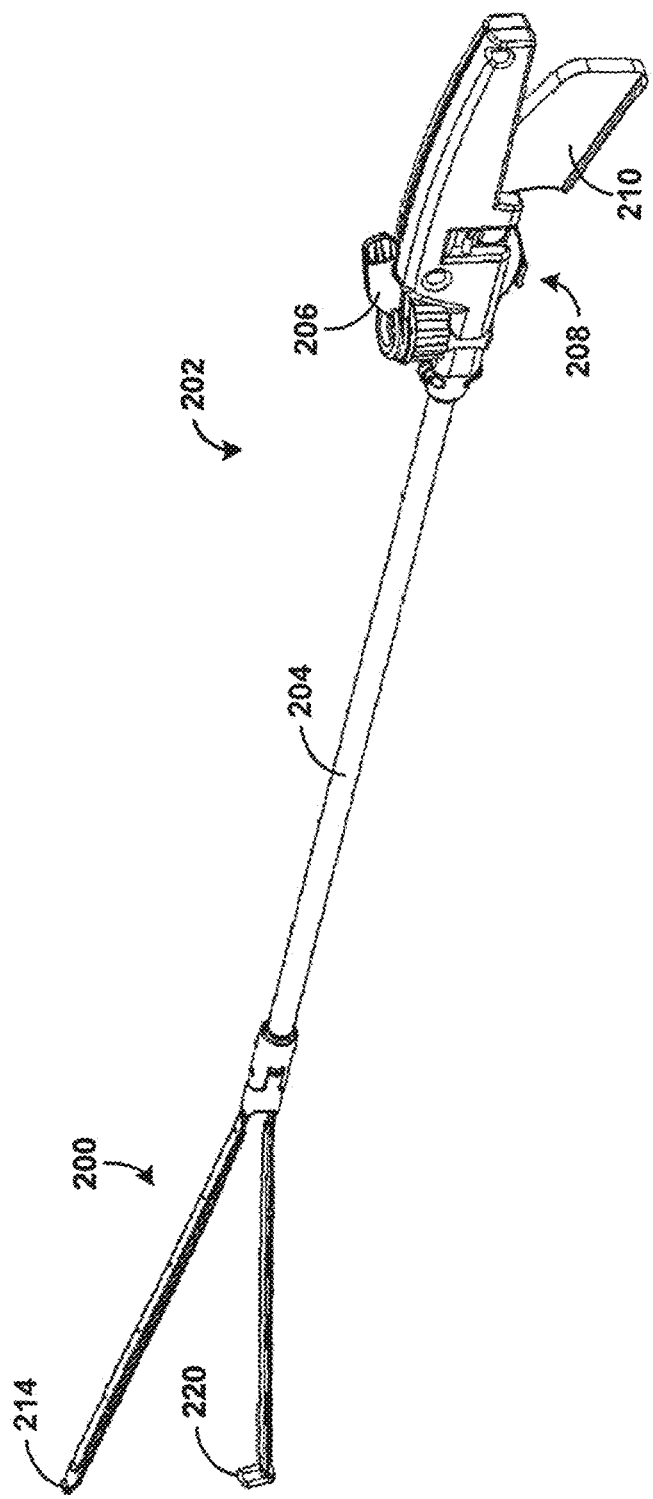
FIG. 5 is a view of another embodiment of a surgical clamp engaged with another embodiment of a surgical clamp installation tool having an articulating head.

Turning now to FIG. 5, other embodiments of the clamp 200 and installation tool 202 can include a clamp 200 made of multiple pieces, a longer main tube 204, and a thumb lever 206 on the dial 130 to articulate the head of the tool 102 that is attached to the clamp 200. In some embodiments, the clamp 200 can be a three-piece clamp. A ratchet release 208 can also be provided on the installation tool 202 that, when pressed, allows the pull rod to extend, which in turn will release the clamp 200 allowing it to reopen. In other words, as the surgeon presses on the trigger 210, causing the pull-rod to retract and the clamp 200 to close, a ratchet mechanism catches the trigger 210 in the pressed-in position. Thus, the pull-rod will remain retracted and clamp 200 will not reopen even if the surgeon releases pressure on the trigger 210.

Figure 6D:
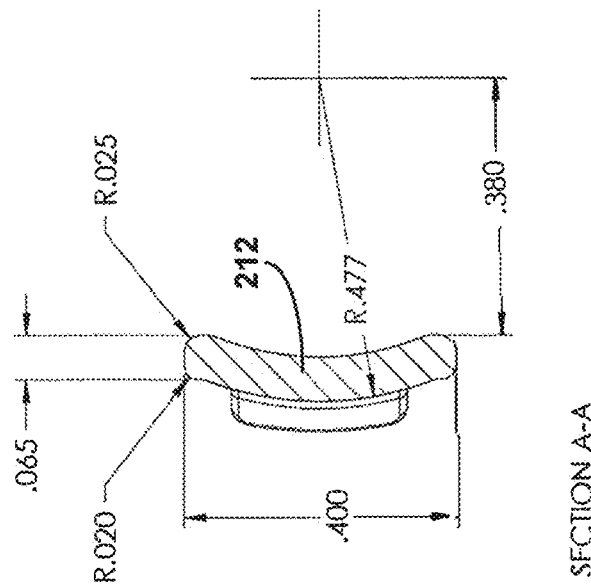
FIG. 6D is a cross-sectional view showing a cross-section of the rigid member of FIG. 6A.
Figure 6C:
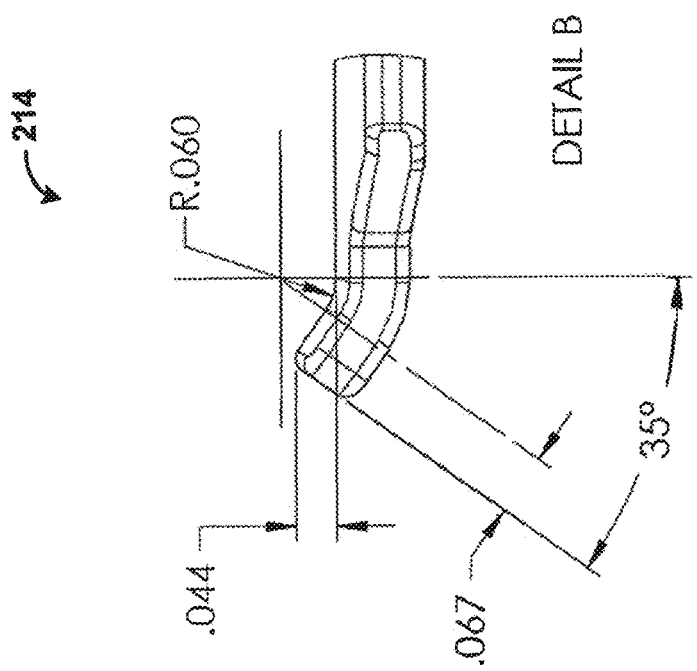
FIG. 6C is a side view showing the male clasp end of FIG. 6B in greater detail.

Turning now to FIG. 6, and referring generally to FIGS. 6A-6D, one piece of a three-piece clamp can be a rigid member 212 having a male clasp end 214. As will be described further below with reference to FIG. 9, this rigid member 212 serves as one of the elongated members of the clamp 200 for forming the partition that divides the stomach. It can be made of plastic, metal, or any other rigid material. An example material is hardened titanium. FIG. 6(c) demonstrates an exemplary contour of male clasp end 214, while FIG. 6(d) demonstrates an exemplary contour rigid member 212. It should be readily understood that the exemplary contour of rigid member 212 renders it concave on an inner surface to be disposed toward an outer surface of an organ to be clamped, and convex on an outer surface for engagement with a spring component. However, other shapes may be used as desired.

Turning next to FIG. 7, and referring generally to FIGS. 7A-7D, another piece of the three-piece clamp can be a rigid member 216 having a female clasp end 218 that includes a hinged loop 220. As will be described further below with reference to FIG. 9, this rigid member 216 serves as one of the elongated members of the clamp for forming the partition that divides the stomach. It can be made of plastic, metal, or any other rigid material. An example material is hardened titanium. Similarly, the loop 220 can be made of various materials, an example of which is titanium wire.

Figure 8D:
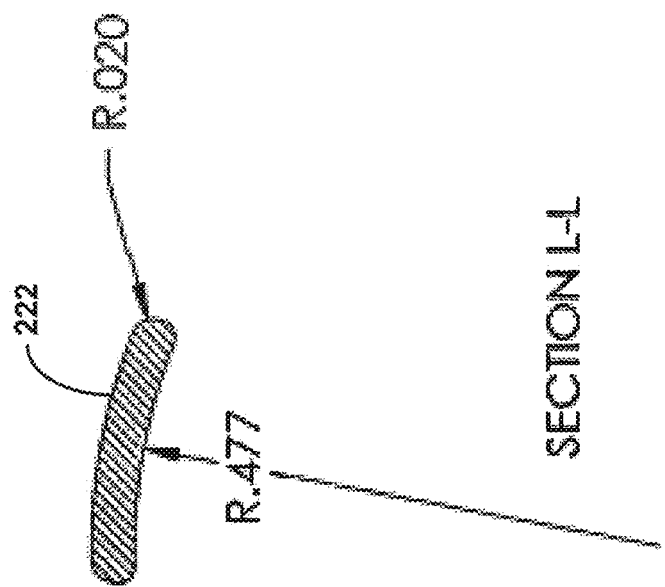
FIG. 8D is a proximal end view of the spring member of FIG. 5.
Figure 8C:
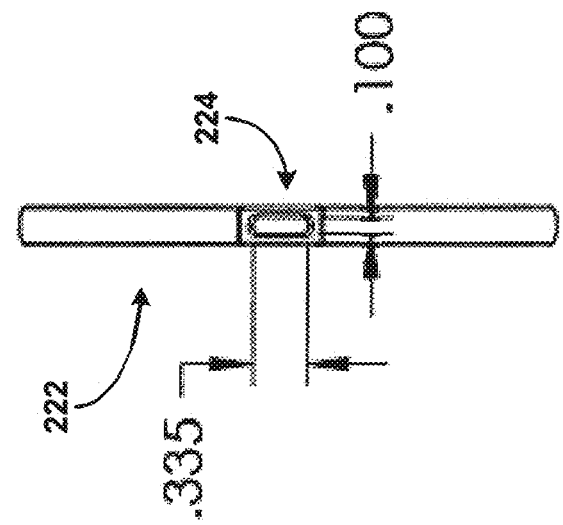
FIG. 8C is a cross-sectional, close-up view showing a cross-section of the spring member of FIG. 8B.

Turning next to FIG. 8, and referring generally to FIGS. 8A-8D, a third piece of the three-piece clamp can be a spring member 222 having a slotted bight portion 224. As will be further described below with reference to FIG. 9, the spring member engages with the rigid members to form the clamp and provides the bight portion that permits formation of a passage between the two partitioned regions of the clamped stomach. It can be made of plastic, metal, or any other springy material. An example material is spring tempered titanium.

Figure 10:
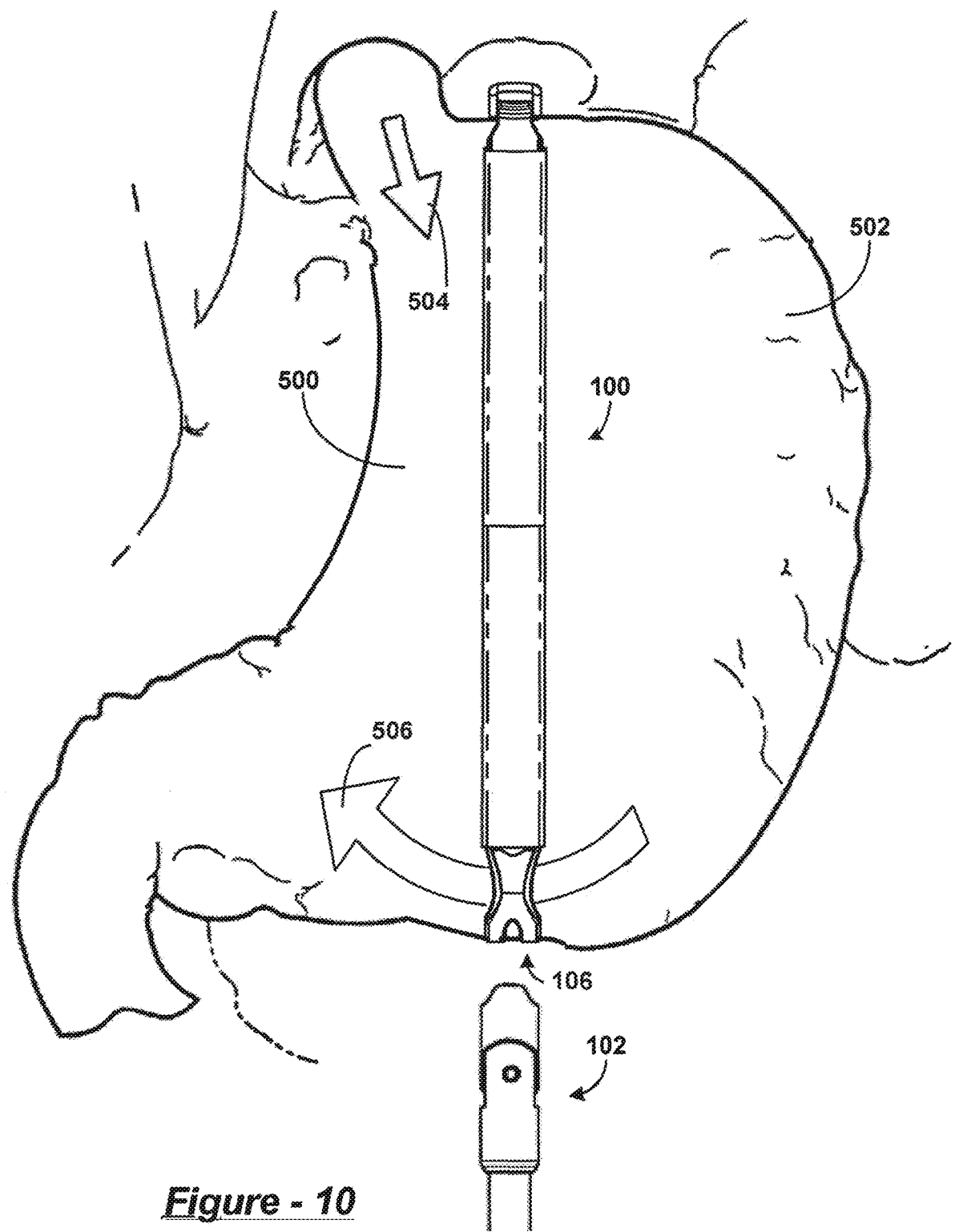
FIG. 10 is a view illustrating the surgical clamp installed in a substantially vertical position on a human stomach.

Turning now to FIG. 9, and referring generally to FIGS. 9A-9D, the three-piece clamp can be assembled by engaging the rigid members 212 and 216 to the spring member 222. For example, the rigid members can be welded or coupled to arms of spring member at various locations 226. In one embodiment, the rigid members 212 and 216 can be attached to interior surfaces of the arms of spring member 222, with the loop 220 arranged to hinge towards and engage the male clasp end 214 of the distal end of rigid member 212. Thus, the rigid members 212 and 216 are employed to form a partition, while the spring member 222 forms a passage between the partitioned regions of an organ or body as shown in FIG. 10. These rigid members 212 and 216 may be of non-uniform thickness to accommodate gradual closing of the clamp from the proximal end towards the distal end in such a manner that a non-uniform thickness of an organ, such as walls of a stomach, can be clamped without injury. Alternatively or additionally, sleeves of padding material can be slid over the arms of the clamp, and the padding material can be of non-uniform thickness as desired. It is envisioned that rigid members 212 and 216 and padding material of varying lengths, contours, and thicknesses may be provided to accommodate needs of different patients as desired.

Turning now to FIG. 10, some embodiments of the surgical clamp installation tool can be used to install the clamp 100 within an abdominal cavity in order to perform bariatric surgery. In particular, the clamp can be positioned, closed, and latched to partition the stomach into a small vertical portion or pouch 500 and an excluded section 502. The vertical pouch 500 receives food at 504, but the food is not able to enter the excluded section 502. Using the installation tool 102(or 202) to engage with the bight portion 106 of the clamp 100, the clamp 100 may be installed in a substantially vertical position on the stomach in one embodiment. That is, if the human patient having the clamp 100 installed were to stand upright, the longitudinal axis of the clamp 100 would be substantially parallel to the gravity vector. Thus, a passage forming section formed in the bottom of the stomach by the clamp allows gastric juices to flow at 506 from the excluded section 502 into the vertical pouch 500.

Figure 11:
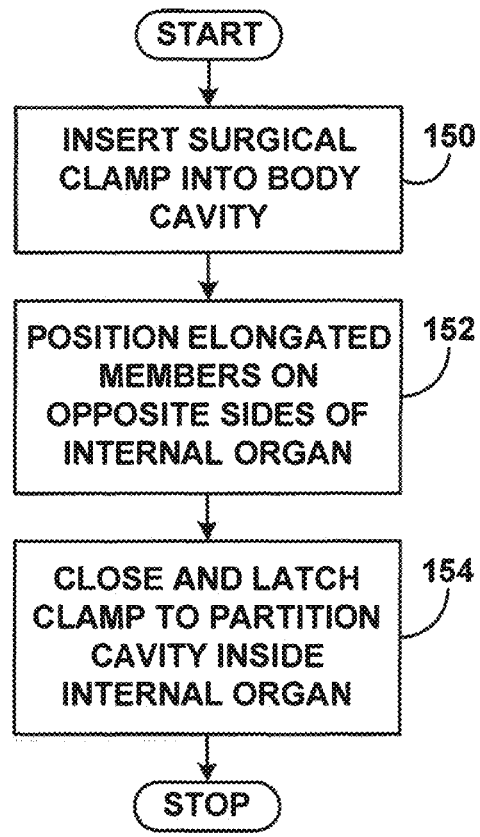
FIG. 11 is a flow diagram illustrating an embodiment of a method for clamping an internal organ.

Turning to FIG. 11, a method for clamping an internal organ can include inserting a surgical clamp through an opening into a body of a living organism at block 150. Then the two elongated members of the surgical clamp are positioned on opposite sides of an internal organ of the living organism at block 152. At block 154, closing and latching the surgical clamp to partition a cavity inside the internal organ includes clamping the exterior of the internal organ with the two elongated members.

As mentioned above, the internal organ can be a human stomach. In this case, closing and latching the clamp can include installing the clamp in a substantially vertical or angled position with a passage forming section of the clamp located towards a bottom of the stomach. This positioning can create a small, vertical stomach pouch and thereby limit the intake of food into an excluded section or portion of the stomach, but still allow gastric juices from the excluded portion of the stomach to flow into the vertical stomach pouch. This partitioning can alter the production of hormones, enzymes and chemicals that affect metabolism, energy levels, hunger, digestion, and absorption of nutrients that are affected by exclusion of gastric fundus and body of the stomach by the partitioning. Sheathing the elongated members of the clamp in silicone padding material along a majority of their length is intended to reduce trauma and/or necrosis of the stomach or other internal organ and enable successful reversal of the surgery. Thus, the method can further include reversing the surgery by removing the clamp.

Inserting the surgical clamp can include performing natural orifice transluminal endoscopic surgery (NOTES). Alternatively, or additionally, it can include performing a combination of NOTES and an assistant trocar placed into an abdominal cavity. This combination can include two or more of a conventional, laparoscopic, NOTES, and one port technique. The NOTES technique can include at least one of transgastric, transvaginal, transrectal, transcolonic, or combinations thereof. The one port technique is used for the introduction of several instruments, and encompasses a one port abdominal (including umbilical), perineal, retroperitoneal approaches, or combinations thereof.

Figure 12:
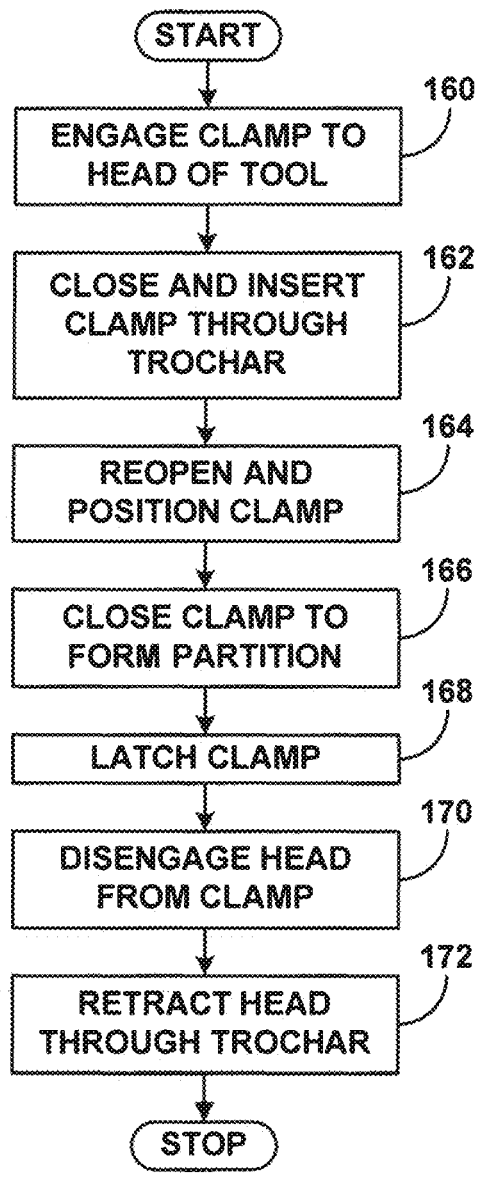
FIG. 12 is a flow diagram illustrating another embodiment of a method for clamping an internal organ.

Turning to FIG. 12, a method for clamping an internal organ can include engaging a surgical clamp to a head of a surgical clamp installation tool at block 160. At block 162, the surgical clamp installation tool can be employed to close the clamp and insert the clamp through an opening in a body cavity of a living organism. Then the tool can be employed at block 164 to reopen the clamp and to position elongated members of the clamp on opposite sides of an internal organ within the body cavity. Next, at block 166, the tool can be employed to close the clamp upon the internal organ and thereby partition a cavity inside the internal organ. The limbs, arms, or elongated members of the clamp close in such a fashion as causing a gradual diminishing space between the two limbs, as the space opening extends proximally, accounting for the different thickness of the stomach. The clamp closes in a fashion that exerts enough pressure to maintain the opposite walls closed to each other without creating damage/trauma/ischemia to the stomach or other organ walls themselves. Then at block 168, the clamp can be latched to fix it in position to partition the internal organ and the cavity inside the internal organ. Also, at block 170, the clamp can be disengaged from the head of the surgical clamp installation tool, and the tool can be retracted from the body cavity at block 172. It is envisioned that the clamp may be configured to latch automatically when the clamp is fully closed. Alternatively, the tool may first be disengaged and removed, and the clamp subsequently latched using an additional tool. Moreover, additional steps may be employed to secure the clamp in place, such as using sutures.

As already described above, padding material can be employed on surfaces of the elongated members of the surgical clamp to reduce damage to the internal organ that would prevent reversal of the surgical procedure. In other embodiments, the thickness or surface contour of the elongated members or arms of the surgical clamp may be provided to align with the particular organ or body being clamped so as to provide the desired pressure or force at each location of the organ or body being clamped. Additionally, engaging the surgical clamp to the head of the surgical clamp installation tool may include passing a T-bar adjacent the end of a pull rod of the installation tool through a slotted aperture formed in a bight portion of the clamp, and rotating the T-bar using a lever or dial. Also, employing the surgical clamp installation tool to close and reopen the clamp may include operating a lever or trigger on a handle of the installation tool to pull and release the pull rod. Further, employing the surgical clamp installation tool to position the elongated members of the surgical clamp may include manipulating a dial on a handle of the installation tool to articulate the head from side to side in a desired plane(s).

Figure 13:
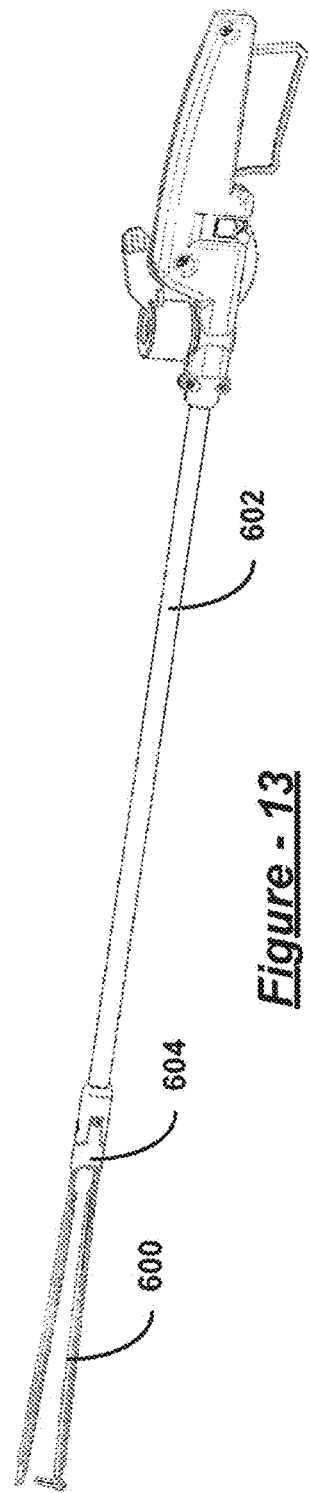
FIG. 13 is a view of yet another embodiment of a surgical clamp engaged with yet another embodiment of a surgical clamp installation tool having an articulating head.

Turning now to FIG. 13, another embodiment of a surgical clamp 600 and surgical installation tool 602 is similar in structure and function to those embodiments described above. One notable difference from the embodiments previously described is that the articulating head 604 of the surgical installation tool 602 is keyed with a curvature or radius configured to hold the clamp 600 securely in place while permitting the clamp 600 to remain in an open position. This configuration permits a surgeon holding the installation tool 602 in one hand to hold the clamp 600 securely in the articulating head 604 of the tool 602 while pressing the distal ends of the clamp 600 together with the other end for entry to a trocar. Once the distal ends of the clamp 600 have entered the trocar, the trocar then holds the ends shut, and permitting the surgeon free use of the other hand. Upon entry to the abdominal cavity, the clamp naturally springs open for engagement with a bodily organ, such as the stomach, and the surgeon can articulate the head from side to side while it is held securely in the head 604 while still in the open position. Once in position, the surgeon can close the clamp using sutures and/or by applying pressure externally or internally using other surgical tools. Thus, in this particular embodiment, the installation tool 602 may not be employed to close the clamp on an internal organ of the patient, but may be employed to hold, insert, and articulate the clamp into position.

Figure 14:
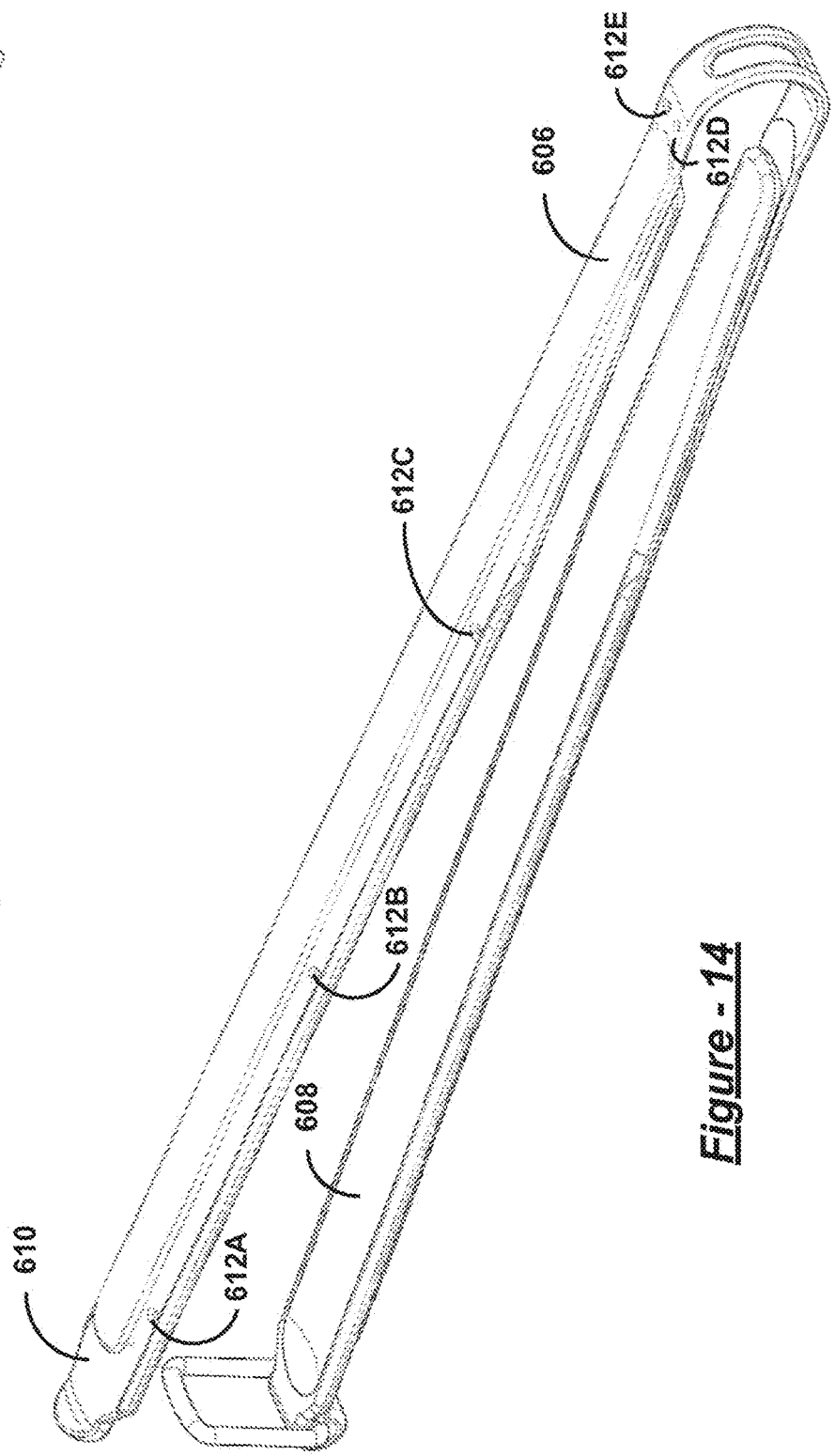
FIG. 14 is a perspective view of the surgical clamp of FIG. 13.
Figure 15A:
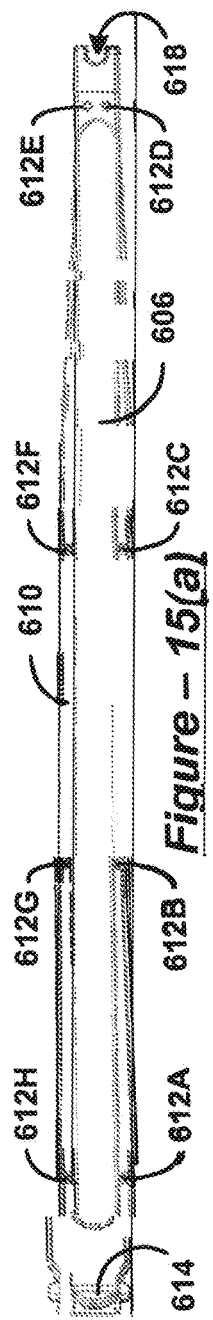
FIG. 15(a) is a top view of the surgical clamp of FIG. 14.
Figure 15B:
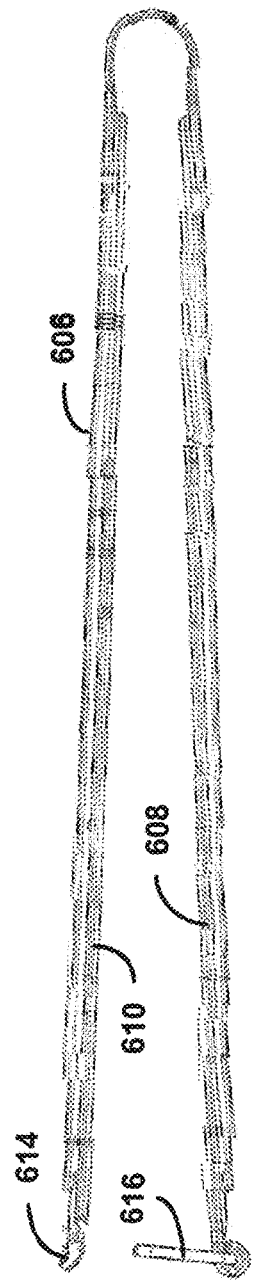
FIG. 15(b) is a left view of the surgical clamp of FIG. 14.
Figure 15C:
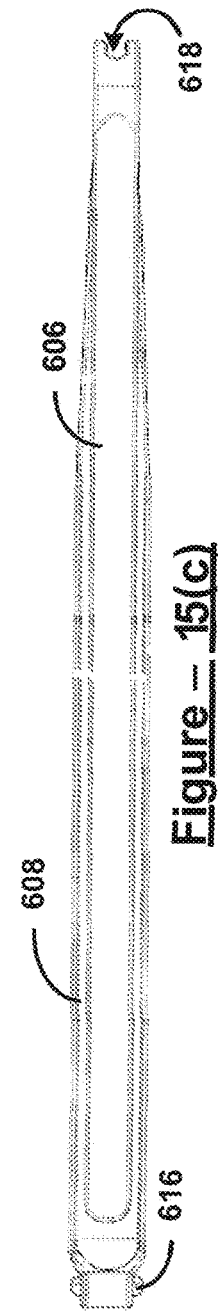
FIG. 15(c) is a bottom view of the surgical clamp of FIG. 14.
Figure 15D:
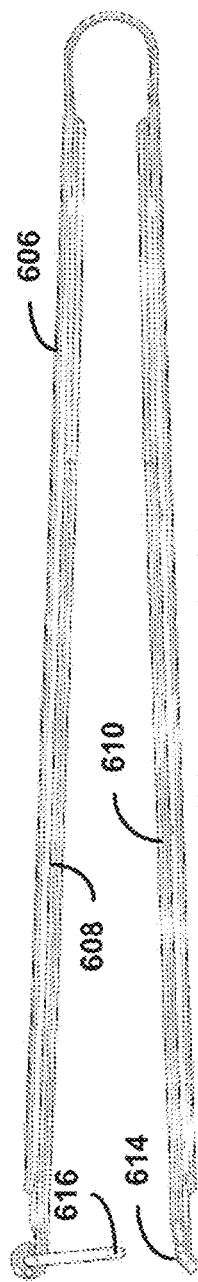
FIG. 15(d) is a right view of the surgical clamp of FIG. 14.
Figure 15F:
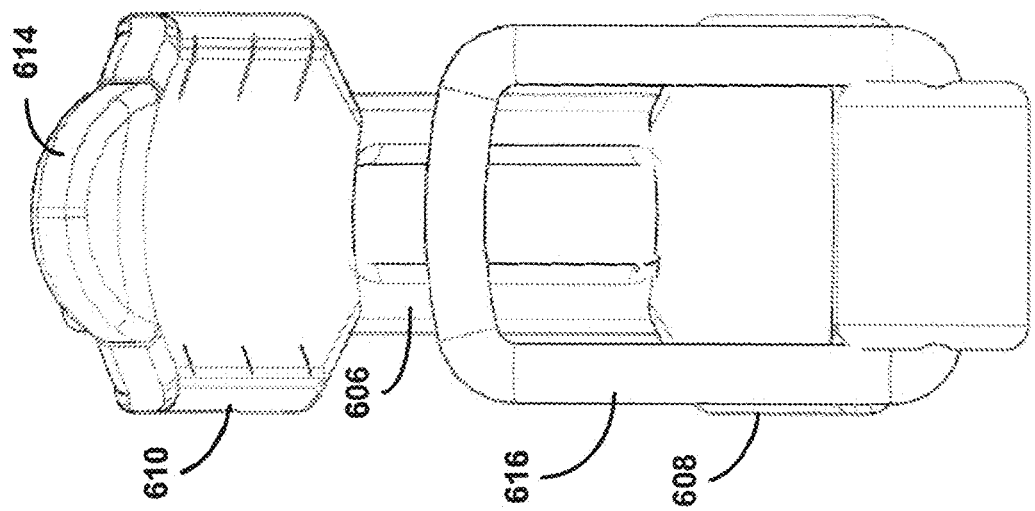
FIG. 15(f) is a distal latch end on view of the surgical clamp of FIG. 14.
Figure 15E:
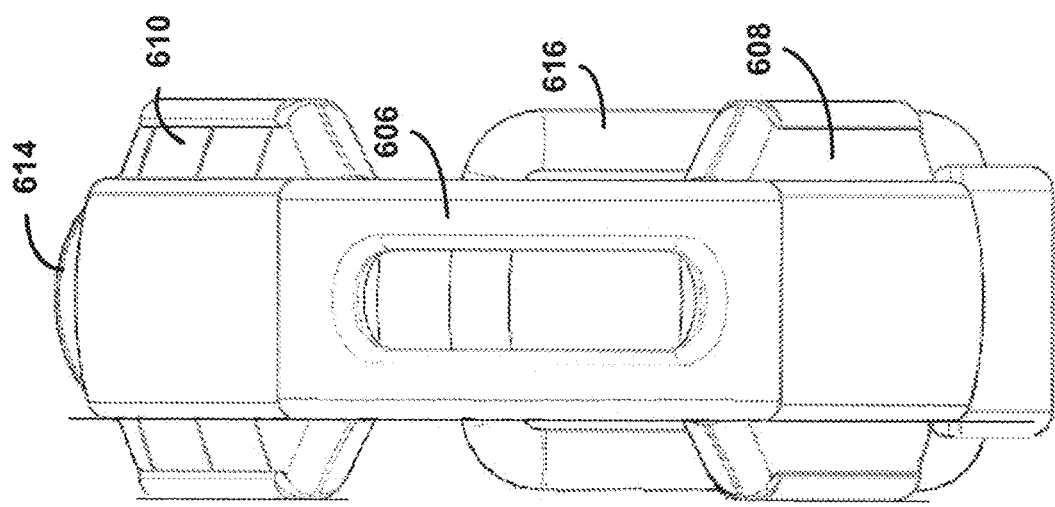
FIG. 15(e) is a proximal spring end on view of the surgical clamp of FIG. 14.

Referring now to FIG. 14, clamp 600 can have a three piece design similar to that described above. In other words, it can have a spring member 606 that is comprised predominantly of spring steel, and that is engaged with lower and upper rigid members 608 and 610. These rigid members 608 and 610 can be comprised primarily of titanium, and they can have a concavity that increases their rigidity. In addition, suture holes 612A-612E can be provided in upper rigid member 610, as well as in an upper portion of spring member 606. A surgeon can employ these suture holes 612 to secure the clamp 600 in place on a stomach or other bodily organ. It is envisioned that additional or alternative suture holes 612 can be provided, such as in lower rigid member 608 and lower portion of spring member 606, and that positions of the suture holes 612 can be different from those shown. However, as will be more fully described below with reference to FIGS. 19-27, the placement of suture holes in the upper rigid member 608 and upper portion of spring member 606 can permit suturing of the clamp 600 in place prior to application of a silicone sleeve (see FIGS. 19-27) that slides onto the clamp via the un-sutured lower rigid member 608 and lower portion of spring member 606. Yet, once the sleeve is installed, it should be understood that additional suture holes 612 provided in lower rigid member 608 and/or lower portion of spring member 606 may prove useful in a subsequent application of additional sutures.

Turning now to FIGS. 15(a)-15(f) and referring generally thereto, it should be appreciated that a double row of suture holes 612A-612H can be provided in spring member 606 and upper rigid member 610, a distal portion of which can exhibit a male clasp feature 614 positioned to engage a female clasp feature, such as a wire loop 616, of lower rigid member 608. Suture holes 612D and 612E can be positioned on spring member 606 at a location that lies between a position at which upper rigid member 610 is engaged to spring member 606, and a position at which a slot 618 is formed in a bight portion of spring member 606. In the case that the distal end of upper rigid member 610 exhibits a male clasp feature 614, such as a planar curvature away from a plane in which the upper rigid member 610 predominantly lies, a complimentary female clasp feature can be exhibited by a distal end of lower rigid member 608, such as the aforementioned rectangular wire loop 616 engaged by a hinge formation 620 provided in the distal end of lower rigid member 608. It should be readily understood that the same functionality can be achieved if upper rigid member 610 exhibits the female clasp feature, and lower rigid member 608 exhibits male clasp feature 614. Thus, the positions of the clasp features can be reversed in other embodiments.

Figure 16:
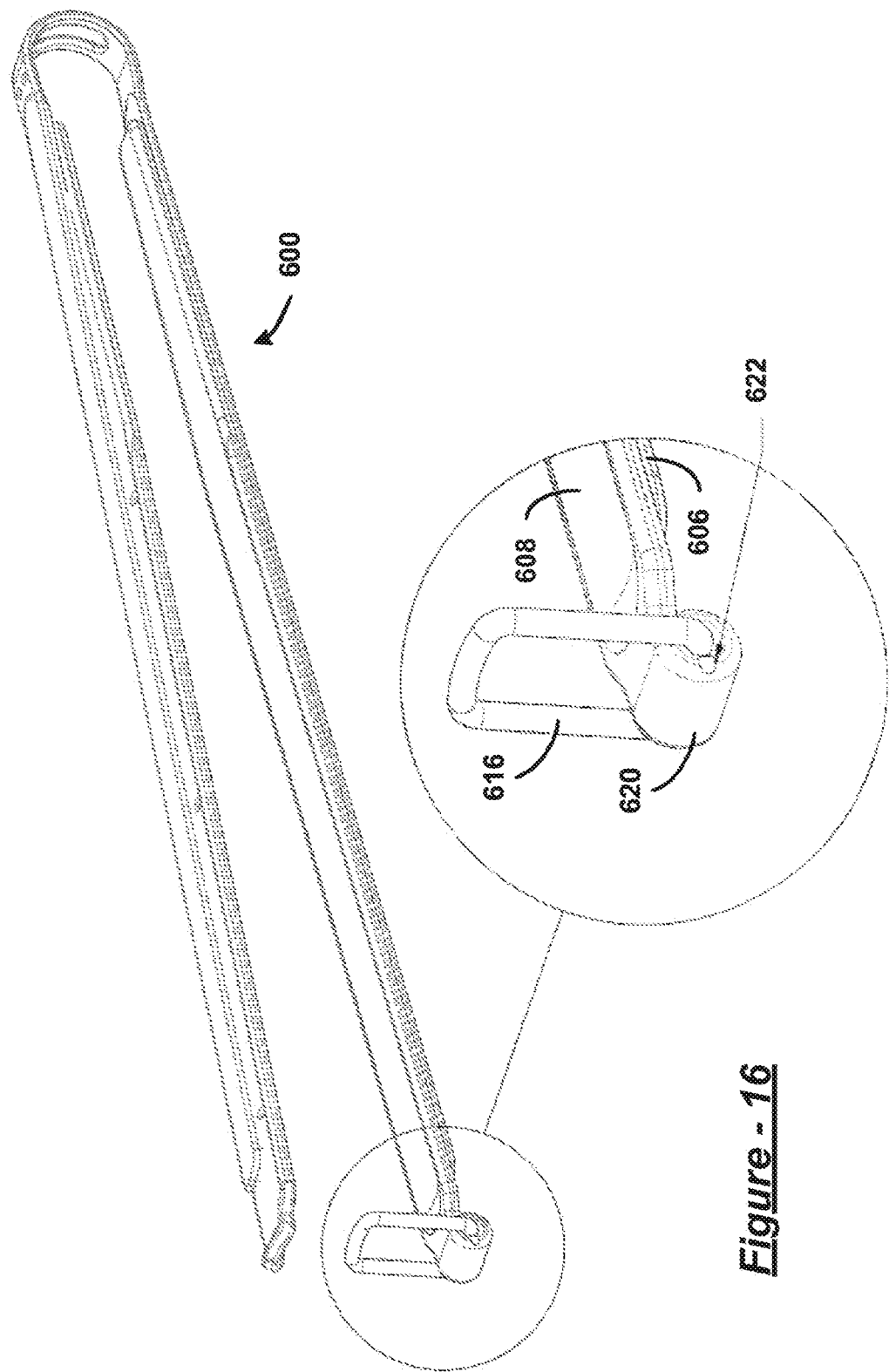
FIG. 16 is a detailed view of a latch end of a bottom arm of the surgical clamp of FIG. 14.
Figure 17A:
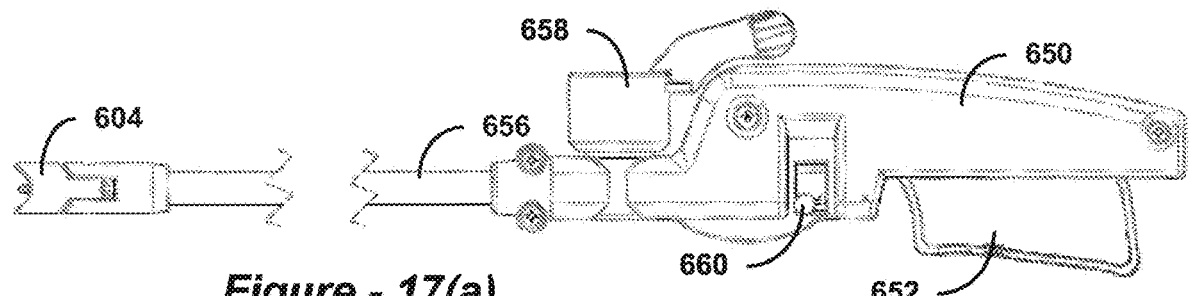
FIG. 17(a) is a top view of the surgical clamp installation tool of FIG. 13.
Figure 17B:
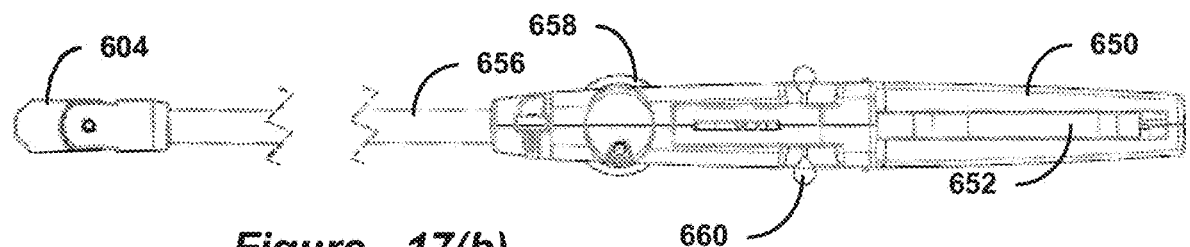
FIG. 17(b) is a left view of the surgical clamp installation tool of FIG. 13.
Figure 17C:
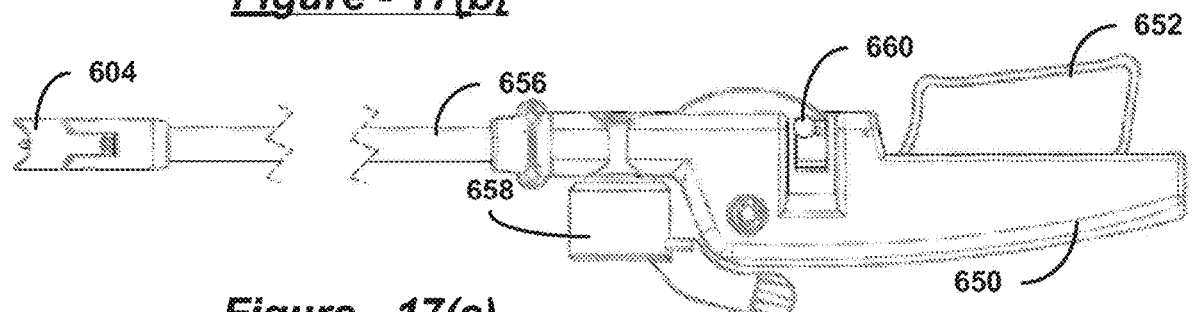
FIG. 17(c) is a bottom view of the surgical clamp installation tool of FIG. 13.
Figure 17D:
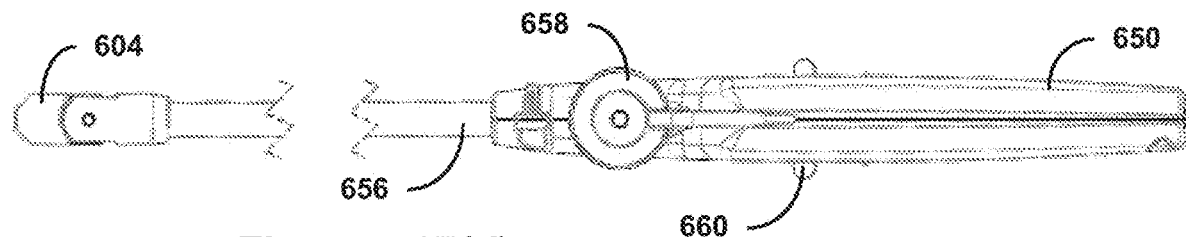
FIG. 17(d) is a right view of the surgical clamp installation tool of FIG. 13.

Turning now to FIG. 16, another additional feature of clamp 600 can be a detent 622 that is formed in hinge formation 620, and that engages wire loop 616 of the female clasp feature. This detent 622 can be positioned on the hinge formation 620 at a location that is most distal when the clamp 600 is held in a closed position, and it can be sized and shaped to hold the wire loop 616 in a lowered position at which the loop 616 lies in a plane parallel to a plane in which lower rigid member 608 predominantly lies. A similar or identical detent (not shown) can be provided on an opposite side of hinge formation 620, and it can be similarly distally positioned to assist in holding the wire loop 616 in the aforementioned lowered position. This lowered position allows the clamp 600 to be inserted through a trocar and guided to enclose a bodily organ, such as a stomach, at which point the aforementioned silicone sleeve (see FIGS. 19-27) can be partially applied. Then, before the silicone sleeve is fully engaged to the clamp 600, wire loop 616 can be forced out of detent 622 into a raised position at which it engages the male clasp feature 614 of the clamp 600.

Before raising the wire loop 616, it is envisioned that the clamp 600 can be pressed into a closed position by use of two or more graspers inserted into the abdominal cavity through additional trocars (i.e., multiport technique). Then, a suture tag pre-applied to wire loop 616 can be used to force wire loop 616 out of detent 622 into the raised position, resulting in the wire loop 616 engaging the male clasp feature 614 and holding the clamp 600 in the closed position without assistance from the two or more graspers. Alternatively or additionally, it is envisioned that closing and latching of the clamp 600 can be achieved by utilizing any suitable endoscopic surgical tools and techniques as will be readily apparent to one skilled in the art from the present disclosure.

Turning now to FIGS. 17(a)-17(f) and referring generally thereto, an endoscopic surgical installation tool for engaging and manipulating the clamp can be similar to those described above. For example, the installation tool can have a handle 650, trigger 652, pull rod, T-bar 654, cylindrical tube 656, dial 658 (e.g., with thumb lever), hub, guidelines, and articulating head 604 that are identical or similar to those described above. However, as previously described, a curvature or incline imparted to the head 604 by wedges of the head 604 can be keyed to a bight portion of the previously described clamp so as to hold the clamp in a fully open or predominantly open position when T-bar 654 has been fully retracted by actuation of trigger 652. Additionally, a latch release 660 can be provided that can extend from both sides of handle 650 for ergonomic, ambidextrous operation.

Figure 18:
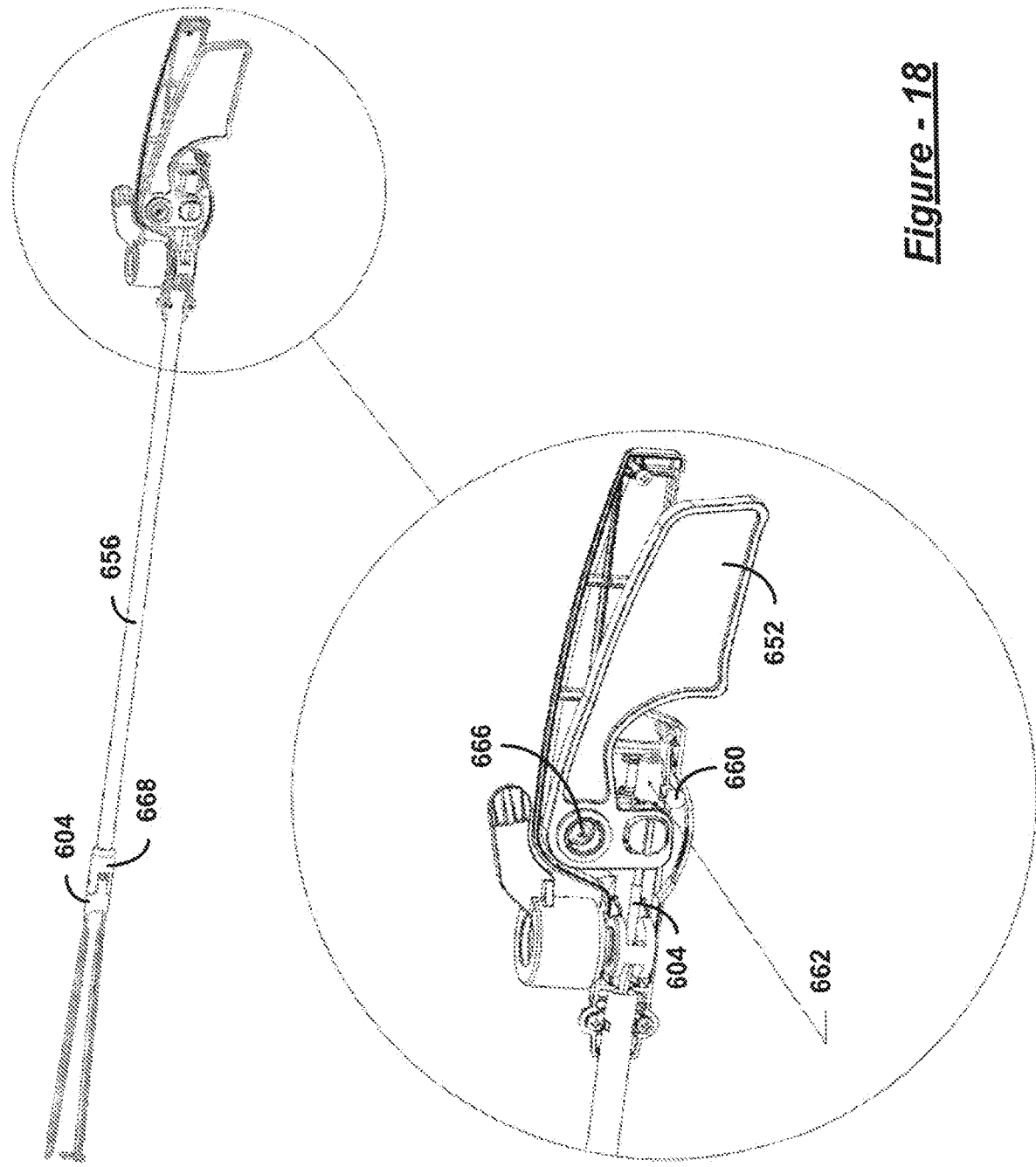
FIG. 18 is a detailed left side view of a handle end of the surgical clamp installation tool FIG. 13 in which the left side of the handle housing is shown removed.

Turning now to FIG. 18, the latch release 660 can have a hinged plate with a retention spring that forces the latch release 660 upwards to engage a latch 662 provided at a proximal end of pull rod 664. In use, a surgeon can engage the T-bar to the clamp 600 by rotating the clamp 600 and/or installation tool in a common longitudinal axis until the T-bar fits through the notch in the bight portion of the clamp 600, and then rotating the clamp 600 and/or installation tool an integer multiple of ninety degrees until a length direction of the T-Bar is perpendicular to a length direction of the notch. Then, actuation of trigger 652 can retract pull rod until opposing latch surfaces (e.g., edges, extensions, faces, flanges, gouges, hooks, inclines, ledges, lips, notches, overhangs, projections, protrusions, ribs, ridges, skirts, serrations, slits, slots, teeth, wedges, and combinations thereof) of the latch 662 and release 660 can catch and hold the pull rod 664 in a fully retracted or predominantly retracted position.

Once the latch 662 is engaged, the clamp 600 is ready to be inserted into an inflated abdominal cavity through a trocar as described above, and a seal provided between cylindrical tube 656 and clevis 668 can prevent out gassing from the abdominal cavity through the head 604 and/or cylindrical tube 656. Alternatively, the seal can be provided anywhere inside cylindrical tube 656. In some embodiments, the seal is achieved by using a circular silicone die having a slit and a hole in the middle, with the pull rod 664 threaded through the hole.

Once the clamp 600 is in position within the abdominal cavity to enclose and partition the stomach or other organ, pressing down on latch release 660 can permit automatic extension of pull rod 664 by action of a torsion spring provided to trigger screw 666 to force de-actuation of trigger 652. The T-bar can then be disengaged from the clamp by rotating the installation tool along its longitudinal axis an integer multiple of ninety degrees and removing it from the trocar. Thus, it should be apparent that, in some embodiments, the pull rod may not be configured to rotate as in alternative embodiments described above, but only to retract and to extend.

Figure 19:
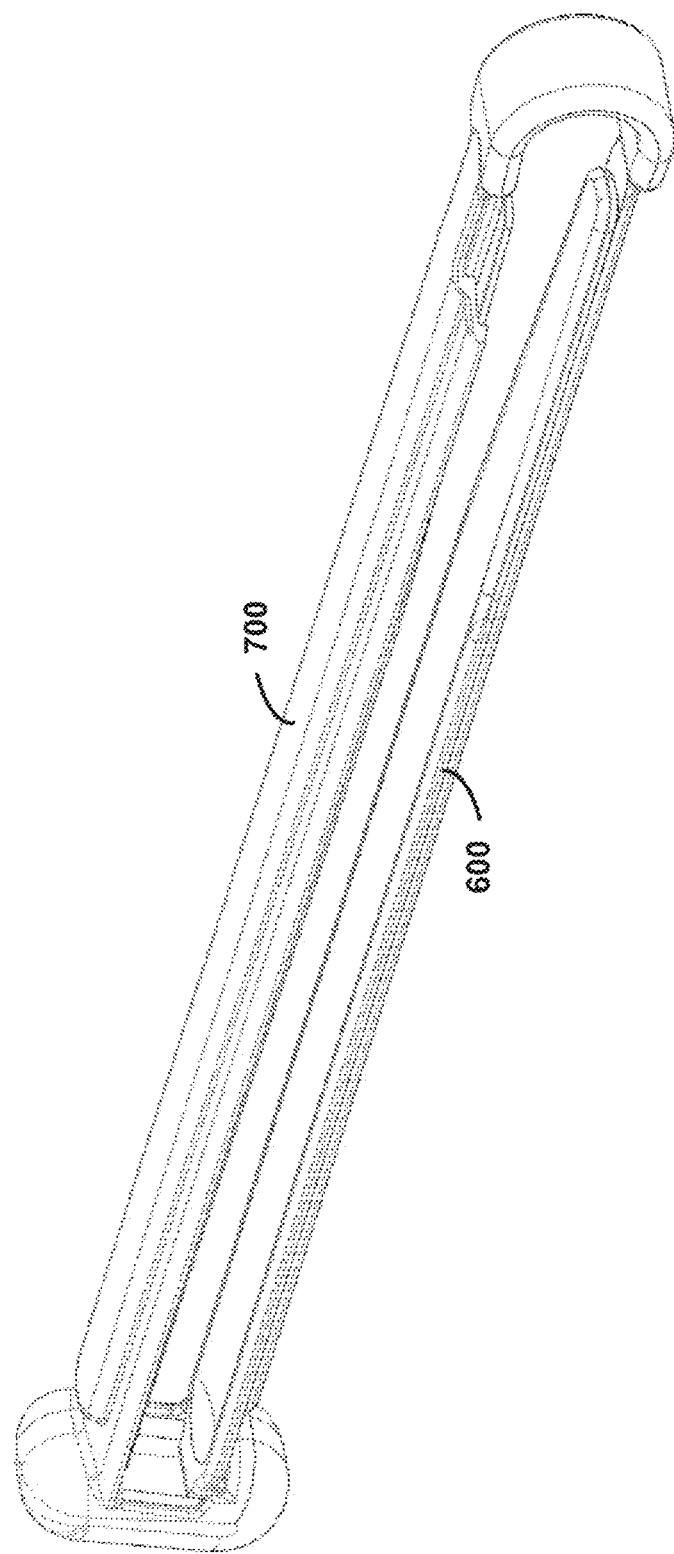
FIG. 19 is a perspective view of the surgical clamp of FIG. 14 having a silicone sleeve engaged therewith.
Figure 20:
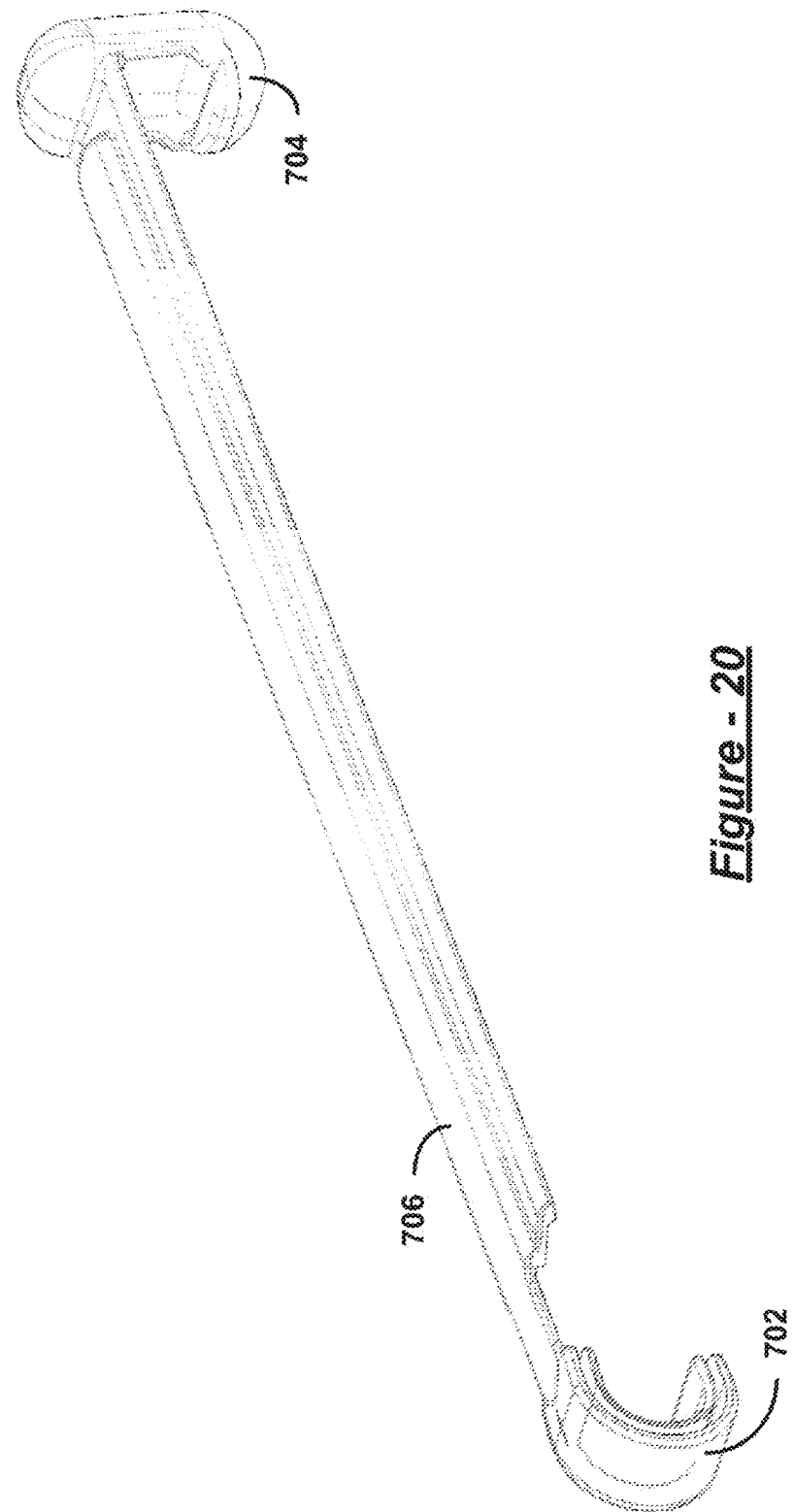
FIG. 20 is a perspective view of the silicone sleeve of FIG. 19 in a disengaged state.
Figure 21:
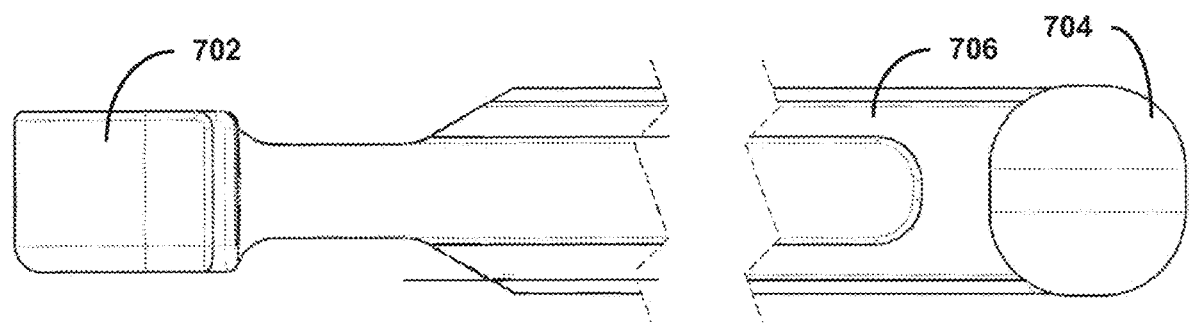
FIG. 21 is a bottom view of the silicone sleeve of FIG. 20.
Figure 22:
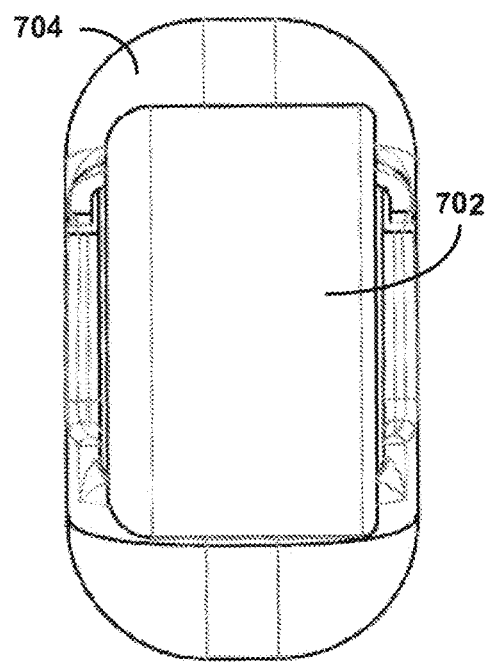
FIG. 22 is a proximal end-on view of the silicone sleeve of FIG. 20.

Turning now to FIG. 19, a silicone sleeve 700 can be configured to engage clamp 600. In some embodiments, silicone sleeve 700 can be formed to cover primarily an upper arm and both ends of clamp 600. This silicone sleeve 700 can be used as padding to protect surrounding organs from irritation or damage. Thickness of the silicone can be varied for different applications, such as partitioning an organ, stomach, or vessel.

Turning now to FIGS. 20-27 and referring generally thereto, the silicone sleeve 700 can have tubular section 702 at a proximal end that slides onto the lower arm of clamp and can be manipulated into position to encapsulate the previously described bight portion of the clamp. The clamp can then be closed and latched as described above. Presuming that the upper arm of the clamp has already been sutured to the organ, stomach, or vessel, a distal end of the sleeve 700 can then be engaged to encapsulate the distal end of the clamp. For this purpose, the distal end of the sleeve 700 can be configured as a latch cap 704 that is form fitted to the closed latch features (see FIG. 25). A padding strip 706 situated between the tubular section 702 and latch cap 704 can be sized to a length of the clamp so as to be stretched taught across the upper arm of the clamp once the sleeve 700 is installed. A slot engaging feature 708 formed inside of tubular section 702 can be provided to engage with the previously described slot in the bight portion of the clamp by plugging the slot, and thus hold the tubular section of the sleeve 700 in place on the bight portion of the clamp.

Figure 28:
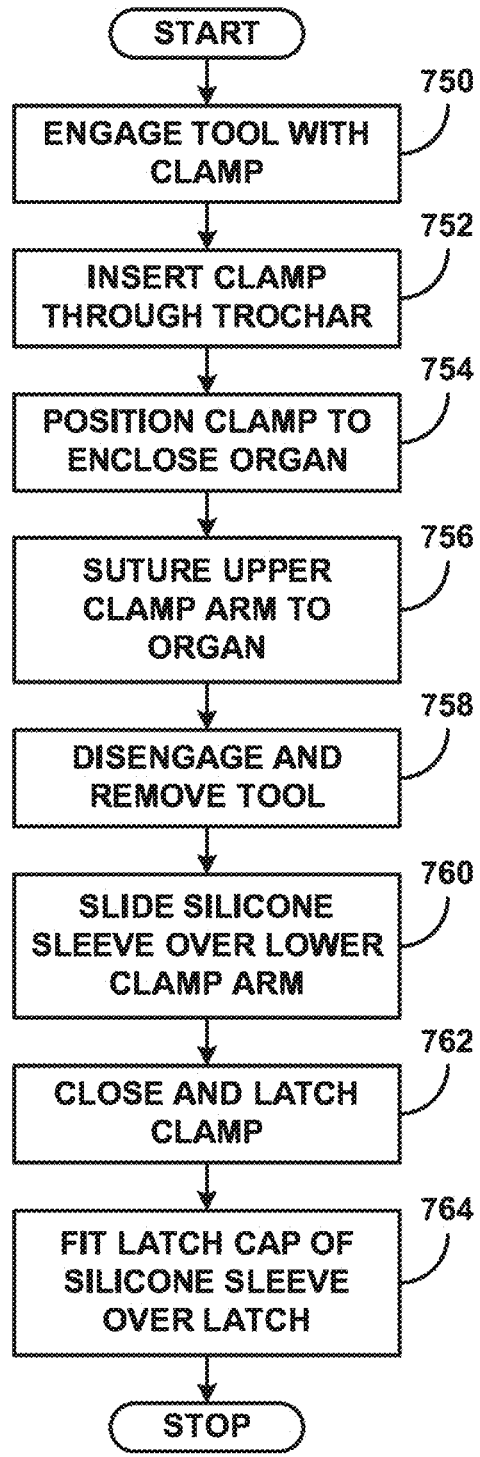
FIG. 28 is a flow diagram illustrating a method of performing endoscopic surgery utilizing the silicone sleeve, clamp, and installation tool of FIGS. 13-27.

Turning now to FIG. 28, a method of performing surgery can begin at step 750 by engaging the previously described clamp to the previously described surgical installation tool in one or more of the previously described manners. Thereafter, the clamp can be inserted through a trocar at step 752, and positioned to enclose an organ (e.g., stomach, vessel, etc.) at step 754. Next, at step 756, an upper arm of the clamp can be sutured to the organ though suture holes supplied in the clamp as previously described, and the installation tool can be disengaged and removed from the trocar at step 758. Thereafter, the previously described silicone sleeve can be slid over a lower arm of the clamp at step 760 as previously described, and the clamp can be closed and latched at step 762. Finally, at step 764, a latch cap of the silicone sleeve can be fit over the latch of the clamp, and additional sutures can be applied if desired. It should be understood that the sequence of the aforementioned steps can vary in additional or alternative embodiments, and that additional or alternative steps can be employed as will be readily apparent to one skilled in the art.

FIGS. 29-40 and the accompanying description disclose various embodiments of a surgical clamp overmolded in a polymer material. The surgical clamp is, in one implementation, a laparoscopically implanted device which, when closed and latched or secured, partitions a patient's stomach into two sections, such as two vertical sections or other divisions. The clamp may be installed using standard surgical tools (e.g., clamps, scissors, etc.) and/or, in some embodiments, an installation tool, such as one of the installation tools discussed herein. When the clamp is installed, in one installation, the lesser curvature segment of the stomach forms the Magenstrasse, and the greater curvature segment, including the fundus, is generally excluded from nutritional contact. In one implementation, the clamp includes, at a proximal end, an aperture with an enlarged radius (generally referred to hereafter as the bight portion or passage-forming section), by which gastric juices created by the fundus and the body can empty into the atrum. By excluding the fundus, the clamp may alter or reduce hormones such as, for example, ghrelin, leading to the patient's loss of hunger. Additionally, the clamp acts as a restrictive procedure by reducing the size of the Magenstrasse by creating a small lumen for a vertical passageway of the nutrients along the lesser curvature.

Figure 29:
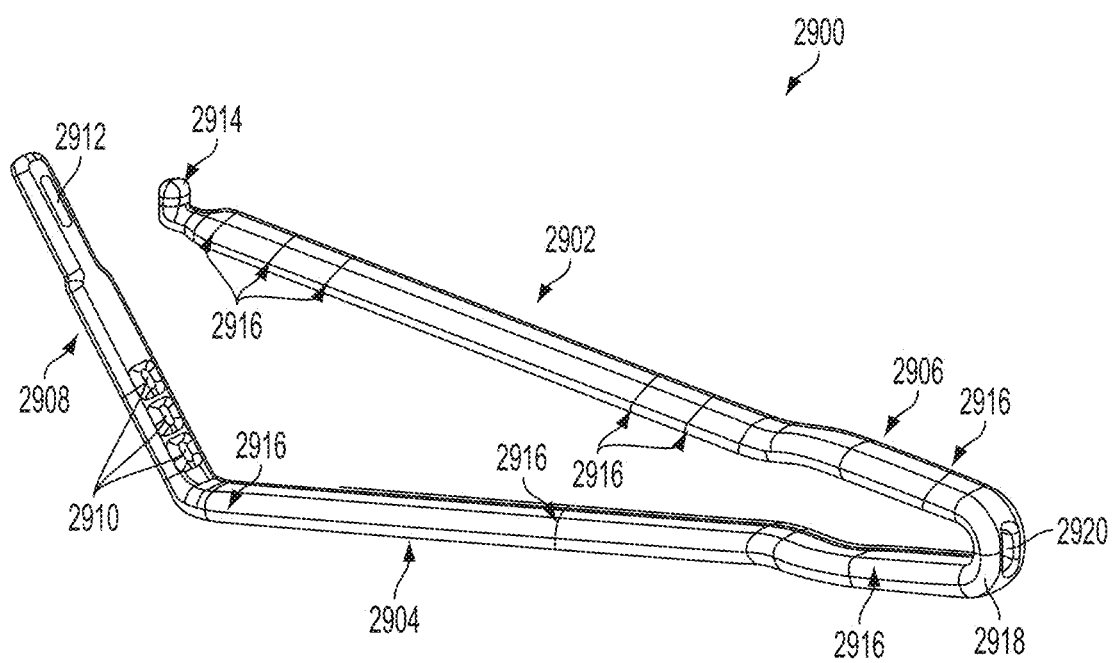
FIG. 29 is a perspective view of an embodiment of a one-piece surgical clamp comprised of first and second substrate members overmolded in a polymer material.
Figure 30A:
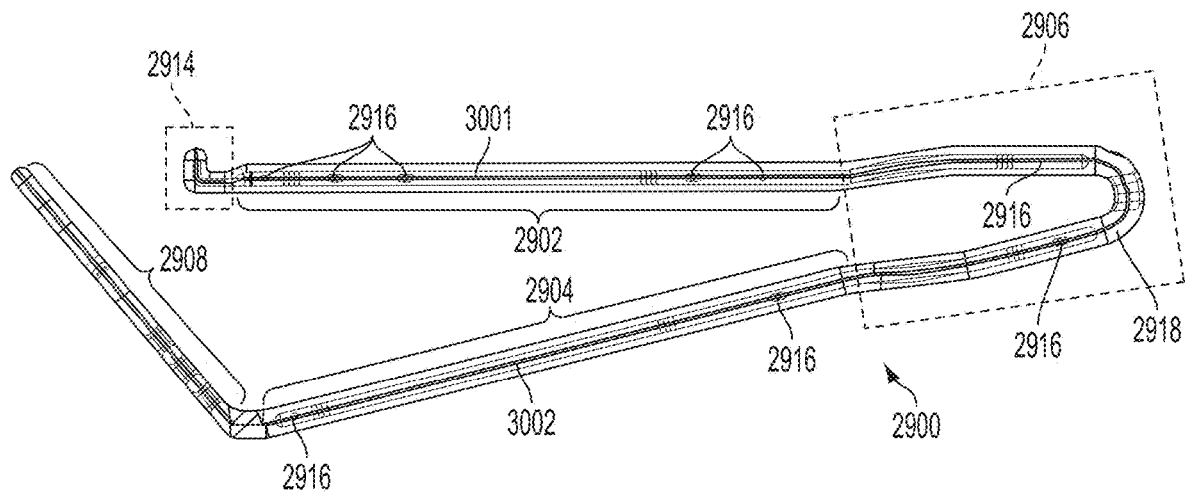
FIGS. 30(a) and 30(b) illustrate respective side and perspective views of the one-piece surgical clamp of FIG. 29, wherein the polymer material is illustrated semitransparent to show the first and second substrate members.
Figure 30B:
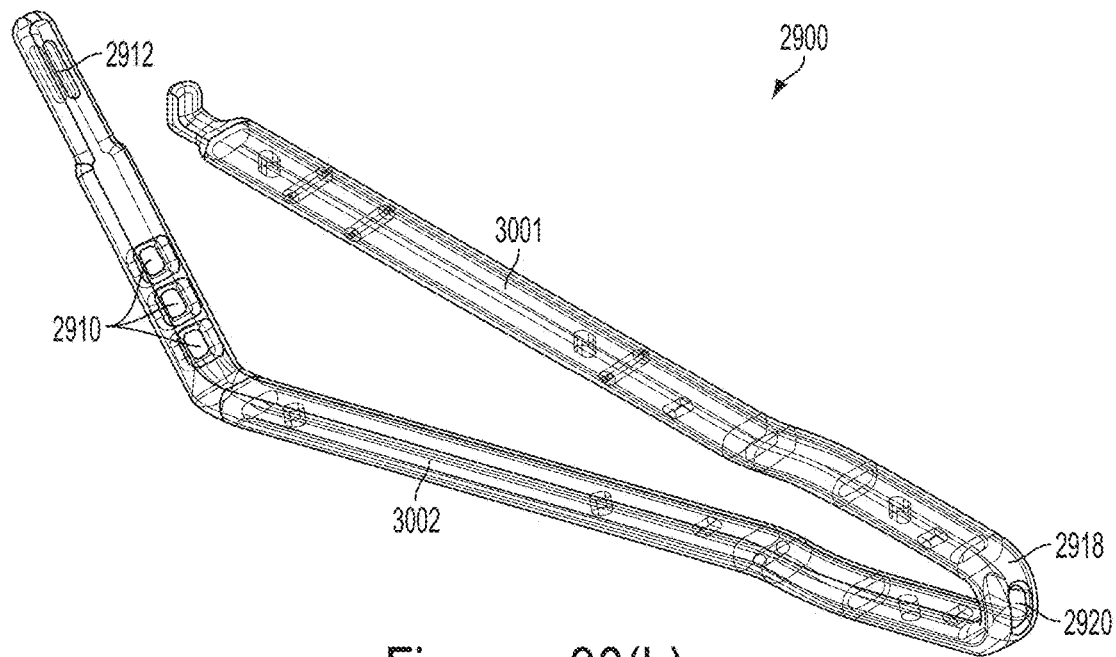
Figure 31A:
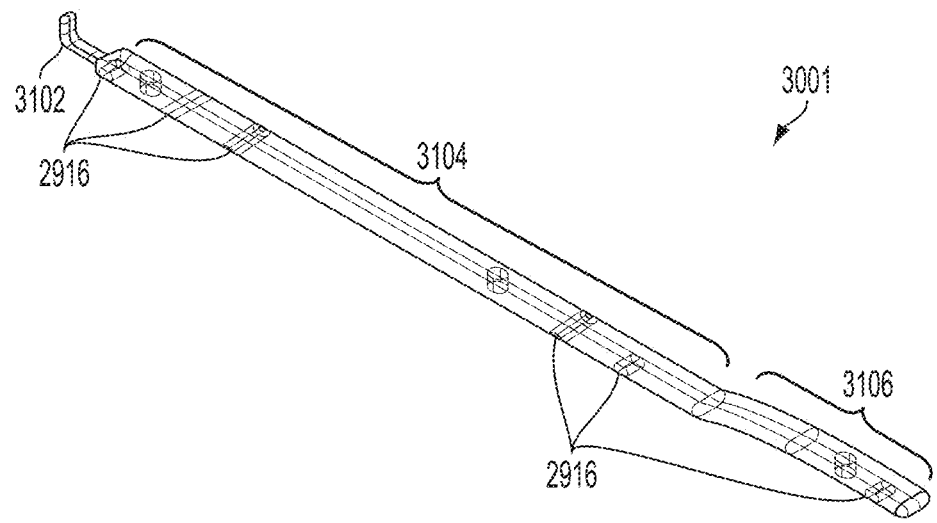
FIGS. 31(a) and 31(b) illustrate the respective first and second substrate members of the one-piece surgical clamp of FIG. 29.
Figure 31B:
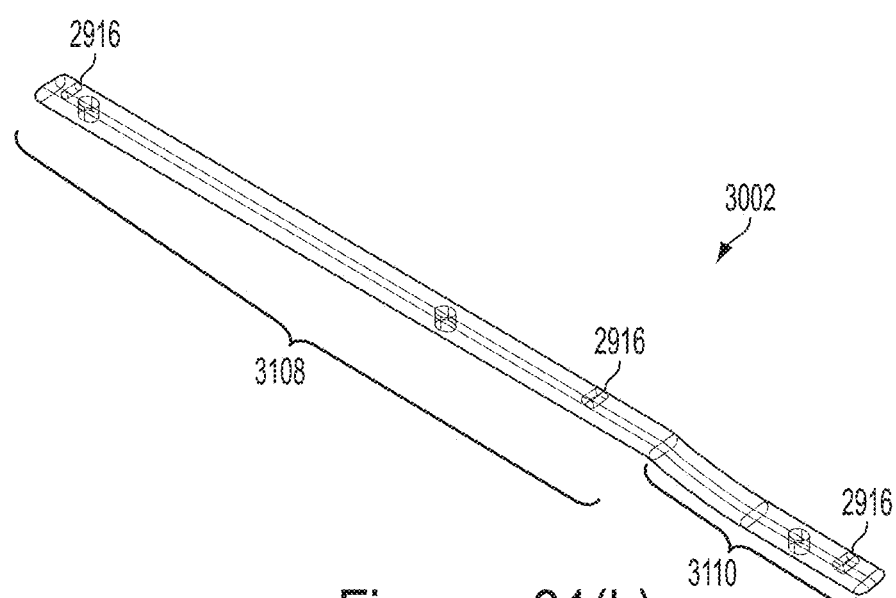

FIG. 29 illustrates an embodiment, wherein the fully or partially overmolded surgical clamp is of a one-piece design. The one-piece clamp 2900 includes first and second substrate members (shown in FIGS. 30(*a*), 30(*b*), 31(*a*) and 31(*b*)) overmolded in a polymer or elastomer material to form a first elongated portion 2902, a second elongated portion 2904, a bight portion 2906, a fastener portion 2908, and an engagement portion 2914. As mentioned above, the first and second elongated portions 2902 and 2904 serve as a partition-forming section of the clamp 2900. Referring briefly to both FIGS. 29 and 10, when the clamp 2900 is installed within an abdominal cavity, the first and second elongated portions 2902 and 2904 are engaged to partition the stomach into a small, vertical pouch 500 and an excluded section 502. The bight portion 2906 comprises a passage-forming section located towards the proximal end of the clamp 2900. The passage-forming section allows gastric juices to flow 506 from the excluded section 502 into the vertical pouch 500.

In accordance with the present disclosure, the term overmolded is intended to describe a product wherein underlying substrate material(s) are substantially fully or partially encapsulated, covered, or coated with one or more layers of one or more overlying materials. For example, in accordance with the embodiment illustrated in FIG. 29, the first and second substrate members comprise the underlying substrate materials, and the overlying polymer or elastomer material comprises the overmolded material, or overmolding. In some embodiments, the overmolding may be of a non-uniform thickness or durometer, or positioned in certain areas, to produce various portions or features (such as a fastener portion, flexible hinge, etc.) and/or to accommodate gradual closing of the clamp from the proximal end towards the distal end in such a manner that a non-uniform thickness of an organ, such as walls of a stomach, can be appropriately clamped without injury. In some embodiments, the overmolded polymer material may comprise silicone such as, for example, an unrestricted implant-grade silicone. In some embodiments, the substrate material may comprise the same material as the overmolding. Additionally, in some embodiments, the substrate material(s) and overmolding material(s) may comprise different or varying materials and/or durometers.

As shown in FIG. 29, the first and second elongated portions 2902 and 2904 are joined by the bight portion 2906 at the proximal end of the clamp 2900. The bight portion 2906 includes a flexible hinge 2918 formed, in one implementation, from the polymer overmold, wherein the flexible hinge 2918 permits expansion and movement of the bight portion 2906 to accommodate any irregularities in the stomach wall or fluctuations of the passage-forming section when the clamp 2900 is installed. The flexible hinge 2918 also allows the clamp 2900 to accommodate variations in stomach thicknesses without compromising the pressure applied by the clamp 2900, particularly in the partition-forming section. In some embodiments, the flexible hinge 2918 includes one or more attachment features such as, for example, a slotted aperture 2920. The attachment feature may allow the clamp 2900 to be engaged with an installation tool (for example, such as the installation tool shown in FIG. 33) in accordance with the foregoing disclosure. In still other embodiments, the flexible hinge 2918 may be provided at a desired durometer or elasticity that may be the same as or different from that of the polymer or silicone overmolded portions provided in other areas of the clamp 2900, such as the first and second elongated portions 2902 and 2904.

When installing the surgical clamp 2900, the clamp 2900 is placed into position as explained in greater detail below, and the fastener portion 2908 and engagement portion 2914 are used to retain the clamp 2900 in a substantially closed position. In the embodiment illustrated in FIG. 29, the fastener portion 2908 comprises a strap formed from the overmolded polymer or other material and located towards the distal end of the second elongated portion 2904. The strap may include one or more primary openings 2910 for receiving the engagement portion 2914, and a secondary opening 2912 used for adjusting or manipulating the fastener portion 2908 and/or the second elongated portion 2904. For example, a surgeon may use a tool (not shown) to engage the secondary opening 2912 to position the strap such that the engagement portion 2914 engages one of the primary openings 2910. In the embodiment illustrated in FIG. 29, the engagement portion 2914 comprises a protrusion, such as a hook or tab, for engaging openings of the fastener portion 2908.

In some embodiments, the clamp 2900 may be adjusted by disengaging the engagement portion 2914 from one of the primary openings 2910, and engaging the engagement portion 2914 with another one of the primary openings 2910 to either increase or decrease the spacing between the first and second elongated portions 2902 and 2904. In some embodiments, the fastener portion 2908 may be sutured to the first elongated portion 2902 using suture pass-through holes 2916, such as those located along an outside surface of the first elongated portion 2902. Additionally, in some embodiments, once positioned on the stomach, the suture pass-through holes 2916 may be used to suture the clamp 2900 to the stomach walls to avoid displacement. It should be understood that, in some embodiments, sutures may be placed through the overmolding, as described in greater detail below.

Referring now to FIGS. 30(*a*) and 30(*b*), the surgical clamp 2900 of FIG. 29 is shown from respective side and perspective views, wherein the polymer material is illustrated semitransparent to show the underlying first substrate member 3001 and second substrate member 3002. As shown in FIGS. 30(*a*) and 30(*b*), the first and second substrate members 3001 and 3002 may, in some embodiments, comprise the respective first and second elongated portions 2902 and 2904, as well as at least a part of the bight portion 2906. Additionally, in some embodiments, the first substrate member 3001 may also comprise at least a portion of the engagement feature 2914.

FIGS. 31(*a*) and 31(*b*) illustrate the respective first and second substrate members 3001 and 3002 comprising the one-piece clamp 2900 illustrated in FIGS. 29, 30(*a*) and 30(*b*). In some embodiments, the first and second substrate members 3001 and 3002 each comprise a 3 mm-thick titanium substrate. As shown in FIG. 31(*a*), the first substrate member 3001 may include a tab or a hook 3102 comprising at least a portion of the engagement feature 2914, a first section 3104 comprising a part of the first elongated portion 2902, and a second section 3106 comprising a part of the bight portion 2906. As shown in FIG. 31(*b*), the second substrate member 3002 may include a first section 3108 comprising a part of the second elongated portion 2904 and a second section 3110 comprising a part of the bight portion 2906. It should be understood that the dimensions and materials comprising the substrate members provided herein are merely examples. It is envisioned that the substrate members may be of various thicknesses and lengths, and may be comprised of various biocompatible materials such as titanium or biocompatible polymer resins such as polyether ketone ketone (PEKK) or polyether ether ketone (PEEK).

In accordance with the embodiment illustrated in FIGS. 29, 30(*a*), 30(*b*), 31(*a*) and 31(*b*), the polymer overmolded portion of the clamp 2900 is a 1.5 mm-thick layer of polymer material (e.g., silicone) encapsulating the first and second substrate members 3001 and 3002. The flexible hinge 2918 and fastener portion 2908 are formed from the polymer material, and are approximately 6 mm thick to provide a substantially consistent thickness along the surgical clamp 2900. However, as previously discussed, in some embodiments, the polymer material comprising or overmolding one or more portions of the clamp 2900 may have a non-uniform thickness or application. It should be appreciated that the foregoing dimensions are merely examples and are not intended to limit or define any aspects of the clamp or portions thereof.

Figure 32:
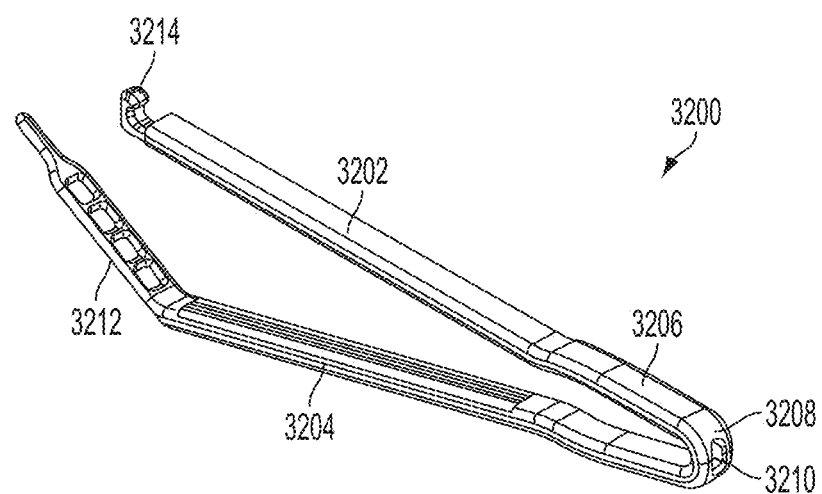
FIG. 32 illustrates another embodiment of a one-piece surgical clamp comprised of first and second substrate members overmolded in a polymer material.

FIG. 32 illustrates another embodiment of a one-piece surgical clamp 3200 comprised of first and second substrate members overmolded in a polymer material. The clamp 3200 includes a first elongated portion 3202, second elongated portion 3204, bight portion 3206 with flexible hinge 3208 and attachment feature 3210, a fastener portion 3212 and an engagement feature 3214. The clamp 3200 illustrated in FIG. 32 is similar to the clamp 2900 illustrated in FIG. 29, except, for example, that the fastener portion 3212 of the clamp 3200 omits the secondary opening 2912.

Figure 33:
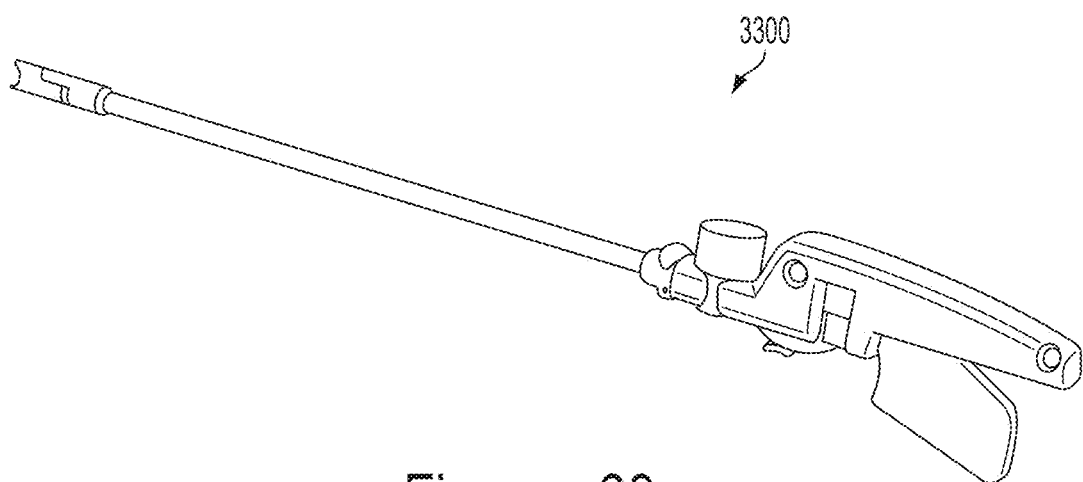
FIG. 33 is a perspective view of an embodiment of an installation tool used to install a one-piece surgical clamp.

Referring now to FIG. 33, another example embodiment of an installation tool 3300 is illustrated. The installation tool 3300 is similar to those discussed above, and may be used in a similar manner to engage and install certain embodiments of the surgical clamps illustrated in FIGS. 29-32. Using the installation tool 3300, the clamp may be engaged (via the attachment feature of the bight portion), placed in the abdominal cavity (e.g., via a trocar) and positioned with the first and second elongated portions on opposite sides of the stomach, where the clamp is latched, closed, fastened, secured, or otherwise installed to at least partially partition a cavity inside the stomach as described above.

Figure 34A:
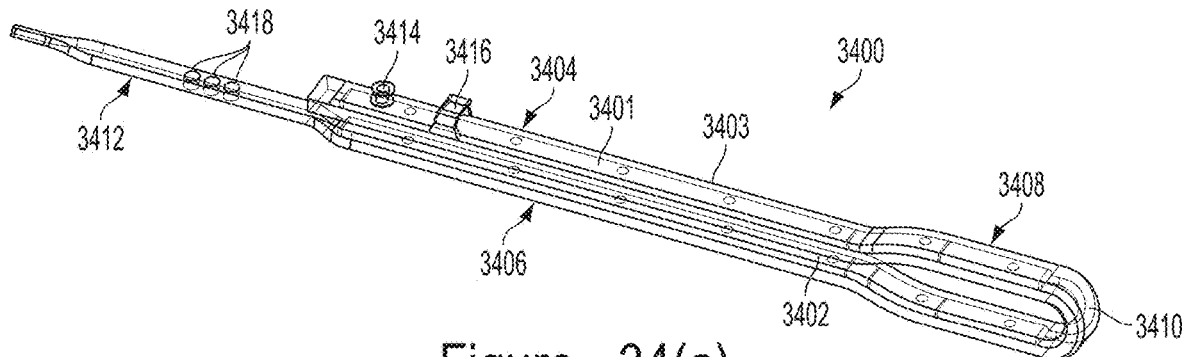
FIGS. 34(a), 34(b) and 34(c) illustrate various views of yet another embodiment of a one-piece surgical clamp comprised of first and second substrate members overmolded in a polymer material.
Figure 34B:
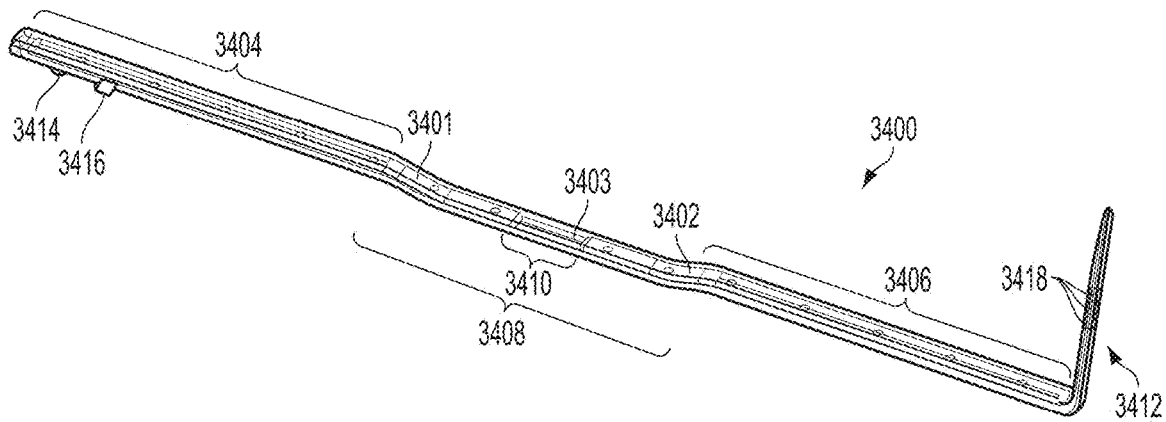
Figure 34C:
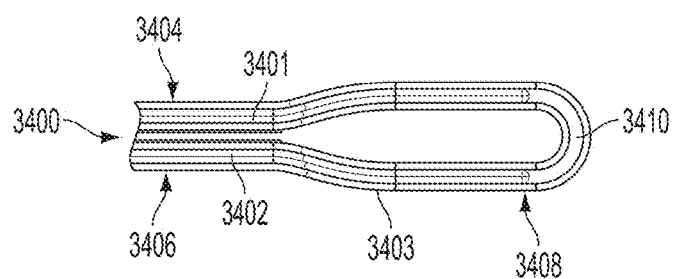

FIGS. 34(*a*), 34(*b*) and 34(*c*) illustrate various views of yet another embodiment of a one-piece surgical clamp 3400 comprised of first and second substrate members 3401 and 3402 overmolded in a polymer material 3403. The clamp 3400 includes a first elongated portion 3404, second elongated portion 3406, bight portion 3408 with flexible hinge 3410, a fastener portion 3412 and engagement features 3414 and 3416. The clamp 3400 illustrated in FIGS. 34(*a*), 34(*b*) and 34(*c*) is similar to the clamp 3200 illustrated in FIG. 32. The fastener portion 3412 of the clamp 3400 includes, for example, rounded primary openings 3418, and the bight portion 3412 omits an attachment feature. Additionally, the clamp 3400 incorporates first and second engagement features 3414 and 3416, wherein the first and second engagement features 3414 and 3416 include a raised member and a retaining loop, respectively, formed from the polymer overmolding 3403. In some embodiments, the raised member may also be formed, at least partially, from the first substrate member.

In accordance with the embodiment illustrated in FIGS. 34(*a*), 34(*b*) and 34(*c*), the clamp 3400 may be inserted to an abdominal cavity through a trocar, positioned with the first and second elongated portions 3404 and 3406 on opposite sides of the stomach, and closed and secured by engaging one of the primary openings 3418 with the raised member of the first engagement feature 3414, and securing the fastener portion 3412 under the retaining loop of the second engagement feature 3416. In accordance with the present embodiment, the inserting, positioning, closing and securing steps may be performed using surgical tools (e.g., clamps, forceps, scissors, etc.). However, it should be appreciated that the bight portion 3408 of the clamp 3400 may be modified to include an attachment feature, such as that provided in clamp 2900 or 3200, to allow for the clamp 3400 to be engaged and installed using a surgical clamp installation tool, such as that provided in FIG. 33.

Figure 35:
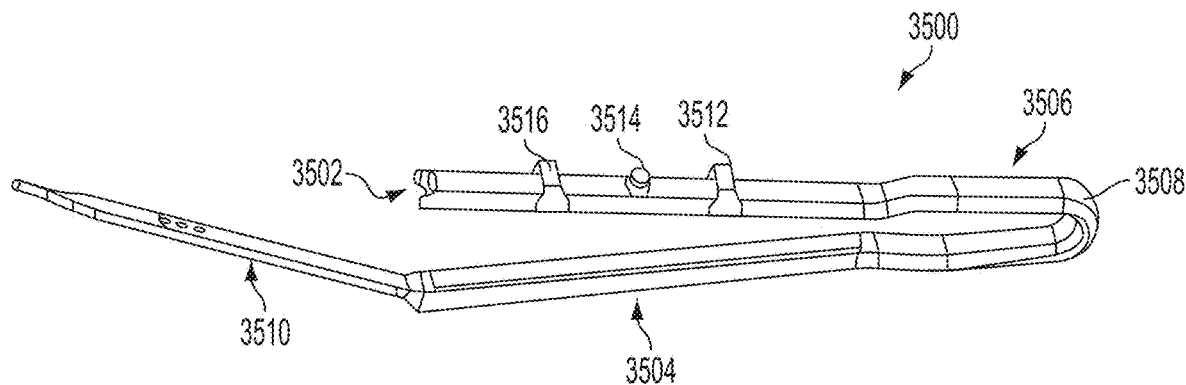
FIG. 35 is a perspective view of yet another embodiment of a one-piece surgical clamp comprised of first and second substrate members overmolded in a polymer material.

FIG. 35 illustrates another embodiment of a one-piece surgical clamp 3500 comprised of first and second substrate members overmolded in a polymer material. The clamp 3500 includes a first elongated portion 3502, second elongated portion 3504, bight portion 3506 with flexible hinge 3508, a fastener portion 3510 and engagement features 3512, 3514 and 3516. The clamp 3500 is similar to the clamp 3400 illustrated in FIGS. 34(*a*), 34(*b*) and 34(*c*). The clamp 3500 incorporates an additional engagement member 3516 comprising a retaining loop formed from the polymer overmolding for receiving the fastener portion 3510. The clamp 3500 is installed in a manner similar to the clamp 3400 and may be modified to include an attachment feature, such as that provided in clamp 2900 or 3200, to allow for the clamp 3500 to be engaged and installed using a surgical clamp installation tool, such as that provided in FIG. 33. It should be appreciated that the various embodiments discussed herein may be modified to include different numbers and combinations of engagement features and fastener portion openings without departing from the scope of the present disclosure as set forth in the claims below.

Figure 36:
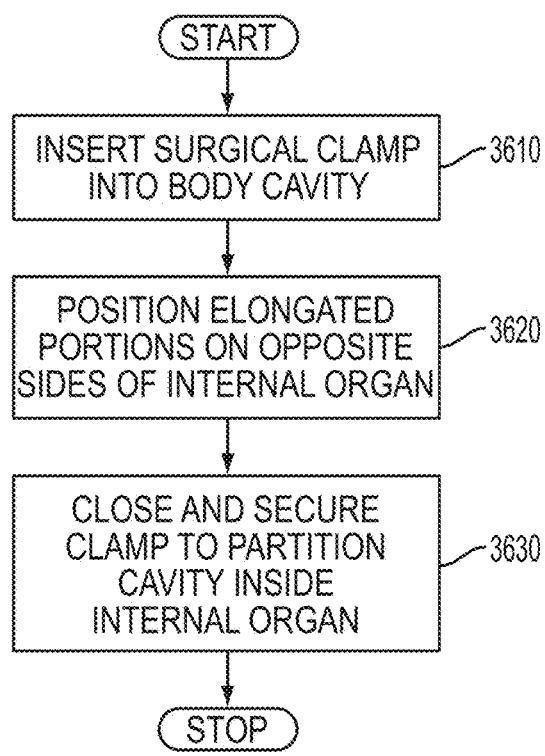
FIG. 36 is a flow diagram illustrating an embodiment of a method for clamping an internal organ.

Referring now to FIG. 36, a method for clamping an internal organ can include inserting a surgical clamp through an opening (e.g., using a trocar) into a body of a living organism at block 3610. Then the first and second elongated portions of the surgical clamp are positioned on opposite sides of an internal organ of the living organism at block 3620. At block 3630, closing and securing the surgical clamp to partition a cavity inside the internal organ includes clamping the exterior of the internal organ with the two elongated portions.

As mentioned above, the internal organ can be a human stomach. In this case, closing and securing the clamp can include installing the clamp in a substantially vertical or angled position with a passage-forming section of the clamp located towards a bottom of the stomach. This positioning can create a small, vertical stomach pouch and thereby limit the intake of food into an excluded section or portion of the stomach, but still allow certain gastric juices from the excluded portion of the stomach to flow into the vertical stomach pouch. This partitioning can alter the production of hormones, enzymes and chemicals that affect metabolism, energy levels, hunger, digestion, and absorption of nutrients that are affected by exclusion of gastric fundus and body of the stomach by the partitioning. The polymer overmolding of the clamp reduces trauma and/or necrosis of the stomach or other internal organ, thereby enabling successful reversal of the surgery. Thus, the above method can further include reversing the surgery by removing the clamp.

Inserting the surgical clamp can include performing natural orifice transluminal endoscopic surgery (NOTES). Alternatively, or additionally, it can include performing a combination of NOTES and an assistant trocar placed into an abdominal cavity. This combination can include two or more of a conventional, laparoscopic, NOTES, and one port technique. The NOTES technique can include at least one of transgastric, transvaginal, transrectal, transcolonic, or combinations thereof. The one port technique is used for the introduction of several instruments, and encompasses a one port abdominal (including umbilical), perineal, retroperitoneal approaches, or combinations thereof.

Figure 37:
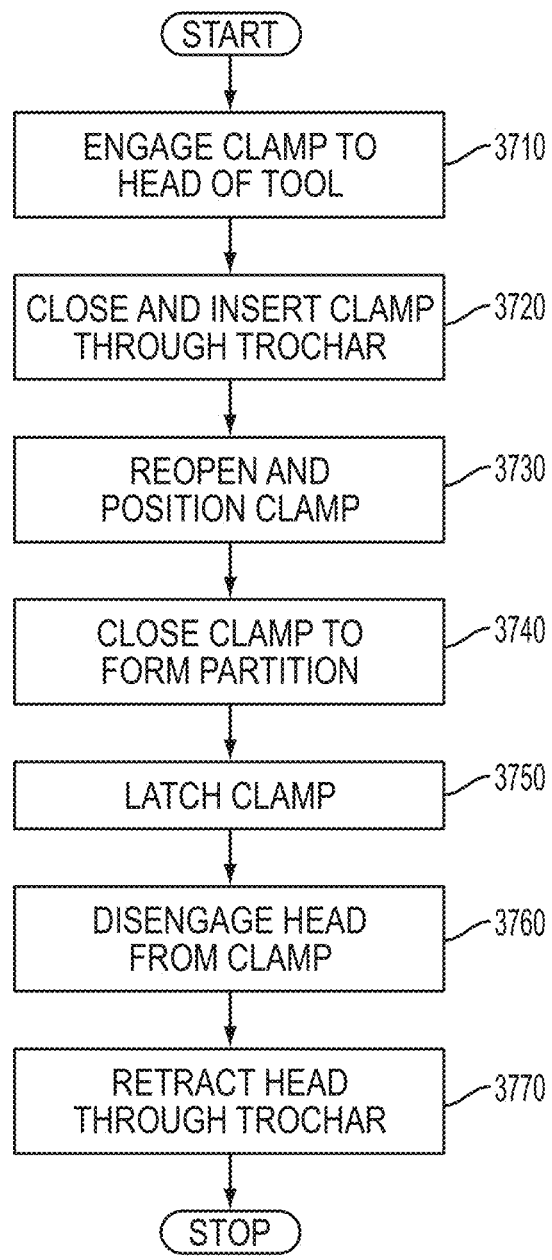
FIG. 37 is a flow diagram illustrating another embodiment of a method for clamping an internal organ.

Referring now to FIG. 37, a method for clamping an internal organ can include engaging a surgical clamp, such as a bariatric clamp, to a head of a surgical clamp installation tool at block 3710. At block 3720, the surgical clamp installation tool can be employed to close the clamp and insert the clamp through an opening in a body cavity of a living organism. Then the tool can be employed at block 3730 to reopen the clamp and to position the first and second elongated portions of the clamp on opposite sides of an internal organ within the body cavity.

Next, at block 3740, the tool can be employed to close the clamp upon the internal organ and thereby partition a cavity inside the internal organ. The limbs, arms, or elongated portions of the clamp close in such a fashion as causing a gradual diminishing space between the two elongated portions, as the space opening extends proximally, accounting for the different thickness of the stomach. The clamp closes in a fashion that exerts enough pressure to maintain the opposite walls closed to each other without creating any undue damage/trauma/ischemia to the stomach or other organ walls themselves. Then at block 3750, the clamp can be latched or otherwise secured to fix it in position to partition the internal organ and the cavity inside the internal organ. Also, at block 3760, the clamp can be disengaged from the head of the surgical clamp installation tool, and the tool can be retracted from the body cavity at block 3770. In some embodiments, the clamp may be latched or secured prior to or after disengaging and removing the surgical clamp installation tool. In such embodiments, the securing of the clamp may be performed using surgical tools alone or in combination with the installation tool. Alternatively, the tool may first be disengaged and removed, and the clamp subsequently latched using the additional surgical tools. Moreover, additional steps may be employed, either before or after the clamp is secured, to secure and position the clamp in place, such as using sutures.

As described above, the polymer overmolding of the surgical clamp reduces damage to the internal organ that would prevent or significantly decrease the likelihood of reversal of the surgical procedure. In some embodiments, the thickness or surface contour of the elongated portions of the surgical clamp may be provided to align with the particular organ or body being clamped so as to provide the desired pressure or force at each location of the organ or body being clamped. Additionally, engaging the surgical clamp to the head of the surgical clamp installation tool may include passing a T-bar adjacent the end of a pull rod of the installation tool through a slotted aperture formed in a bight portion of the clamp, and rotating the T-bar using a lever or dial. Also, employing the surgical clamp installation tool to close and reopen the clamp may include operating a lever or trigger on a handle of the installation tool to pull and release the pull rod. Further, employing the surgical clamp installation tool to position the elongated portions of the surgical clamp may include manipulating a dial on a handle of the installation tool to articulate the head from side to side in a desired plane(s).

Figure 38:
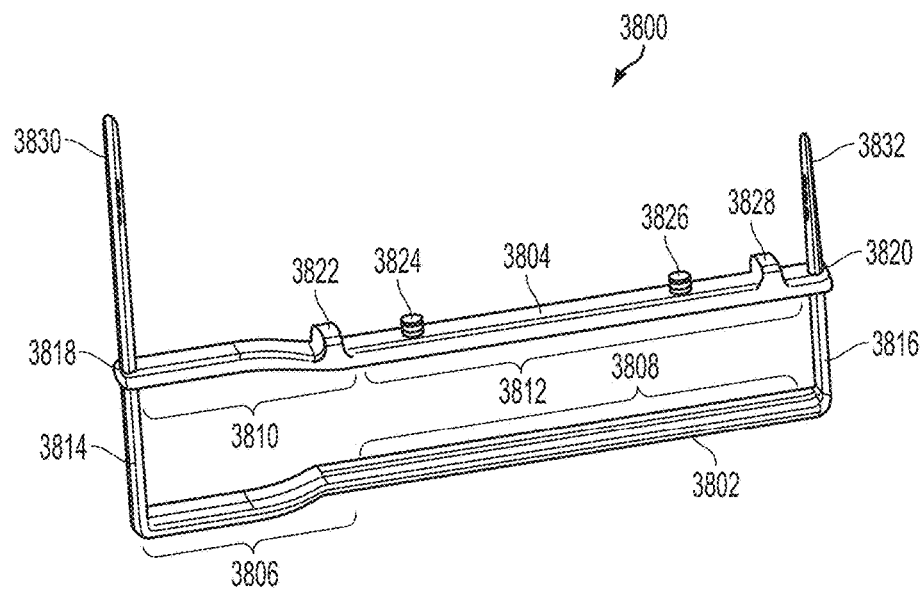
FIG. 38 is a perspective view of an embodiment of a two-piece surgical clamp comprised of first and second substrate members, each overmolded in a polymer material.
Figure 39A:
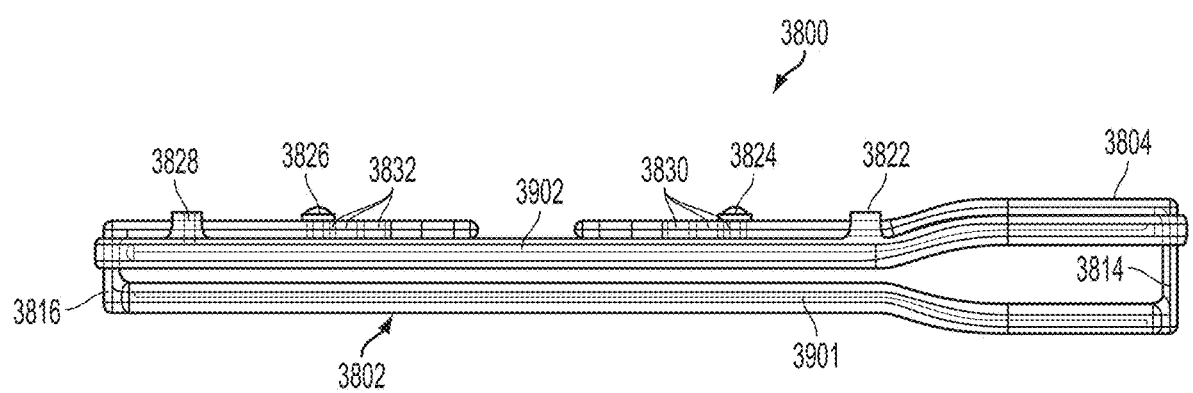
FIGS. 39(a), 39(b) and 39(c) illustrate various views of the two-piece surgical clamp of FIG. 38.
Figure 39B:
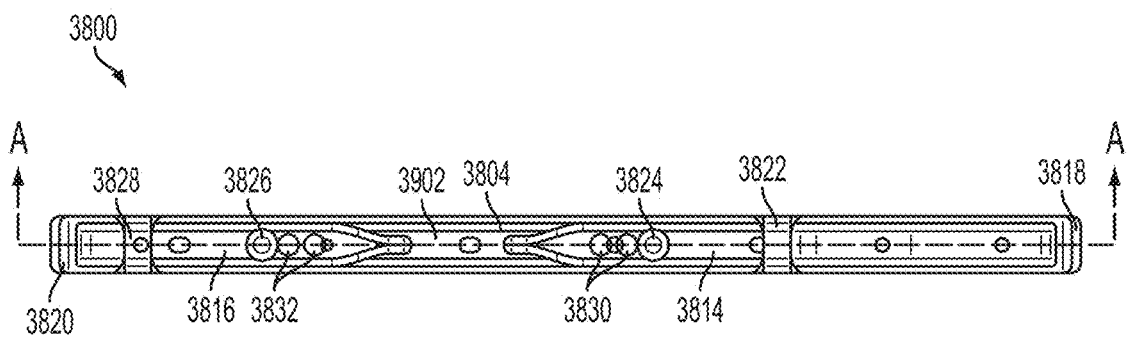
Figure 39C:
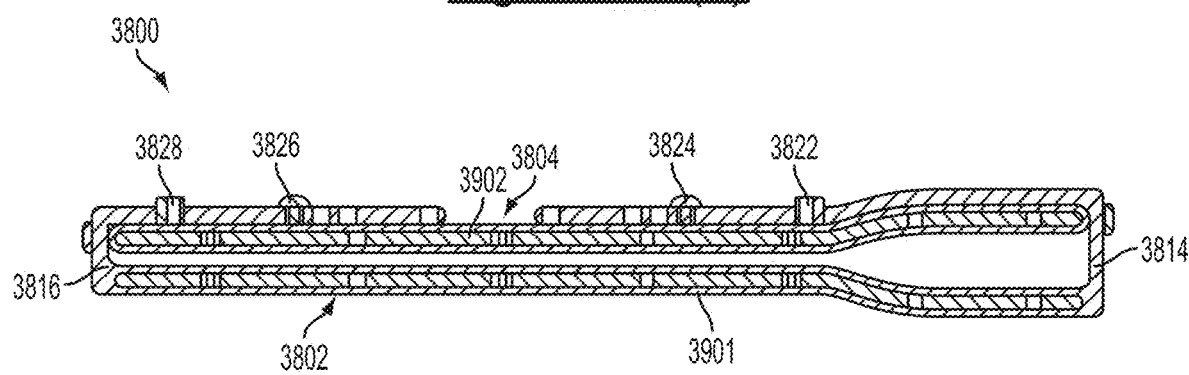

FIGS. 38, 39(a), 39(b) and 39(c) illustrate an embodiment of the present disclosure, wherein the polymer overmolded surgical clamp is of a two-piece design. FIG. 38 illustrates a perspective view of the two-piece clamp 3800, and FIGS. 39(a), 39(b) and 39(c) illustrate various views of the clamp 3800, wherein the polymer overmold is illustrated semi-transparent to show the underlying first substrate member 3901 and second substrate member 3902. FIG. 39(a) illustrates a profile view of the clamp 3800; FIG. 39(b) illustrates a top-down view of the clamp 3800; and FIG. 39(c) illustrates a cross-sectional view of the clamp 3800 taken along line A-A of FIG. 39(b).

The two-piece clamp 3800 includes first and second substrate members 3901 and 3902(shown in FIGS. 39(a), 39(b) and 39(c)) overmolded in a polymer material to form a first elongated member 3802 and a separate, second elongated member 3804. The first elongated member 3802 includes a first bight portion 3806 located towards a proximal end of the clamp 3800, and a first elongated portion 3808 located towards a distal end of the clamp 3800. The second elongated member 3804 includes a second bight portion 3810 located towards the proximal end of the clamp 3800 and a second elongated portion 3812 located towards the distal end of the clamp 3800. When the clamp is installed, the first and second bight portions 3806 and 3810 comprise a passage-forming section at the proximal end of the clamp 3800, and the first and second elongated portions 3808 and 3812 comprise a partition-forming section at the distal end of the clamp 3800. Referring briefly to both FIGS. 38 and 10, when the clamp 3800 is installed within an abdominal cavity, the first and second elongated portions 3808 and 3812 are engaged to partition the stomach into a small, vertical pouch 500 and excluded section 502, and the first and second bight portions 3806 and 3810 are engaged to form a passage that allows gastric juices to flow 506 from the excluded section 502 into the vertical pouch 500.

As shown in FIGS. 38, 39(*a*), 39(*b*) and 39(*c*), the first elongated member 3802 includes first and second fastening portions 3814 and 3816 formed at least partially from the polymer overmold at opposite ends of the first elongated member 3802. The second elongated member 3804 includes first and second receiving portions 3818 and 3820 formed from the polymer overmold at opposite ends of the second elongated member 3804, and retention features 3822, 3824, 3826 and 3828 formed at an outer surface of the second elongated member 3804. It should be understood that, in some embodiments, the first and second receiving portions 3818 and 3820 may be formed from the polymer overmold, or a combination of the second substrate material and polymer overmold. Similarly, in some embodiments, the retention features 3822, 3824, 3826 and 3828 may be formed from the polymer overmold, or a combination of the second substrate material and polymer overmold, as shown in FIG. 39(*c*).

When installing the clamp 3800, the first and second elongated members 3802 and 3804 are inserted into the abdominal cavity (for example, using a trocar) and positioned on opposite sides of the stomach. Then, the first and second fastening portions 3814 and 3816 are each fed through respective first and second receiving portions 3818 and 3820. A spacing between the bight portions 3806 and 3810 defines the passage formed at the bottom of the stomach and affects the pressure applied to the internal organ, whereas a spacing between the elongated portions 3808 and 3812 affects the pressure applied to the stomach by the partition-forming section of the clamp 3800. The spacing between the first and second bight portions 3806 and 3810 may be independently controlled primarily by adjusting the length of the first fastening portion 3814 fed through the first receiving portion 3818. Similarly, the spacing between the first and second elongated portions 3808 and 3812 may be independently controlled primarily by adjusting the length of the second fastening portion 3816 fed through the second receiving portion 3820. Once the desired spacing is achieved, the clamp 3800 is closed, latched or otherwise secured by engaging the first and second fastening portions 3814 and 3816 with the outer surface of the second elongated member 3804 using the retention features 3822, 3824, 3826 and 3828. The clamp 3800 may be adjusted or uninstalled by reversing the installation procedure. Additionally, in some embodiments, installation, removal, and/or adjustment of the clamp 3800 may be performed using standard surgical tools (e.g., forceps, clamps, scissors, etc.).

In the embodiment illustrated in FIGS. 38, 39(*a*), 39(*b*) and 39(*c*), retention features 3822 and 3828 comprise retention loops, and retention features 3824 and 3826 comprise raised members. The first fastening portion 3814 is fed through the first receiving portion 3818 and under the retaining loop 3822. The first fastening portion 3814 includes one or more openings 3830 operable to receive the raised member 3824. Once the first fastening portion 3814 is fed through the retaining loop 3822, it is secured via a friction fit using the raised member 3824 and one of the openings 3830. Similarly, the second fastening portion 3816 is fed through the second receiving portion 3820 and under the retaining loop 3828. The second fastening portion 3816 includes one or more openings 3832 operable to receive the raised member 3826. Once the second fastening portion 3816 is fed through the retaining loop 3828, it is secured via a friction fit using the raised member 3826 and one of the openings 3832. In some embodiments, the first and second fastening portions 3814 and 3816 may be further secured by suturing the fastening portions 3814 and 3816 to the second elongated member 3804 using suturing holes (not shown) formed within the second substrate member and polymer overmolding.

As briefly discussed above, the spacings at the passage-forming and partition-forming sections of the clamp may be adjusted independent of each other. Thus, the two-piece surgical clamp 3800 permits customized installation and adjustment of the surgical clamp 3800 by permitting one end of the clamp (i.e., the passage-forming section or the partition-forming section) to be adjusted without having to adjust the other end. This allows a surgeon or other medical personnel to control the clamping pressure at each end of the device regardless of differences in thickness of the stomach from one end of the clamp 3800 to the other.

Figure 40:
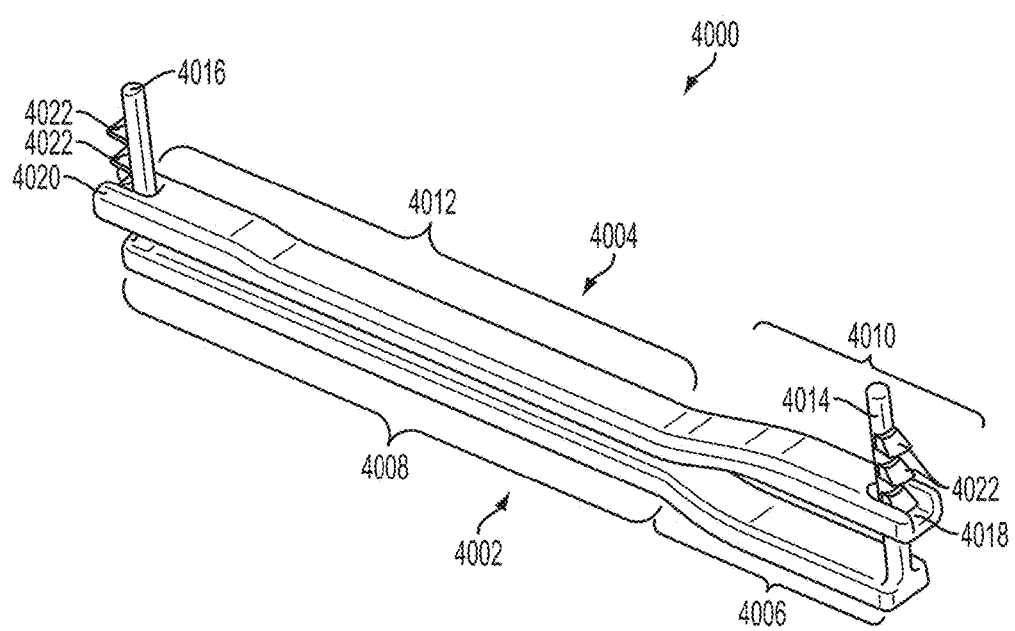
FIG. 40 is a perspective view of another embodiment of a two-piece surgical clamp comprised of first and second substrate members, each overmolded in a polymer material.

FIG. 40 illustrates another example embodiment of a two-piece surgical clamp 4000. The two-piece clamp 4000 includes first and second substrate members overmolded in a polymer material to form a first elongated member 4002 and a separate, second elongated member 4004. The first elongated member 4002 includes a first bight portion 4006 located towards a proximal end of the clamp 4000, and a first elongated portion 4008 located towards a distal end of the clamp 4000. The second elongated member 4004 includes a second bight portion 4010 located towards the proximal end of the clamp 4000 and a second elongated portion 4012 located towards the distal end of the clamp 4000. When the clamp is installed, the first and second bight portions 4006 and 4010 comprise a passage-forming section at the proximal end of the clamp 4000, and the first and second elongated portions 4008 and 4012 comprise a partition-forming section at the distal end of the clamp 4000. The spacing between the bight portions 4006 and 4010 defines the passage formed at the bottom of the stomach and affects the pressure applied to the internal organ, whereas the spacing between the elongated portions 4008 and 4012 affects the pressure applied to the stomach by the partition-forming section of the clamp 4000.

The first elongated member 4002 includes first and second fastening portions 4014 and 4016 formed from the polymer overmold at opposite ends of the first elongated member 4002. The second elongated member 4004 includes first and second receiving portions 4018 and 4020 formed from the polymer overmold at opposite ends of the second elongated member 4004. The embodiment illustrated in FIG. 40 is similar to that shown in FIGS. 38, 39(*a*), 39(*b*) and 39(*c*), except that the retention feature of the embodiment illustrated in FIG. 40 is embodied as a ratchet-type feature, wherein each of the first and second fastening portions 4014 and 4016 each include a plurality of "teeth" 4022 designed to engage the respective receiving portions 4018 and 4020 of the second elongated member 4004.

When installing the clamp 4000, the first and second elongated members 4002 and 4004 are inserted into the abdominal cavity (for example, using a trocar) and positioned on opposite sides of the stomach. The first and second fastening portions 4014 and 4016 are then fed through respective first and second receiving portions 4018 and 4020. The teeth 4022 on each of the fastening portions 4014 and 4016 are designed to flex to permit the feeding of respective fastening portion 4014 or 4016 through the respective receiving portion 4018 or 4020, and to engage the respective receiving portion 4018 or 4020 to retain the second elongated member 4004, thereby securing the clamp 4000 in a closed position. In some embodiments, the first and second elongated members 4002 and 4004 may be further secured by suturing the first and second elongated members 4002 and 4004 to the stomach using suturing holes (not shown) formed within the elongated members.

The spacing between the first and second bight portions 4006 and 4010 may be independently controlled primarily by adjusting the length of the first fastening portion 4014 fed through the first receiving portion 4018. Similarly, the spacing between the first and second elongated portions 4008 and 4012 may be independently controlled primarily by adjusting the length of the second fastening portion 4016 fed through the second receiving portion 4020. The clamp 4000 may be readjusted or uninstalled by disengaging the teeth 4022 of the fastening portions 4014 and 4016 from the respective receiving portions 4018 and 4020, and adjusting or removing the fastening portions 4014 and 4016 from the receiving portions 4018 and 4020. In some embodiments, once the clamp 4000 is installed, excess length of the first and second fastening portions 4014 and 4016 may be removed, for example, using scissors or other cutting instruments. In some embodiments, installation, removal, and/or adjustment of the clamp 4000 may be performed using standard surgical tools (e.g., forceps, clamps, scissors, etc.).

Like the clamp 3800 of FIG. 38, the two-piece clamp 4000 of FIG. 40 allows for independent adjustment of the spacings at the passage-forming and partition-forming sections of the clamp 4000. Thus, the two-piece surgical clamp 4000 permits customized installation and adjustment of the surgical clamp 4000 by permitting one end of the clamp (i.e., the passage-forming section or the partition-forming section) to be adjusted without having to adjust the other end. This allows a surgeon or other medical personnel to control the clamping pressure at each end of the device regardless of differences in thickness of the stomach from one end of the clamp 4000 to the other.

Embodiments of the polymer overmolded two-piece surgical clamp may be installed as described above with respect to the flow-chart illustrated in FIG. 36. Additionally, the polymer overmolding of the two-piece surgical clamp reduces or prevents damage to the internal organ that would prevent or complicate reversal of the surgical procedure. In some embodiments, the thickness or surface contour of the elongated portions of the surgical clamp may be provided to align with the particular organ or body being clamped so as to provide a desired pressure or force at each location of the organ or body being clamped. It should be appreciated that, in some embodiments, the first and second elongated members may be formed entirely from the polymer or elastomer material or resign and do not include an underlying substrate member.

It should be understood that one or more of the various fastening portions and retention features of the two-piece overmolded surgical clamp, such as the ratchet-like feature of the clamp 4000, the raised members and retention loops of the clamp 3800, or various combinations thereof may, in some embodiments, be incorporated in the one-piece overmolded surgical clamp. Additionally, in some embodiments, one or more of the engagement features of the one-piece overmolded surgical clamp may be incorporated in the two-piece overmolded surgical clamp. Furthermore, it should be appreciated that, in some embodiments, the one-piece surgical clamp may be a single, integrated unit or, in other embodiments, may be a modular unit formed of multiple pieces or parts combined to form the one-piece surgical (bariatric) clamp. It should also be appreciated that, in some embodiments, each of the pieces comprising the two-piece surgical clamp may include a single, integrated piece or, in other embodiments, may be a modular piece formed of multiple parts combined to form a piece of the two-piece surgical (bariatric) clamp.

FIGS. 41-48 and the accompanying description disclose various embodiments of a bariatric clamp (or surgical clamp) overmolded in a polymer material or are otherwise provided in support of such disclosure. The bariatric clamp is, in one implementation, a laparoscopically implanted device which, when closed and latched or secured, partitions a patient's stomach into two sections, such as two vertical sections or other divisions. The clamp may be installed using standard surgical tools (e.g., clamps, scissors, etc.) as further described below. When the clamp is installed, in one installation, the lesser curvature segment of the stomach forms the Magenstrasse, and the greater curvature segment, including the fundus, is generally excluded from nutritional contact. In one implementation, the clamp includes, at a proximal end, an aperture with an enlarged radius (generally referred to as the bight portion or passage-forming section), by which gastric juices created by the fundus and the body can empty into the atrum. By excluding the fundus, the clamp may alter or reduce hormones such as, for example, ghrelin, leading to the patient's loss of hunger. Additionally, the clamp acts as a restrictive procedure by reducing the size of the Magenstrasse by creating a small lumen for a vertical passageway of the nutrients along the lesser curvature.

FIGS. 41(a)-41(e) illustrate various views of an embodiment of an overmolded bariatric clamp 4100. The clamp 4100 includes first and second substrate members 4101 and 4103(shown dashed in FIGS. 41(a) and 41(e) and similar to those shown in FIGS. 30(a), 30(b), 31(a) and 31(b)) overmolded in a polymer or elastomer material to form a first elongated portion 4102, a second elongated portion 4104, a bight portion 4106, a fastener portion 4108, and an engagement portion 4114. As discussed above, the first and second elongated portions 4102 and 4104 serve as a partition-forming section of the bariatric clamp 4100. Referring briefly to both FIGS. 41(a) and 10, when the clamp 4100 is installed within an abdominal cavity, the first and second elongated portions 4102 and 4104 are engaged to partition the stomach into a small, vertical pouch 500 and an excluded section 502. The bight portion 4106 comprises a passage-forming section located towards the proximal end of the clamp 4100. The passage-forming section allows gastric juices to flow 506 from the excluded section 502 into the vertical pouch 500.

Figure 41A:
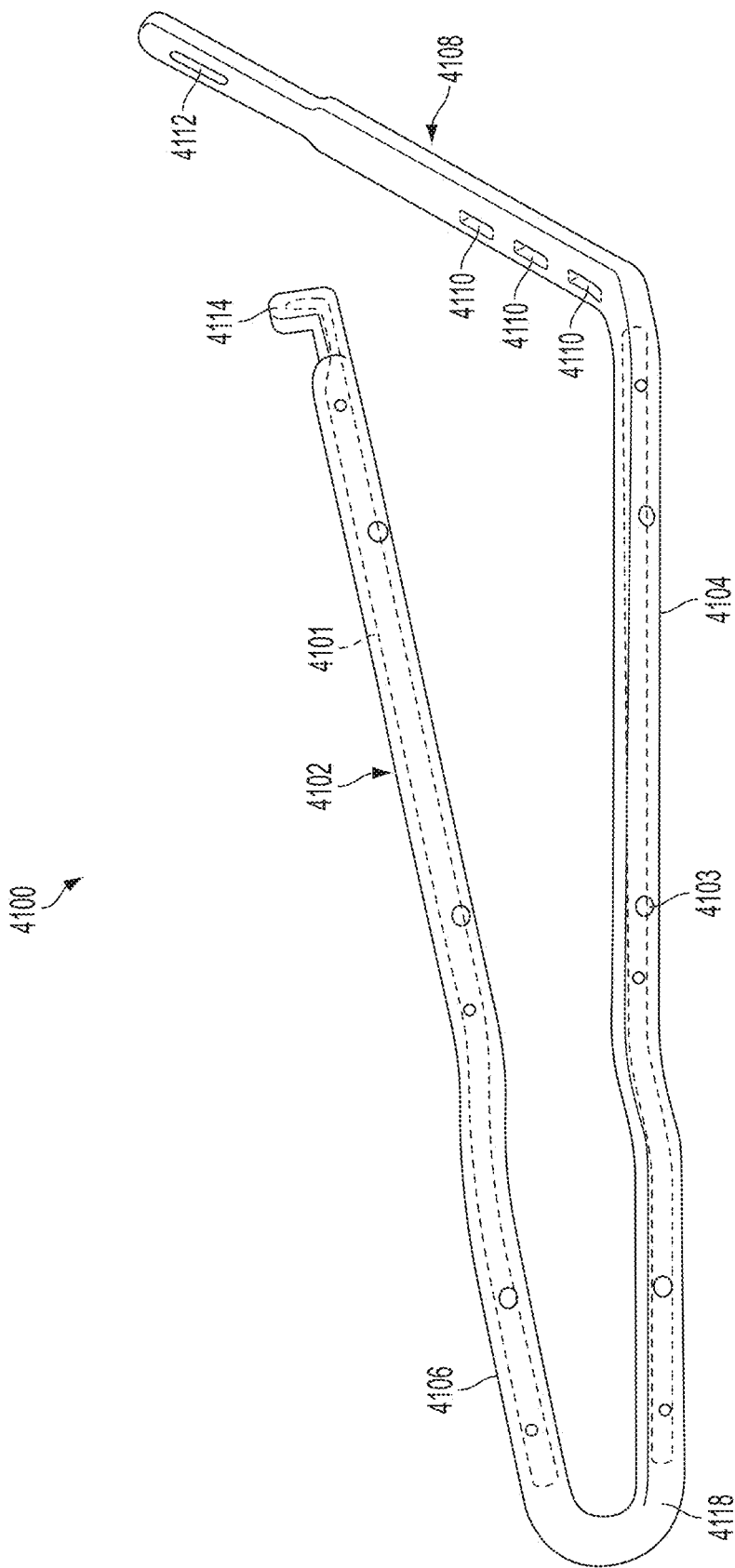
FIGS. 41(a)-41(e) illustrate various views of an embodiment of a bariatric clamp.
Figure 41B:
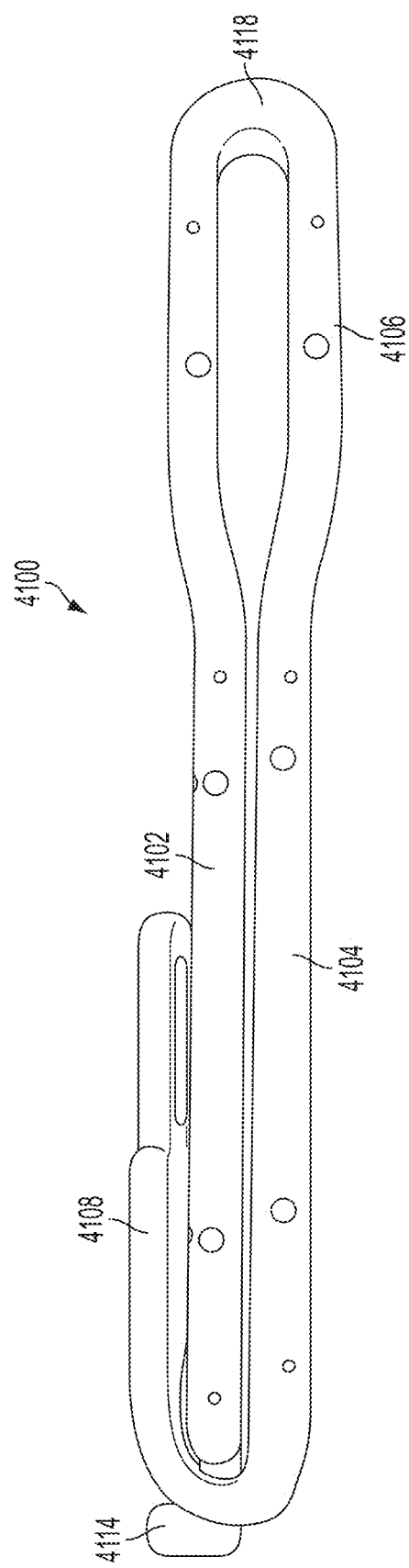
Figure 41C:
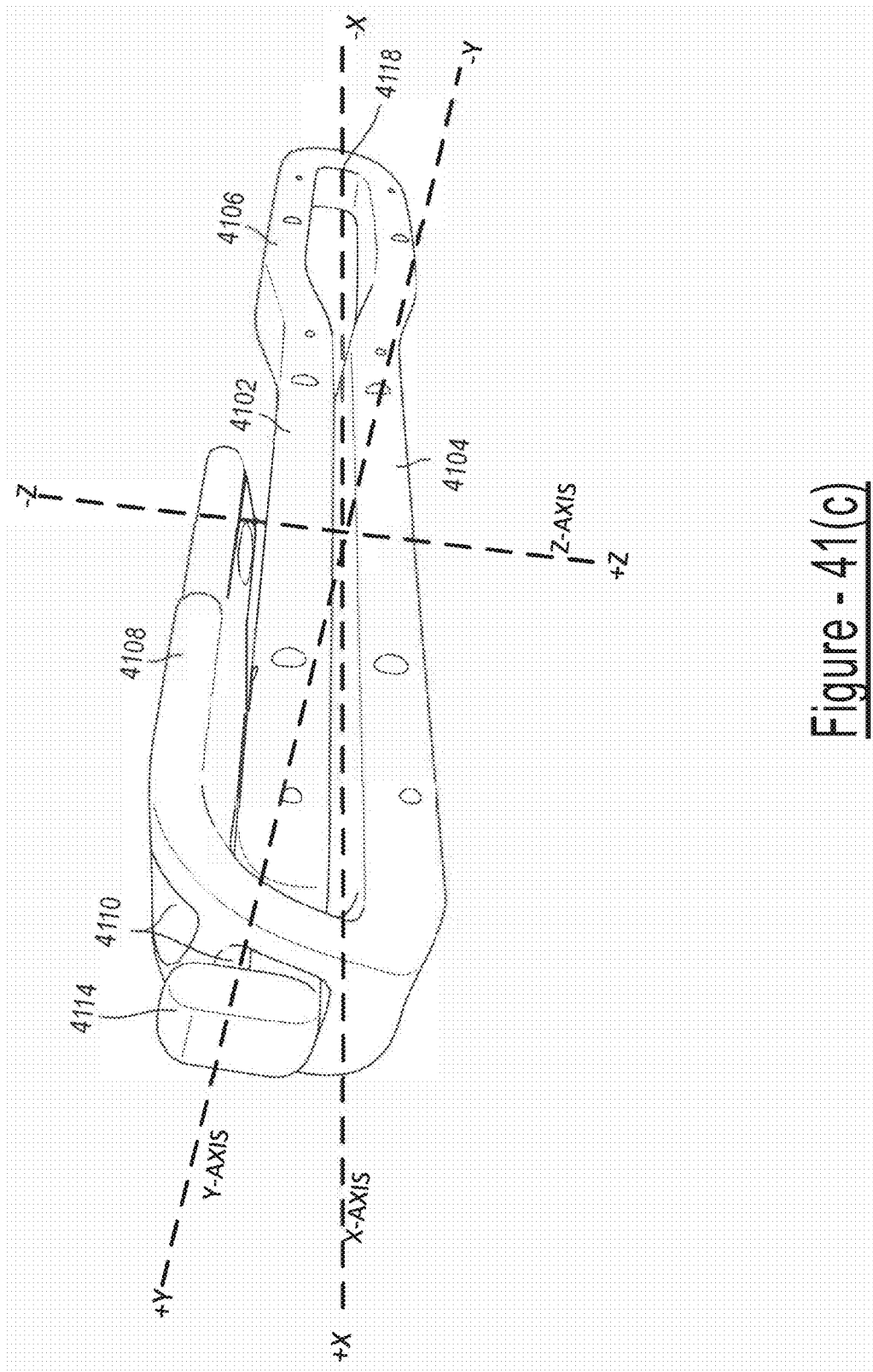
Figure 41D:
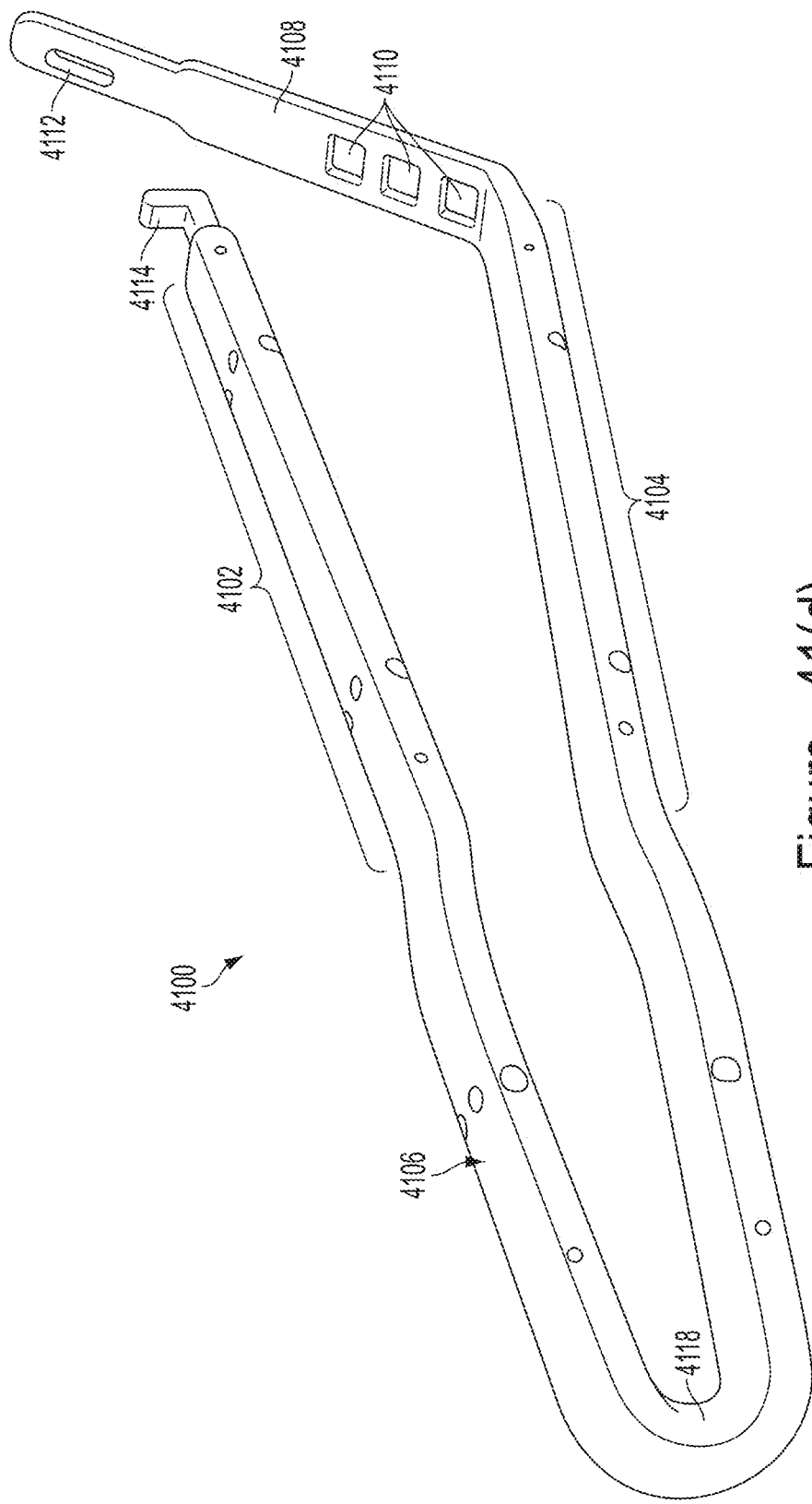
Figure 41E:
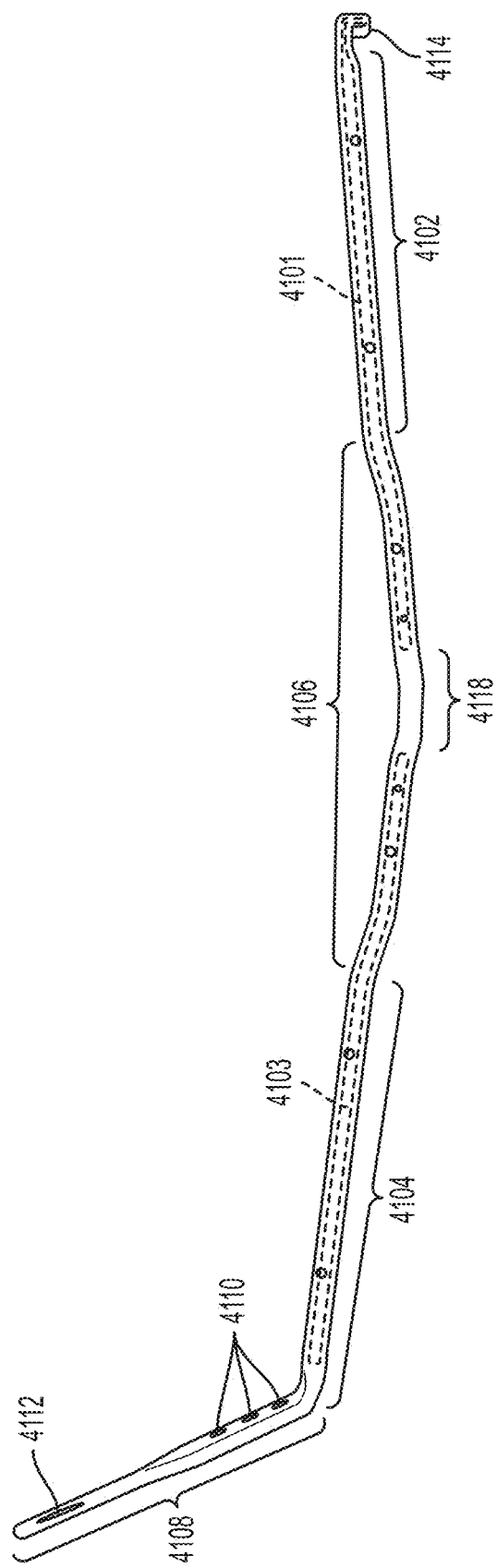

As shown in FIGS. 41(a)-41(e), the first and second elongated portions 4102 and 4104 are joined by the bight portion 4106, which is disposed generally at the proximal end of the clamp 4100. The bight portion 4106 includes a flexible hinge 4118 formed, in one implementation, from the polymer overmold. The flexible hinge 4118 allows the clamp 4100 to be positioned in a variety of positions ranging from a substantially closed position illustrated in FIGS. 41(b) and 41(c), to a substantially expanded (or fully opened) position as shown in FIG. 41(e). It should be appreciated that the flexible hinge 4118 allows the clamp 4100 to flex, twist, contort, expand, stretch, or flex in virtually any desired angle or position. For example, referring briefly to FIGS. 50(a)-50(d), the clamp 4100 is shown in a closed position in FIG. 50(a), opened such that an angle α at the bight portion is less than 90° in FIG. 50(b), opened such that the angle α at the bight portion is approximately 180° in FIG. 50(c), and opened such that the angle α at the bight portion is greater than 180° in FIG. 50(d).

Figure 51A:
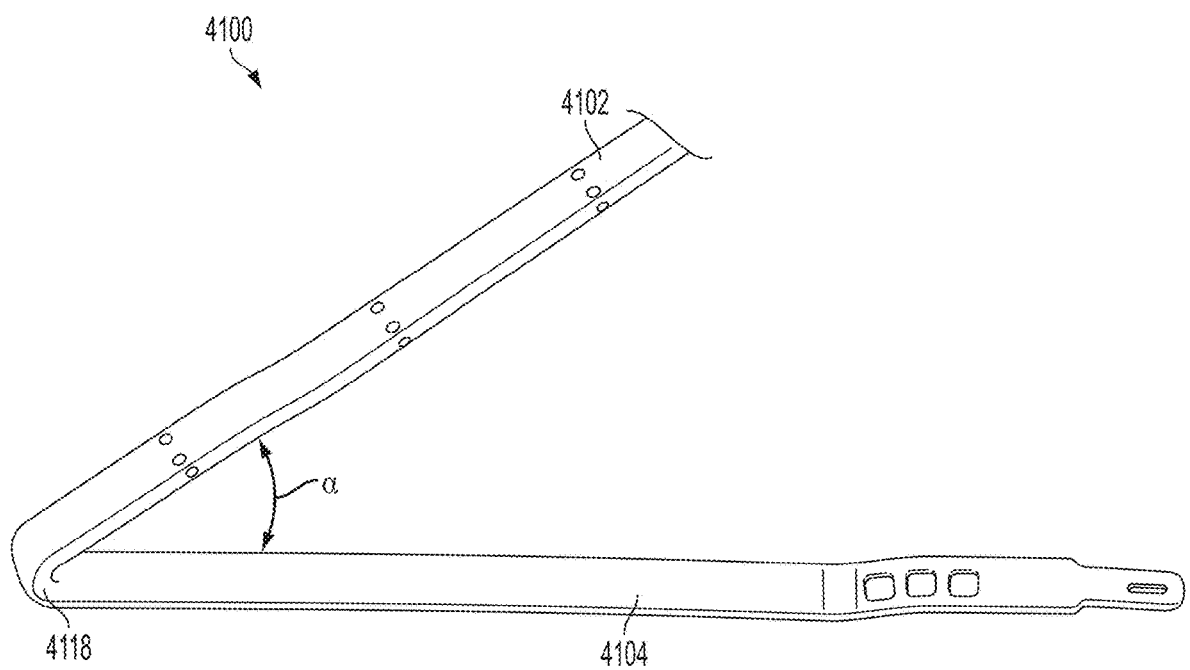
FIGS. 51(a), 51(b) and 51(c) illustrate an embodiment of the disclosed bariatric clamp in various contorted positions.
Figure 51C:
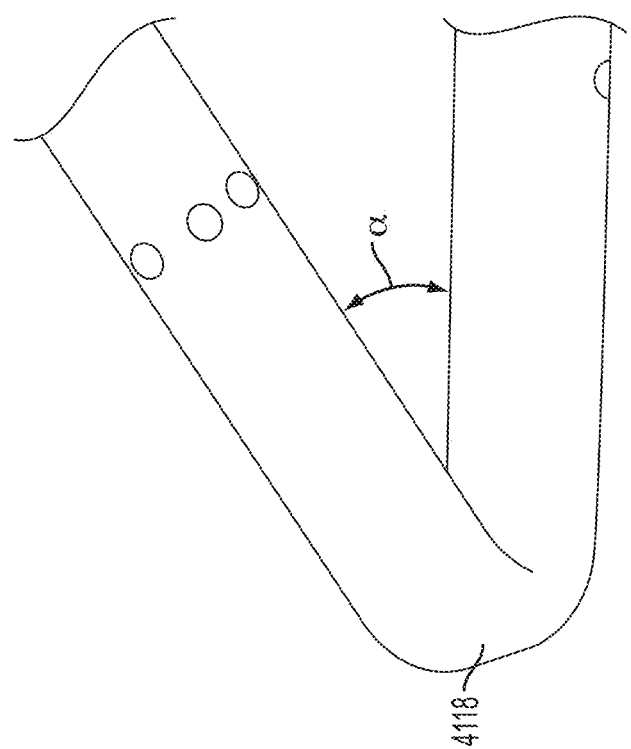
Figure 51B:
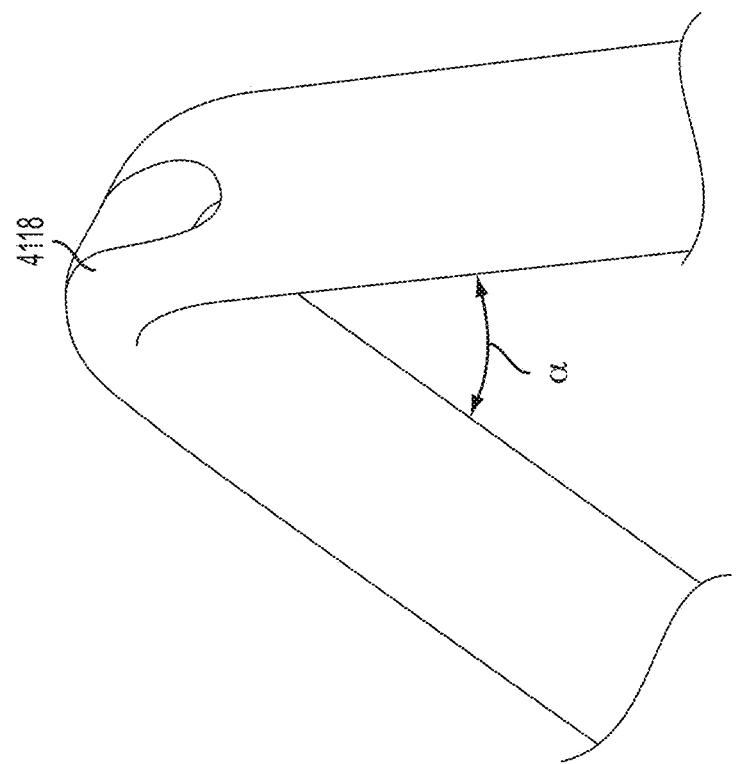
Figure 53A:
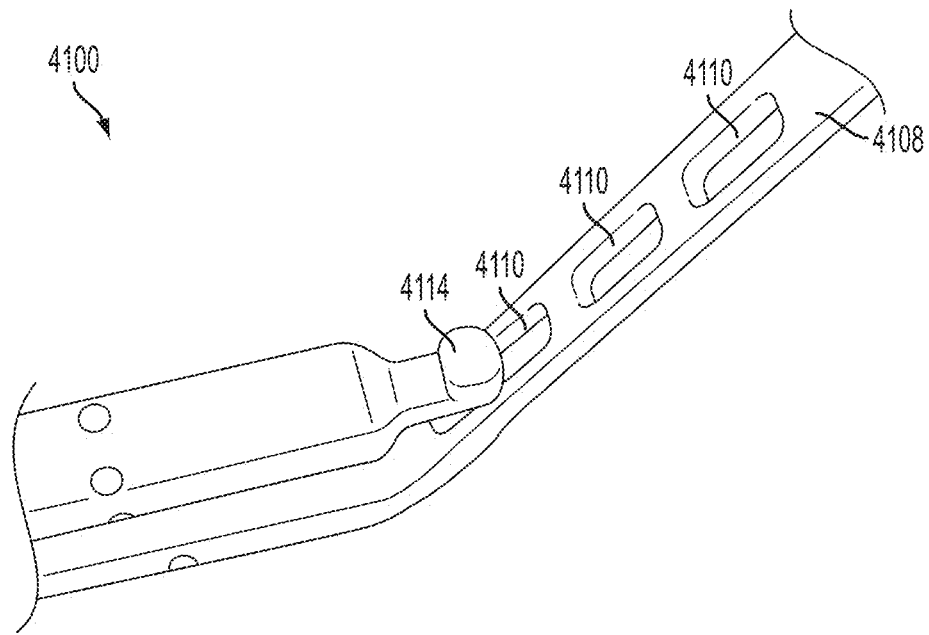
FIGS. 53(a)-53(e) illustrate various views of the engagement feature and fastener portion of an embodiment of the disclosed bariatric clamp.
Figure 53B:
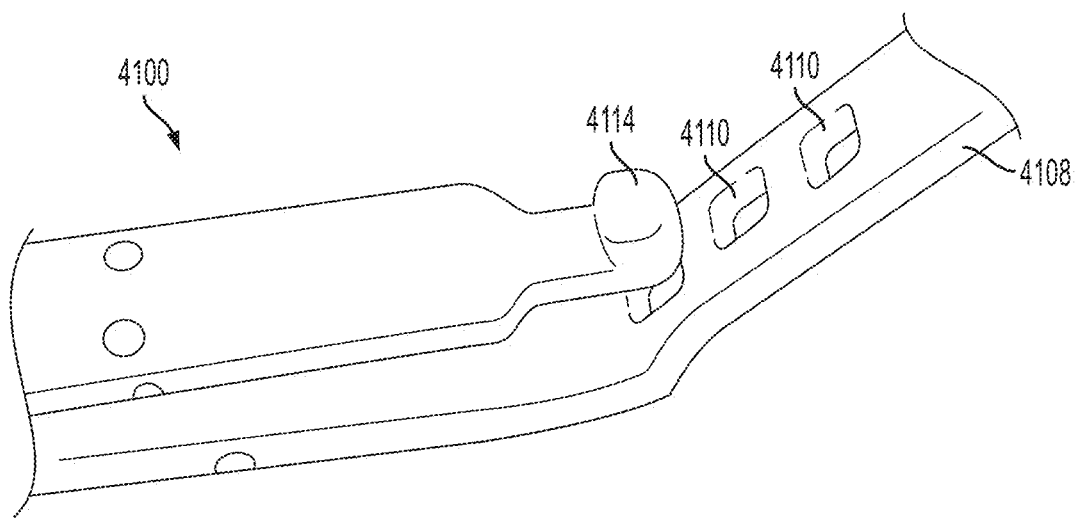
Figure 53C:
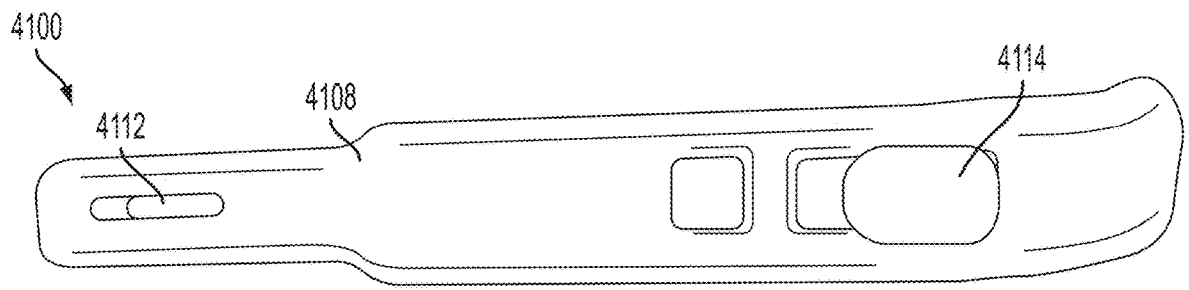
Figure 53D:
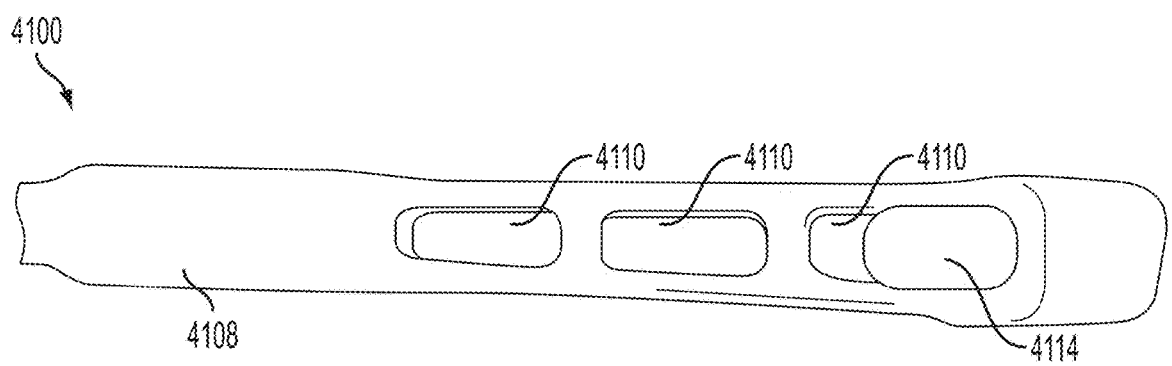
Figure 53E:
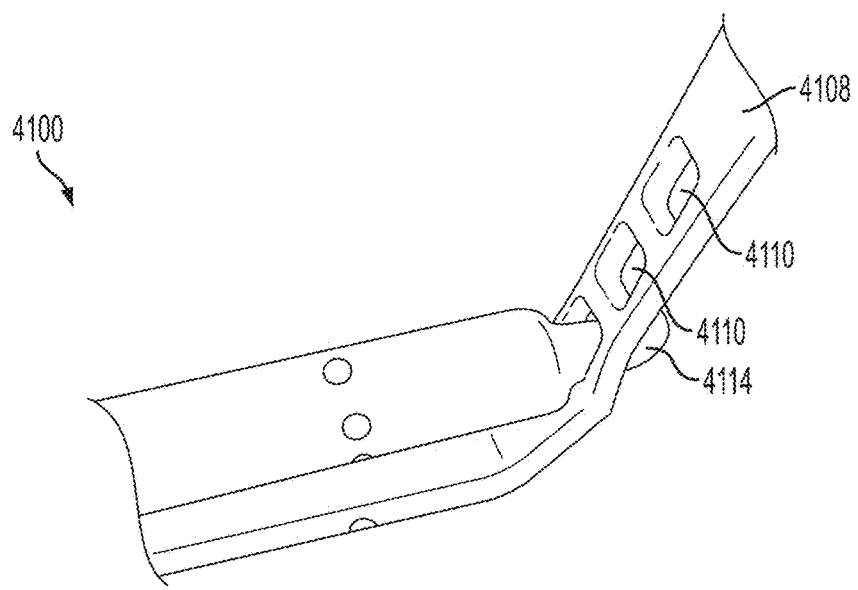

Referring briefly to FIGS. 51(a)-51(c), the clamp 4100 is shown in various contorted positions. As shown in FIGS. 51(a)-51(c), the flexible hinge 4118 allows the clamp 4100 to twist, bend, and flex in virtually any desired angle or direction such that the first and second elongated portions 4102 and 4104 may be displaced from each other at an angle (for example, angle α) when viewing the clamp 4100 from an overview position, such as that provided in FIG. 51(*a*). In some embodiments, the flexible hinge 4118 is stretchable and may twist to provide the first elongated member at a desired position in any of three orthogonal planes relative to the second elongated member. In some embodiments, the flexibility provided by the hinge 4118 may be beneficial when positioning the first and second elongated portions on the stomach during installation. For example, the flexible hinge 4118 allows the clamp 4100 to be installed, in one embodiment, into a smaller opening, such as an opening with a trocar, one elongated member at a time and then to properly install and position the bariatric clamp 4100 on the stomach in the limited space of the abdominal cavity.

When the clamp 4100 is installed, the flexible hinge 4118 permits expansion and movement of the bight portion 4106 to accommodate any irregularities in the stomach wall or fluctuations of the passage-forming section. For example, FIG. 52(*a*) illustrates the clamp 4100 in a closed position, wherein the flexible hinge 4118 is in a compressed, non-expanded position or resting state, and FIG. 52(*b*) illustrates the clamp 4100 in the closed position wherein the flexible hinge 4118 is stretched or expanded in a tensioned state. As previously mentioned, such stretching or expanding may accommodate irregularities in the stomach wall or fluctuations of the passage-forming section. The stretching or expanding of the flexible hinge 4118 also allows the clamp 4100 to accommodate variations in stomach thicknesses without compromising the pressure applied by the clamp 4100, particularly in the partition-forming section. In some embodiments, the flexible hinge 4118 may be provided at a desired durometer or elasticity that may be the same as or different from that of the polymer or silicone overmolded portions provided in other areas of the clamp 4100, such as the first and second elongated portions 4102 and 4104.

When installing the bariatric clamp 4100, the clamp 4100 is placed into position as explained in greater detail below, and the fastener portion 4108 and engagement portion 4114 are used to retain the clamp 4100 in a substantially closed position. FIGS. 41(*b*) and 41(*c*) illustrate the clamp 4100 in the substantially closed position. In the embodiment illustrated in FIGS. 41(*a*)-41(*e*), the fastener portion 4108 comprises a strap formed from the overmolded polymer, or other material, and located towards the distal end of the second elongated portion 4104. Because the fastener portion 4108 is formed from the overmolded polymer in some embodiments, it is stretchable and capable of providing appropriate tension to partition the stomach when installed. Also, as shown in FIGS. 53(*a*)-53(*e*), the fastener portion 4108 is capable of stretching so that one of the primary openings 4110 may receive the engagement portion 4114. The fastener portion 4108 may also include a secondary opening 4112 used for adjusting or manipulating the fastener portion 4108, the second elongated portion 4104 and/or the clamp 4100. For example, a surgeon may use a tool (not shown) to engage the secondary opening 4112 to position the strap such that the engagement portion 4114 engages one of the primary openings 4110. In the embodiment illustrated in FIGS. 41(*a*)-41(*e*) and 53(*a*)-53(*e*), the engagement portion 4114 comprises a protrusion, such as a hook or tab, for engaging openings of the fastener portion 4108.

In some embodiments, the clamp 4100 may be adjusted by disengaging the engagement portion 4114 from one of the primary openings 4110, and engaging the engagement portion 4114 with another one of the primary openings 4110 to either increase or decrease the spacing between the first and second elongated portions 4102 and 4104. In some embodiments, the fastener portion 4108 may be secured to the first elongated portion 4102 by suturing the fastener portion 4108 to the polymer overmolding of the first elongated portion 4102.

FIGS. 42(*a*), 42(*b*), 43(*a*) and 43(*b*) illustrate embodiments of an overmolded bariatric clamp similar to that shown in FIGS. 41(*a*)-41(*e*) and described above, except that the embodiments illustrated in FIGS. 42(*a*), 42(*b*), 43(*a*) and 43(*b*) have adjustable lengths. The adjustable length of the bariatric clamp allows for the clamp to be further customized to fit a patient's stomach during installation, or even after the clamp has been installed. For example, when installing the bariatric clamp, a surgeon is able to adjust the clamp as needed during installation to fit the patient's stomach. Additionally, if a bariatric clamp having an adjustable length is installed in a patient, and the length of the clamp is subsequently determined to be improper, the surgeon is able to adjust the length of the clamp to better fit the patient's stomach without having to remove the existing clamp or having to install a new clamp. Accordingly, a bariatric clamp having an adjustable length may prevent unnecessary surgical operations and/or reduce the amount of time required to install or adjust the bariatric clamp.

One embodiment of a bariatric clamp 4200 having an adjustable length is illustrated in FIGS. 42(*a*) and 42(*b*). The clamp 4200 includes first and second adjustable substrate members 4201 and 4203 (shown dashed) overmolded in a polymer or elastomer material to form a first elongated portion 4202, a second elongated portion 4204, a bight portion 4206, a fastener portion 4208, and an engagement portion 4214. The first and second elongated portions 4202 and 4204 serve as a partition-forming section of the bariatric clamp 4200. Referring briefly to FIGS. 42(*a*), 42(*b*) and 10, when the clamp 4200 is installed within an abdominal cavity, the first and second elongated portions 4202 and 4204 are engaged to partition the stomach into a small, vertical pouch 500 and an excluded section 502. The bight portion 4206 comprises a passage-forming section located towards the proximal end of the clamp 4200. The passage-forming section allows gastric juices to flow 506 from the excluded section 502 into the vertical pouch 500.

FIG. 42(*a*) illustrates the adjustable bariatric clamp 4200 in a retracted position wherein the length of the first elongated portion 4202 and the length of the second elongated portion 4204 are decreased to shorten the overall length of the clamp 4200. FIG. 42(*b*) illustrates the adjustable bariatric clamp 4200 in an extended position wherein the first elongated portion 4202 and the second elongated portion 4204 are extended to increase the overall length of the clamp 4200. In the embodiment illustrated in FIGS. 42(*a*) and 42(*b*), the adjustable length is provided, at least in part, by the first and second adjustable substrate members 4201 and 4203 comprising the first and second elongated portions 4202 and 4204, respectively, as well as portions of the bight portion 4206. As discussed herein, the adjustable substrate members 4201 and 4203 are each referred to as a single member, but it should be appreciated that they may each be comprised of two or more pieces as shown, for example, in FIGS. 42(*a*) and 42(*b*). It should also be appreciated that, in the embodiments discussed herein, the overmolded material is capable of stretching, expanding, and/or contracting to accommodate the extended and retracted lengths of the first and second elongated portions 4202 and 4204.

In some embodiments, the first adjustable substrate member 4201 may comprise an external member 4201A and an internal member 4201B, wherein the first adjustable substrate member 4201 is capable of at least partially disposing, or housing, the internal member 4201B within the external member 4201A. For example, the external member 4201A may be formed so that it has an opening 4205, or hollow portion, operable to receive the internal member 4201B. In this embodiment, the length of the first elongated portion 4202 may be adjusted by extending or retracting the internal member 4201B from or into the external member 4201A. Therefore, a user can extend the internal member 4201B from the external member 4201A as shown in FIG. 42(b) to increase the length of the first elongated portion 4202. Conversely, the user can retract, or insert, the internal member 4201B into the external member 4201A as shown in FIG. 42(a) to decrease the length of the first elongated portion 4202. In some embodiments, the external member 4201A, internal member 4201B, or both may include one or more detents (not shown) or other means for retaining a particular length of the first elongated portion 4202. Additionally (or alternatively), the length of the first elongated portion 4202 may be retained by suturing the first elongated portion 4202 to a portion of the stomach, or to another device or tissue, to prevent unintentionally adjusting the length of the first elongated portion 4202. In some embodiments, the length of the first elongated portion 4202 may be further increased by fully extending or removing the internal member 4201B from the external member 4201A. In other embodiments, the first adjustable substrate member may comprise one or more telescopic substrate members capable of telescopically expanding or retracting to adjust a length of the first elongated portion 4202 in a manner similar to that discussed above.

Similarly, in some embodiments, the second adjustable substrate member 4203 may comprise an external member 4203A and an internal member 4203B, wherein the second adjustable substrate member 4203 is capable of at least partially disposing, or housing, the internal member 4203B within the external member 4203A. For example, the external member 4203A may be formed so that it has an opening 4207, or hollow portion, operable to receive the internal member 4203B. In this embodiment, the length of the second elongated portion 4204 may be adjusted by extending or retracting the internal member 4203B from or into the external member 4203A. Therefore, a user can extend the internal member 4203B from the external member 4203A as shown in FIG. 42(b) to increase the length of the second elongated portion 4204. Conversely, the user can retract, or insert, the internal member 4203B into the external member 4203A as shown in FIG. 42(a) to decrease the length of the second elongated portion 4204. In some embodiments, the external member 4203A, internal member 4203B, or both may include one or more detents (not shown) or other means for retaining a particular length of the second elongated portion 4204. Additionally (or alternatively), the length of the second elongated portion 4204 may be retained by suturing the second elongated portion 4204 to a portion of the stomach, or to another device or tissue, to prevent unintentionally adjusting the length of the second elongated portion 4204. In some embodiments, the length of the second elongated portion 4204 may be further increased by fully extending or removing the internal member 4203B from the external member 4203A. In other embodiments, the second adjustable substrate member may comprise one or more telescopic substrate members capable of telescopically expanding or retracting to adjust a length of the second elongated portion 4204 in a manner similar to that discussed above.

As shown in FIGS. 42(a) and 42(b), the first and second elongated portions 4202 and 4204 are joined by the bight portion 4206 at the proximal end of the clamp 4200. The bight portion 4206 includes a flexible hinge 4218 formed, in one implementation, from the polymer overmold. The flexible hinge 4218 allows the clamp 4200 to be positioned in a variety of positions ranging from a substantially closed position (similar to that illustrated in FIGS. 41(b) and 41(c)), to a substantially expanded (or fully opened) position (similar to that shown in FIG. 41(e)). When the clamp 4200 is installed, the flexible hinge 4218 permits expansion and movement of the bight portion 4206 to accommodate any irregularities in the stomach wall or fluctuations of the passage-forming section. The flexible hinge 4218 also allows the clamp 4200 to accommodate variations in stomach thicknesses without compromising the pressure applied by the clamp 4200, particularly in the partition-forming section. In some embodiments, the flexible hinge 4218 may be provided at a desired durometer or elasticity that may be the same as or different from that of the polymer or silicone overmolded portions provided in other areas of the clamp 4200, such as the first and second elongated portions 4202 and 4204.

When installing the bariatric clamp 4200, the clamp 4200 is placed into position as explained in greater detail below, and the fastener portion 4208 and engagement portion 4214 are used to retain the clamp 4200 in a substantially closed position. In the embodiment illustrated in FIGS. 42(a) and 42(b), the fastener portion 4208 comprises a strap formed from the overmolded polymer, or other material, and located towards the distal end of the second elongated portion 4204. The strap may include one or more primary openings 4210 for receiving the engagement portion 4214, and a secondary opening 4212 used for adjusting or manipulating the fastener portion 4208, the second elongated portion 4204 and/or the clamp 4200. For example, a surgeon may use a tool (not shown) to engage the secondary opening 4212 to position the strap such that the engagement portion 4214 engages one of the primary openings 4210. In the embodiment illustrated in FIGS. 42(a) and 42(b), the engagement portion 4214 comprises a protrusion, such as a hook or tab, for engaging openings of the fastener portion 4208.

In some embodiments, the clamp 4200 may be adjusted by disengaging the engagement portion 4214 from one of the primary openings 4210, and engaging the engagement portion 4214 with another one of the primary openings 4210 to either increase or decrease the spacing between the first and second elongated portions 4202 and 4204. In some embodiments, this adjustment of the clamp 4200 may also include adjusting the length of the clamp 4200 in accordance with the foregoing description. In some embodiments, the fastener portion 4208 may be secured to the first elongated portion 4202 by suturing the fastener portion 4208 to the polymer overmolding of the first elongated portion 4202.

Another embodiment of a bariatric clamp 4300 having an adjustable length is illustrated in FIGS. 43(a) and 43(b). The clamp 4300 includes first and second substrate members 4301 and 4303(shown dashed) and first and second bight substrate members 4305 and 4307 (shown dashed) overmolded in a polymer or elastomer material to form a first elongated portion 4302, a second elongated portion 4304, a bight portion 4306, a fastener portion 4308, and an engagement portion 4314. The first and second elongated portions 4302 and 4304 serve as a partition-forming section of the bariatric clamp 4300. Referring briefly to FIGS. 43(*a*), 43(*b*) and 10, when the clamp 4300 is installed within an abdominal cavity, the first and second elongated portions 4302 and 4304 are engaged to partition the stomach into a small, vertical pouch 500 and an excluded section 502. The bight portion 4306 comprises a passage-forming section located towards the proximal end of the clamp 4300. The passage-forming section allows gastric juices to flow 506 from the excluded section 502 into the vertical pouch 500.

FIG. 43(*a*) illustrates the adjustable bariatric clamp 4300 in a retracted position wherein the length of the first elongated portion 4302 and the length of the second elongated portion 4304 are decreased to shorten the overall length of the clamp 4300. FIG. 43(*b*) illustrates the adjustable bariatric clamp 4300 in an extended position wherein the first elongated portion 4302 and the second elongated portion 4304 are extended to increase the overall length of the clamp 4300. In the embodiment illustrated in FIGS. 43(*a*) and 43(*b*), the adjustable length is provided, at least in part, by a first adjustable portion 4302A formed from the polymer overmold comprising the first elongated portion 4302 and a second adjustable portion 4304A formed from the polymer overmold comprising the second elongated portion 4304. The first and second adjustable portions 4302A and 4304A are shown in a retracted position in FIG. 43(*a*), and in an extended position in FIG. 43(*b*). It should be appreciated that, in some embodiments, the first and second adjustable portions 4302A and 4304A may be comprised of a material different from the polymer overmolding.

In some embodiments, the first adjustable portion 4302A is capable of extending (e.g., stretching, expanding, etc.) to increase the length of the first elongated portion 4302 and retracting (e.g., contracting) to decrease the length of the first elongated portion 4302. Therefore, a user may adjust the length of the first elongated portion 4302 by adjusting the position or placement of the first elongated portion 4302, while the first adjustable portion 4302A extends or retracts accordingly to account for corresponding adjustments of the length of the first elongated portion 4302. Similarly, in some embodiments, the second adjustable portion 4304A is capable of extending (e.g., stretching, expanding, etc.) to increase the length of the second elongated portion 4304 and retracting (e.g., contracting) to decrease the length of the second elongated portion 4304. Therefore, a user may adjust the length of the second elongated portion 4304 by adjusting the position or placement of the second elongated portion 4304, while the second adjustable portion 4304A extends or retracts accordingly to account for corresponding adjustments of the length of the second elongated portion 4304.

As discussed herein, the first and second adjustable portions 4302A and 4304A are capable of stretching, expanding, and/or contracting to accommodate the extended and retracted lengths of the first and second elongated portions 4302 and 4304. In some embodiments, the length of the first and/or second elongated portions 4302 and 4304 may be retained by suturing the first and/or second elongated portions 4302 and 4304 to a portion of the stomach, or to another device or tissue, to prevent unintentionally adjusting the length of the first and/or second elongated portions 4302 and 4304. Although FIGS. 43(*a*) and 43(*b*) illustrate the first adjustable portion 4302A disposed at a location adjacent the first bight substrate member 4305 and the first substrate member 4301, the first adjustable portion 4302A may be disposed at other locations along the length of the first elongated portion 4302. Similarly, although FIGS. 43(*a*) and 43(*b*) illustrate the second adjustable portion 4304A disposed at a location adjacent the second bight substrate member 4307 and the second substrate member 4303, the second adjustable portion 4304A may be disposed at other locations along the length of the second elongated portion 4304.

In some embodiments, the first and second adjustable portions 4302A and 4304A are capable of bending, flexing or hinging such that the bight portion 4306 is capable of being disposed at a desired angle relative to the length of the first and second elongated portions 4302 and 4304. For example, FIG. 54(*a*) illustrates an embodiment wherein the clamp 4300 is installed on a stomach 5400 and the first and second adjustable portions 4302A and 4304A are hinged such that the bight portion 4306 is angled in a first direction relative to the first and second elongated portions 4302 and 4304. In another example embodiment, FIG. 54(*b*) illustrates the clamp 4300 installed on the stomach 5400 and the first and second adjustable portions 4302A and 4304A are hinged such that the bight portion 4306 is angled in a second direction relative to the first and second elongated portions 4302 and 4304. In some embodiments, the hinging portion of the clamp 4300 as described herein may be provided by hinges or other features incorporated in the clamp 4300 at locations where the first and second elongated portions 4302 and 4304 join the bight portion 4306. In some embodiments, the first and second adjustable portions 4302A and 4304A may maintain the bight portion 4306 at a fixed angle.

Figure 54A:
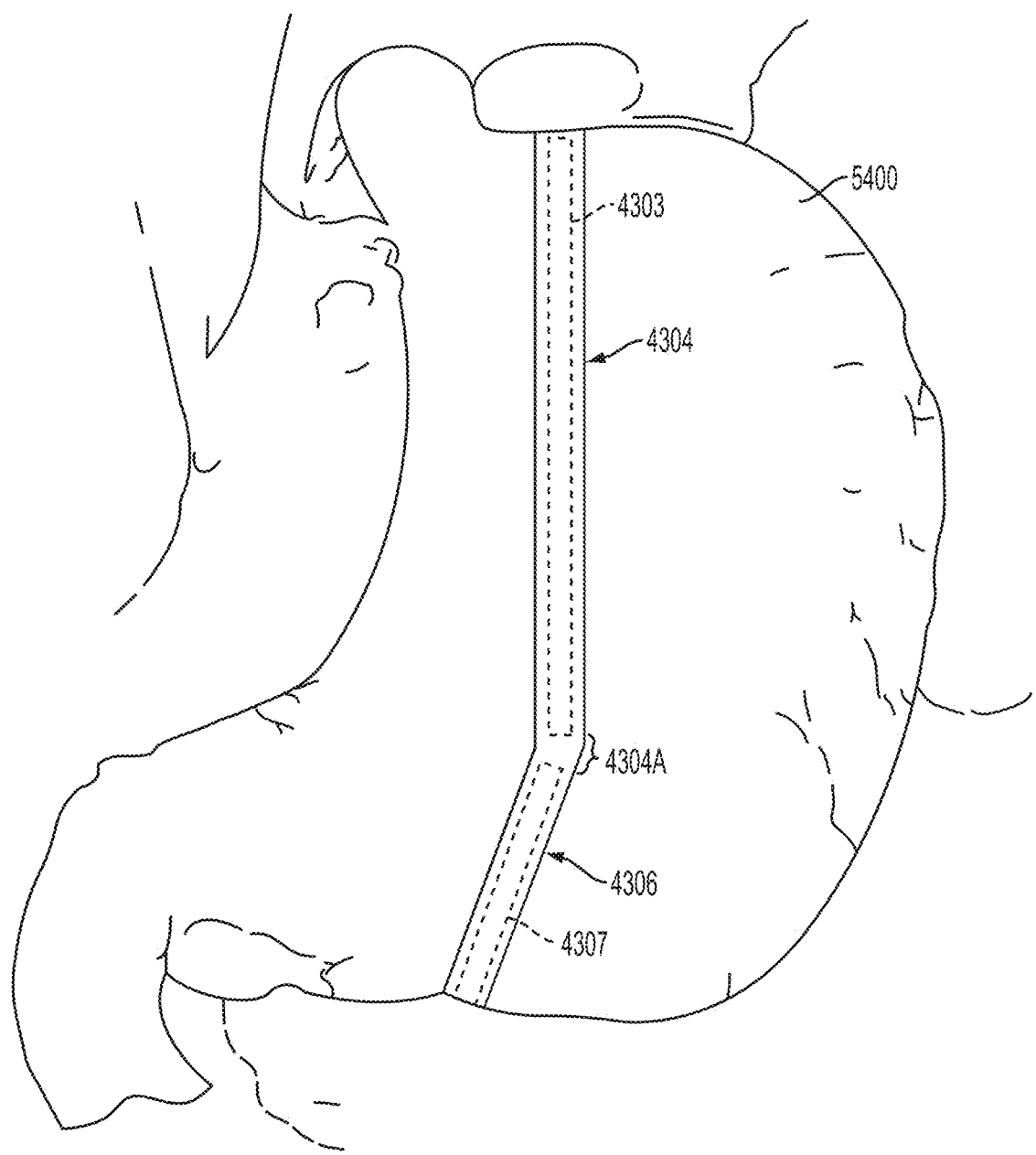
FIG. 54(a) illustrates an embodiment wherein an embodiment of the disclosed bariatric clamp is installed on a stomach and first and second adjustable portions are hinged such that the bight portion is angled in a first direction relative to the first and second elongated portions.
Figure 54B:
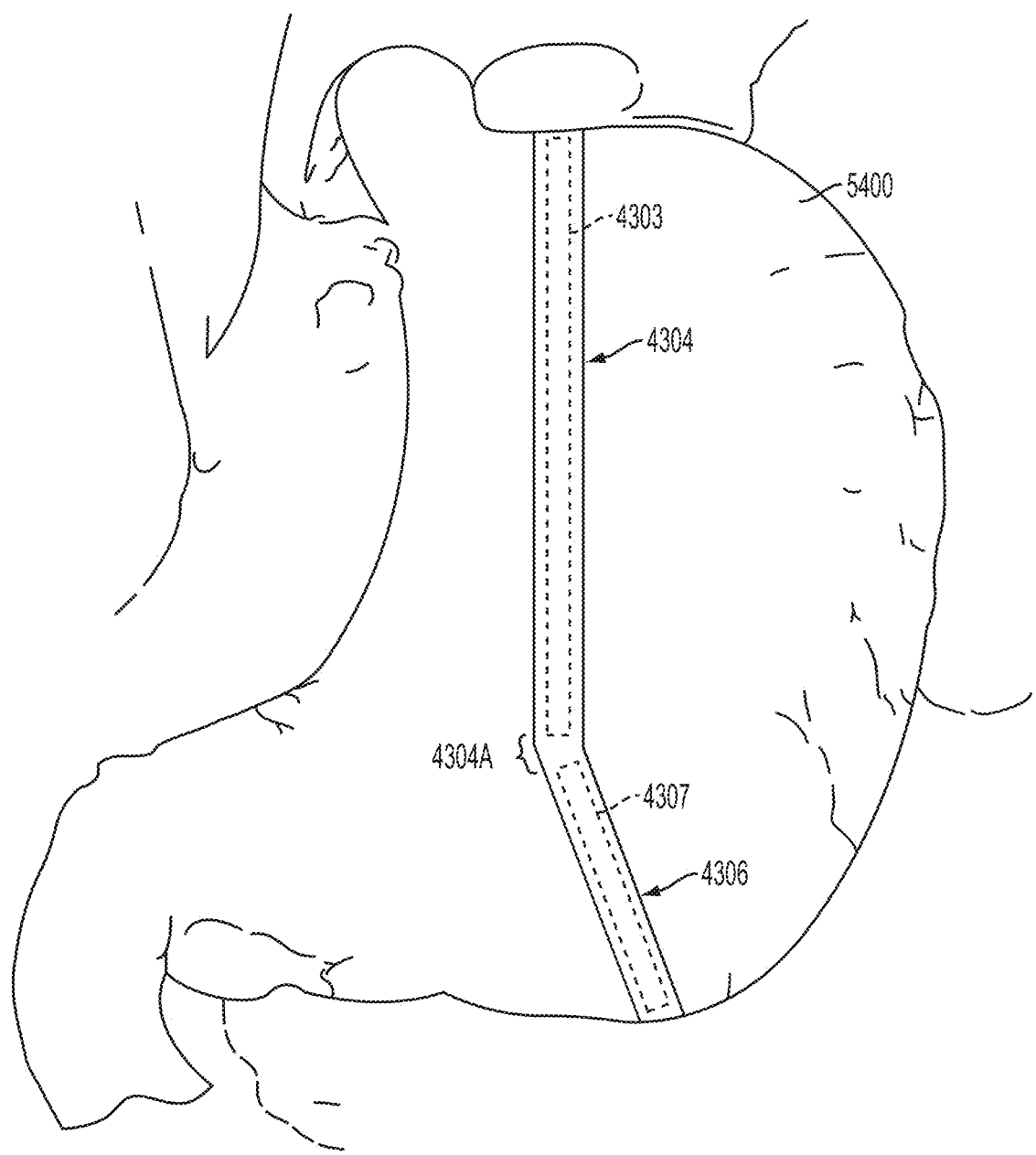
FIG. 54(b) illustrates another embodiment wherein an embodiment of the disclosed bariatric clamp is installed on a stomach and first and second adjustable portions are hinged such that the bight portion is angled in a second direction relative to the first and second elongated portions.

It should be appreciated that, in some embodiments, the clamp may be positioned at various locations along the stomach as desired. For example, as shown in FIG. 54(*a*), the top portion of the clamp may be positioned at a location at the top of the stomach adjacent the esophagus and the bottom portion of the clamp may be positioned at a location at the bottom of the stomach horizontally off-set relative to the location at which the top portion of the clamp is positioned. This may be achieved by providing a clamp that can bend, flex, adjust, hinge, or curve to achieve the desired positioning (as is the case in FIG. 54(*a*)), or it may be achieved by positioning the clamp so that it is angled with respect to a vertical axis extending from the bottom of the stomach towards the top of the stomach. In some embodiments, such positioning may be useful for ensuring that the vertical food pouch or the portion of the stomach beneath the esophagus has a substantially uniform size from the top of the stomach towards the bottom portion of the stomach.

As shown in FIGS. 43(*a*) and 43(*b*), the first and second elongated portions 4302 and 4304 are joined by the bight portion 4306 at the proximal end of the clamp 4300. The bight portion 4306 includes a first bight substrate member 4305, second bight substrate member 4307, and a flexible hinge 4318 formed, in one implementation, from the polymer overmold. The first and second bight substrate members 4305 and 4307 are similar (in both functionality and composition) to the first and second substrate members 4301 and 4303(and other substrate members disclosed herein), and may be formed of various biocompatible materials such as titanium or biocompatible polymer resins such as polyether ketone ketone (PEKK) or polyether ether ketone (PEEK). The flexible hinge 4318 allows the clamp 4300 to be positioned in a variety of positions ranging from a substantially closed position (similar to that illustrated in FIGS. 41(*b*) and 41(*c*)), to a substantially expanded (or fully opened) position (similar to that shown in FIG. 41(*e*)). When the clamp 4300 is installed, the first and second bight substrate members 4305 and 4307 provide structural support to the passage-forming section of the clamp 4300. Additionally, the flexible hinge 4318 permits expansion and movement of the bight portion 4306 to accommodate any irregularities in the stomach wall or fluctuations of the passage-forming section. The flexible hinge 4318 also allows the clamp 4300 to accommodate variations in stomach thicknesses without compromising the pressure applied by the clamp 4300, particularly in the partition-forming section. In some embodiments, the flexible hinge 4318 may be provided at a desired durometer or elasticity that may be the same as or different from that of the polymer or silicone overmolded portions provided in other areas of the clamp 4300, such as the first and second elongated portions 4302 and 4304.

When installing the surgical clamp 4300, the clamp 4300 is placed into position as explained in greater detail below, and the fastener portion 4308 and engagement portion 4314 are used to retain the clamp 4300 in a substantially closed position. In the embodiment illustrated in FIGS. 43(*a*) and 43(*b*), the fastener portion 4308 comprises a strap formed from the overmolded polymer, or other material, and located towards the distal end of the second elongated portion 4304. The strap may include one or more primary openings 4310 for receiving the engagement portion 4314, and a secondary opening 4312 used for adjusting or manipulating the fastener portion 4308, the second elongated portion 4304 and/or the clamp 4300. For example, a surgeon may use a tool (not shown) to engage the secondary opening 4312 to position the strap such that the engagement portion 4314 engages one of the primary openings 4310. In the embodiment illustrated in FIGS. 43(*a*) and 43(*b*), the engagement portion 4314 comprises a protrusion, such as a hook or tab, for engaging openings of the fastener portion 4308.

In some embodiments, the clamp 4300 may be adjusted by disengaging the engagement portion 4314 from one of the primary openings 4310, and engaging the engagement portion 4314 with another one of the primary openings 4310 to either increase or decrease the spacing between the first and second elongated portions 4302 and 4304. In some embodiments, this adjustment of the clamp 4300 may also include adjusting the length of the clamp 4300 in accordance with the foregoing description. In some embodiments, the fastener portion 4308 may be secured to the first elongated portion 4302 by suturing the fastener portion 4308 to the polymer overmolding of the first elongated portion 4302.

Figure 44A:
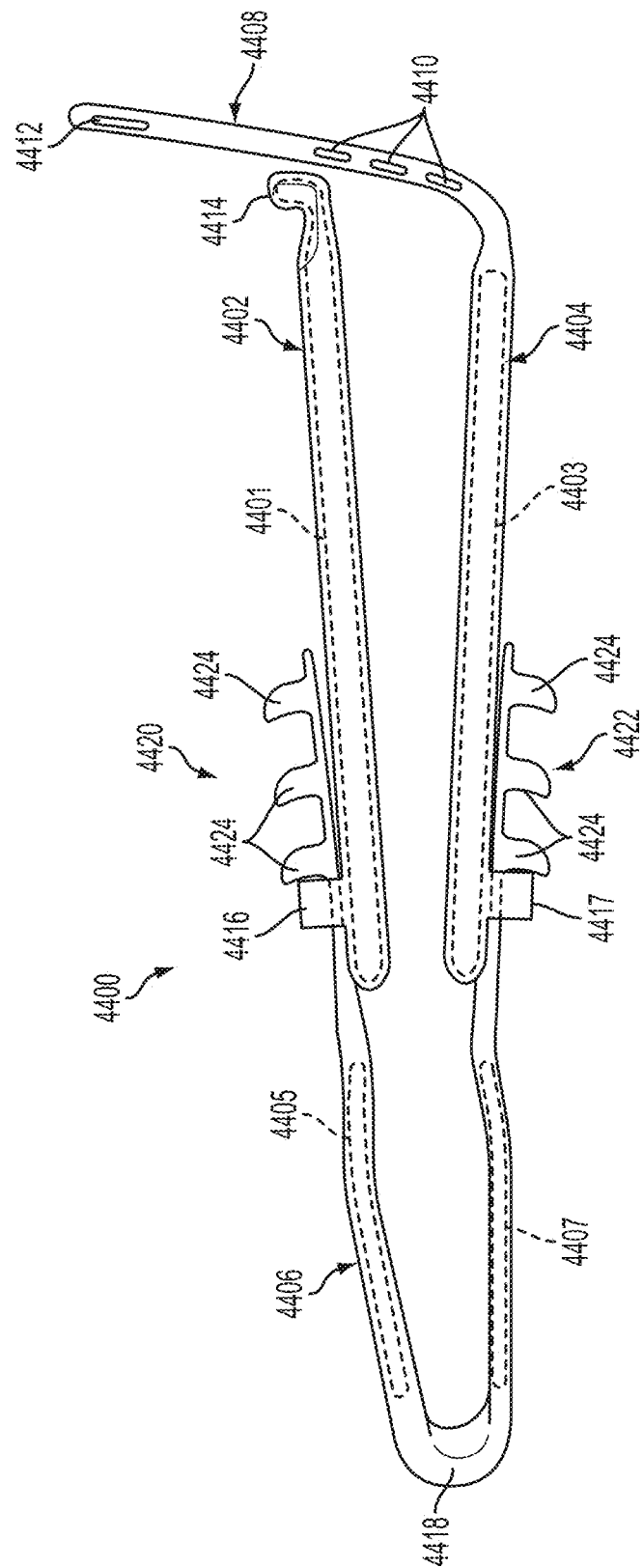
FIGS. 44(a) and 44(b) illustrate an embodiment of an adjustable bariatric clamp having a ratchet feature, wherein the clamp is shown in a retracted position and an extended position, respectively.
Figure 44B:
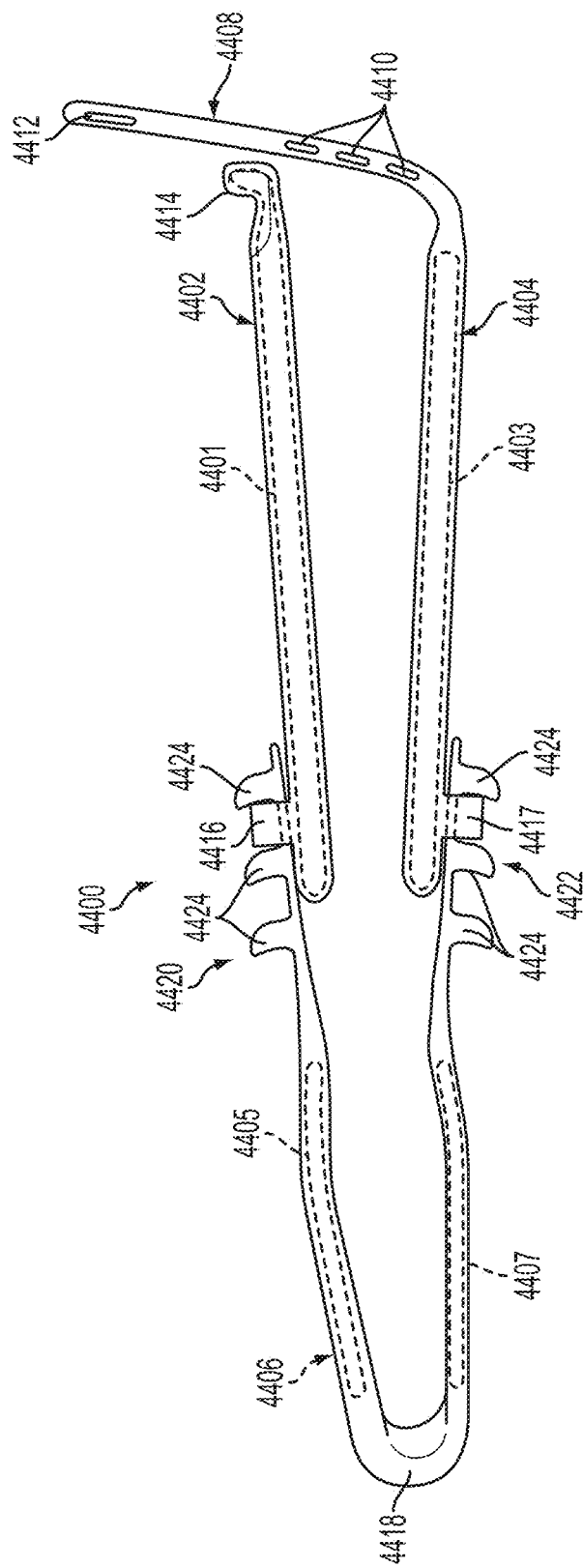

FIGS. 44(*a*) and 44(*b*) illustrate yet another embodiment of a bariatric clamp 4400 having an adjustable length. The bariatric clamp 4400 varies from the bariatric clamps discussed above with respect to FIGS. 41(*a*)-41(*e*), 42(*a*), 42(*b*), 43(*a*) and 43(*b*) in that the bariatric clamp 4400 in FIGS. 44(*a*) and 44(*b*) is comprised of multiple members, rather than a continuous design. However, it should be appreciated that the clamp 4400 operates in a manner similar to those discussed above.

The bariatric clamp 4400 includes a first substrate member 4401, second substrate member 4403, first bight substrate member 4405 and second bight substrate member 4407 (each shown dashed). The first substrate member 4401 is overmolded in a polymer material to form a first elongated member 4402 having an engagement portion 4414 at a distal end and a first receiving portion 4416 towards a proximal end of the first elongated member 4402. The second substrate member 4403 is overmolded in a polymer material to form a second elongated member 4404 having a fastener portion 4408 at a distal end and a second receiving portion 4417 at a proximal end of the second elongated member 4404. The first and second bight substrate members 4405 and 4407 are overmolded in a polymer material to form a bight member 4406 having a flexible hinge 4418, first retention feature 4420 and second retention feature 4422.

When the clamp 4400 is assembled, the first retention feature 4420 is received by the first receiving portion 4416 to couple the bight member 4406 to the first elongated member 4402, and the second retention feature 4422 is received by the second receiving portion 4417 to couple the bight member 4406 to the second elongated member 4404. The bight member 4406 comprises a passage-forming section disposed towards a proximal end of the clamp 4400, and the first and second elongated members 4402 and 4404 comprise a partition-forming section disposed towards a distal end of the clamp 4400.

Referring briefly to FIGS. 44(*a*), 44(*b*) and 10, when the clamp 4400 is installed within an abdominal cavity, the first and second elongated members 4402 and 4404 are engaged to partition the stomach into a small, vertical pouch 500 and excluded section 502. The bight member 4406 comprises the passage-forming section located towards the proximal end of the clamp 4400 and allows gastric juices to flow 506 from the excluded section 502 into the vertical pouch 500.

In the embodiment illustrated in FIGS. 44(*a*) and 44(*b*), the adjustable length is provided, at least in part, by the positions of the first and second retention features 4420 and 4422 with respect to the receiving portions 4416 and 4417 of the first and second elongated members, respectively. For example, FIG. 44(*a*) illustrates the adjustable bariatric clamp 4400 in a retracted position wherein the first and second retention features 4420 and 4422 are positioned so that the overall length of the clamp 4400 is decreased. FIG. 44(*b*) illustrates the adjustable bariatric clamp 4400 in an extended position wherein the first and second retention features 4420 and 4422 are positioned so that the overall length of the clamp 4400 is increased.

In some embodiments such as, for example, that illustrated in FIGS. 44(*a*) and 44(*b*), the first retention feature 4420 and the second retention feature 4422 each comprise a ratchet feature having a plurality of teeth 4424 formed from the polymer overmold material, and the receiving portions 4416 and 4417 each comprise a loop-type shape formed from the polymer overmold material. The teeth 4424 are capable of flexing to fit within the opening of the loop when the retention feature 4420/4422 is inserted into the receiving portion 4416/4417. This allows the retention feature 4420/4422 to slide through the opening of the receiving portion 4416/4417 to couple the bight member 4406 to the respective first or second elongated member 4402 or 4404. Once a tooth 4424 of the retention feature 4422/4424 has passed through the receiving portion 4416/4417, the tooth 4424 is capable of engaging the receiving portion 4416/4417 to prevent the retention feature 4422/4424 from unintentionally disengaging from the receiving portion 4416/4417. However, if a user wishes to remove at least a portion of the retention feature 4420/4422 from the receiving portion 4416/4417 (for example, to lengthen or disassemble the clamp 4400), the user may flex, or stretch, the receiving portion 4416/4417 and/or compress the tooth 4424 to withdraw the retention feature 4420/4422 from the respective receiving portion 4416/4417.

As mentioned above, the adjustable length of the clamp 4400 is provided, at least in part, by the positions of the first and second retention features 4420 and 4422 with respect to the receiving portions 4416 and 4417 of the first and second elongated members, respectively. To decrease the length of the clamp 4400, the user may insert the first and/or second retention features 4420 and 4422 into the respective receiving portions 4416 and 4417 as discussed above. If a user wishes to further decrease the length of the clamp 4400, the user can further insert the first and/or second retention features 4420 and 4422 into the respective receiving portions 4416 and 4417 so that additional teeth 4424 have passed through the receiving portions 4416 and 4417. For example, FIG. 44(*a*) shows the clamp 4400 in its most retracted, or shortest, position. In this embodiment, all teeth 4424 of the first and second retention features 4420 and 4422 have passed through their respective receiving portions 4416 and 4417. To increase the length of the clamp 4400, the user may remove a portion of the first and/or second retention features 4420 and 4422 from their respective receiving portions 4416 and 4417 as discussed above. If the user wishes to further increase the length of the clamp 4400, the user can further remove a portion of the first and/or second retention features 4420 and 4422 from the respective receiving portions 4416 and 4417 so that additional teeth 4424 have passed back through the receiving portions 4416 and 4417. For example, FIG. 44(*b*) illustrates the clamp 4400 in its most extended, or longest, assembled position. In this embodiment, all teeth 4424 have been withdrawn from the receiving portions 4416 and 4417 except for the last tooth 4424 of each retention feature 4420 and 4422 that maintains the coupling between the bight member 4406 and the first and second elongated members 4402 and 4404.

As shown in FIGS. 44(*a*) and 44(*b*), the first and second elongated members 4402 and 4404 are coupled to the bight member 4406 towards the proximal end of the clamp 4400. As discussed above, the bight member 4406 includes the first and second bight substrate members 4405 and 4407, the first and second retention features 4420 and 4422, and a flexible hinge 4418 formed, in one implementation, from the polymer overmold. The first and second bight substrate members 4405 and 4407 are similar (in both functionality and composition) to the first and second substrate members 4401 and 4403(and other bight substrate members disclosed herein), and may be formed of various biocompatible materials such as titanium or biocompatible polymer resins such as polyether ketone ketone (PEKK) or polyether ether ketone (PEEK). The flexible hinge 4418 allows the assembled clamp 4400 to be positioned in a variety of positions ranging from a substantially closed position (similar to that illustrated in FIGS. 41(*b*) and 41(*c*)), to a substantially expanded (or fully opened) position (similar to that shown in FIG. 41(*e*)). When the clamp 4400 is installed, the first and second bight substrate members 4405 and 4407 provide structural support to the passage-forming section of the clamp 4400. Additionally, the flexible hinge 4418 permits expansion and movement of the bight member 4406 to accommodate any irregularities in the stomach wall or fluctuations of the passage-forming section. The flexible hinge 4418 also allows the clamp 4400 to accommodate variations in stomach thicknesses without compromising the pressure applied by the clamp 4400, particularly in the partition-forming section. In some embodiments, the flexible hinge 4418 may be provided at a desired durometer or elasticity that may be the same as or different from that of the polymer or silicone overmolded portions provided in other areas of the clamp 4400, such as the first and second elongated members 4402 and 4404.

When installing the assembled bariatric clamp 4400, the clamp 4400 is placed into position as explained in greater detail below, and the fastener portion 4408 and engagement portion 4414 are used to retain the clamp 4400 in a substantially closed position. In the embodiment illustrated in FIGS. 44(*a*) and 44(*b*), the fastener portion 4408 comprises a strap formed from the overmolded polymer, or other material, and located towards the distal end of the second elongated member 4404. The strap may include one or more primary openings 4410 for receiving the engagement portion 4414, and a secondary opening 4412 used for adjusting or manipulating the fastener portion 4408, the second elongated member 4404 and/or the clamp 4400. For example, a surgeon may use a tool (not shown) to engage the secondary opening 4412 to position the strap such that the engagement portion 4414 engages one of the primary openings 4410. In the embodiment illustrated in FIGS. 44(*a*) and 44(*b*), the engagement portion 4414 comprises a protrusion, such as a hook or tab, for engaging openings of the fastener portion 4408.

In some embodiments, the assembled clamp 4400 may be adjusted by disengaging the engagement portion 4414 from one of the primary openings 4410, and engaging the engagement portion 4414 with another one of the primary openings 4410 to either increase or decrease the spacing between the first and second elongated members 4402 and 4404. In some embodiments, this adjustment of the clamp 4400 may also include adjusting the length of the clamp 4400 in accordance with the foregoing description. In some embodiments, the fastener portion 4408 may be secured to the first elongated member 4402 by suturing the fastener portion 4408 to the polymer overmolding of the first elongated member 4402.

Figure 45:
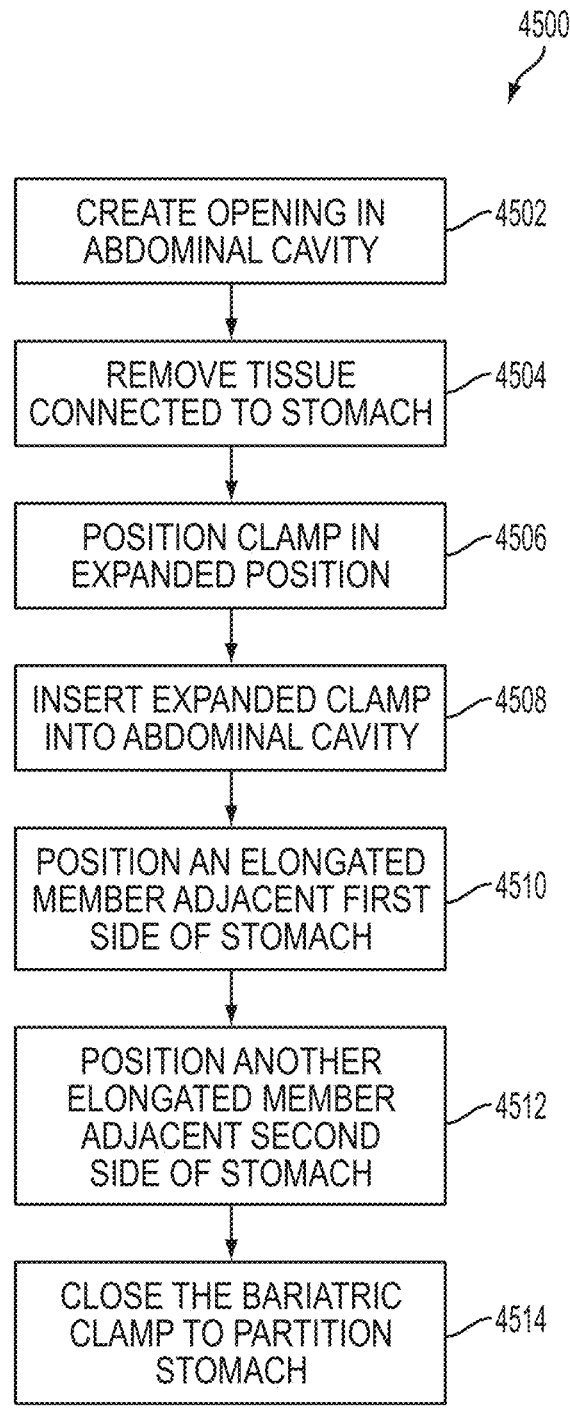
FIG. 45 is a flow diagram illustrating a method of installing a bariatric clamp.

FIG. 45 illustrates a flow diagram 4500 illustrating a method for installing a bariatric clamp. For the sake of clarity, the method illustrated in FIG. 45 is generally discussed with reference to the bariatric clamp 4100 illustrated in FIGS. 41(*a*)-41(*e*) and described above, unless otherwise specified. However, it should be appreciated that the disclosed method for installing a bariatric clamp may be applicable to various embodiments of a bariatric clamp including, but not limited to, any of the embodiments discussed above with respect to FIGS. 41-44. Additionally, when describing the method presented in FIG. 45 (and the method presented in FIG. 47), it should be understood that references to the "first elongated portion" and "second elongated portion" are not limited to the exact embodiments of a "first elongated portion" and "second elongated portion" as illustrated in any of the figures described above. For example, as used in the context of the methods discussed with reference to FIGS. 45 and 47, the "first elongated portion" of FIG. 41 may refer to a first half of the bariatric clamp 4100 including the first elongated portion 4102, the engagement portion 4114, and the section of the bight portion 4106 located on the same side of the bariatric clamp 4100. Similarly, the "second elongated portion" may refer to a second half of the bariatric clamp 4100 including the second elongated portion 4104, the fastener portion 4108, and the section of the bight portion 4106 located on the same side of the bariatric clamp 4100. It should also be noted that, in some embodiments, the first elongated portion may include the fastener portion, whereas the second elongated portion includes the engagement portion.

The method of FIG. 45 first discloses, at block 4502, creating an opening in the abdominal cavity of a patient to allow access to the patient's stomach. In some embodiments, this may include inserting one or more trocars into the patient's abdomen, wherein the trocars provide an opening through which a surgeon may insert various devices and equipment such as, for example, surgical tools, a camera and the bariatric clamp 4100. The trocars may comprise various features known in the art. For example, one or more of the trocars may, in some embodiments, include a cutting portion to assist the surgeon (or other personnel) with penetrating the abdominal cavity (or other tissue) of the patient. In some embodiments, other tools (e.g., scissors, needles, dilators, etc.) may be used to create the opening in the abdominal cavity so that the trocar can be inserted into the abdominal cavity. In some embodiments, the abdominal cavity may be inflated by forcing air (e.g., CO2) into the abdominal cavity. In such embodiments, a hose or tube may be inserted into or connected to one or more of the trocars, and the trocars may include a seal to prevent the air from escaping the abdominal cavity through the trocars. In some embodiments, a camera or endoscope may be placed into the abdominal cavity to allow a surgeon or other personnel to view installation, removal or adjustment of the bariatric clamp 4100. In such embodiments, the endoscope may be placed into the abdominal cavity through a trocar inserted, for example, at the navel of the patient.

At block 4504, the method discloses removing tissue connected to the stomach, particularly at locations where the bariatric clamp 4100 is to be positioned adjacent the stomach. Tissue attached to or adhered to the exterior surface of the stomach is removed to create a tunnel, path or passageway on the exterior surface of the stomach for the first and second elongated portions 4102 and 4104 of the bariatric clamp 4100 to reside on the stomach, such as in a vertical orientation, or primarily vertical orientation, on the anterior and posterior sides of the exterior surfaces of the stomach, to partition the stomach, as described herein, and while providing a passage-forming section to allow some flow or exchange of gastric fluids between the first and second regions. When the bariatric clamp 4100 is in a closed position, some gastric juices are believed likely to be exchanged across both the first and second regions, and primarily through the passage forming section of the bariatric clamp 4100.

In some embodiments, the removal of the tissue may be accomplished by resecting the tissue using surgical equipment such as, for example, clamps, forceps, vacuum hoses, scalpels, an ultrasonic probe, or any combination thereof to create a passageway, tunnel or path for the bariatric clamp 4100 or any other surgical tools (e.g., alignment device, guide member, etc.) used in the installation process. Additionally, this step may include displacing tissue and/or organs (e.g., the liver) located towards a top, bottom, anterior and/or posterior side of the stomach to expose the stomach to provide easier access to the stomach. This may also include exposing one or more locations where the bariatric clamp 4100, or other surgical equipment or tools, can be positioned onto the stomach with little or no intervening tissue.

Figure 46:
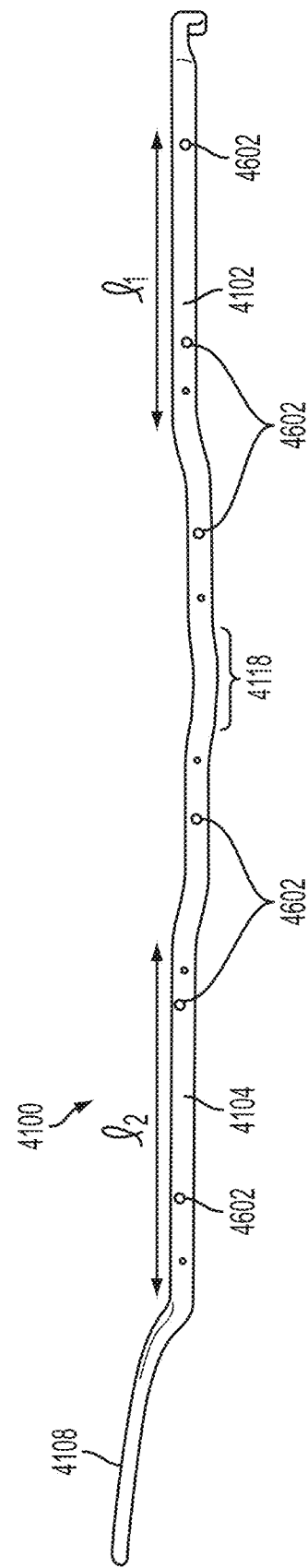
FIG. 46 illustrates the bariatric clamp of FIGS. 41(a)-41(e) in a substantially expanded position.

At block 4506, the method discloses positioning the bariatric clamp 4100 in a substantially expanded or opened position. Referring briefly to FIGS. 46 and 50(*a*)-50 (*d*), the bariatric clamp 4100 of FIGS. 41(*a*)-41(*e*) is illustrated in various opened positions (FIG. 41(*e*) also illustrates the bariatric clamp 4100 in a substantially expanded or opened position). As shown in FIG. 46, the clamp 4100 is placed in an opened position such that the bariatric clamp 4100 is capable of fitting into the opening of the abdominal cavity of the patent in the opened position wherein the first and second elongated portions 4102 and 4104 separately pass through the opening in the abdominal cavity. In some embodiments, this may include fitting the opened bariatric clamp 4100 through a trocar (e.g., a 12 mm trocar) while the bariatric clamp 4100 is in an opened or substantially expanded position. It should be appreciated that the fastener portion 4108 is comprised of the polymer overmolding, and is therefore capable of flexing, as shown in FIG. 46, to fit within the opening of the abdominal cavity. Similarly, the flexible hinge 4118 is also comprised of the polymer overmolding, and is also capable of flexing to allow the first and second elongated portions to contort or adjust while the bariatric clamp 4100 is inserted into the opening of the abdominal cavity. In some embodiments, positioning the bariatric clamp 4100 in the expanded position may include aligning the first and second elongated portions such that a length $l_1$ of the first elongated portion 4102 is substantially collinear with a length $l_2$ of the second elongated portion 4104. In some embodiments, positioning the clamp in the expanded position may include assembling the clamp, for example, if the embodiment of the clamp 4400 provided in FIGS. 44(*a*) and 44(*b*) is implemented. However, in alternate embodiments, the clamp 4400 in FIGS. 44(*a*) and 44(*b*) may be assembled after being inserted into the abdominal cavity.

Figure 47:
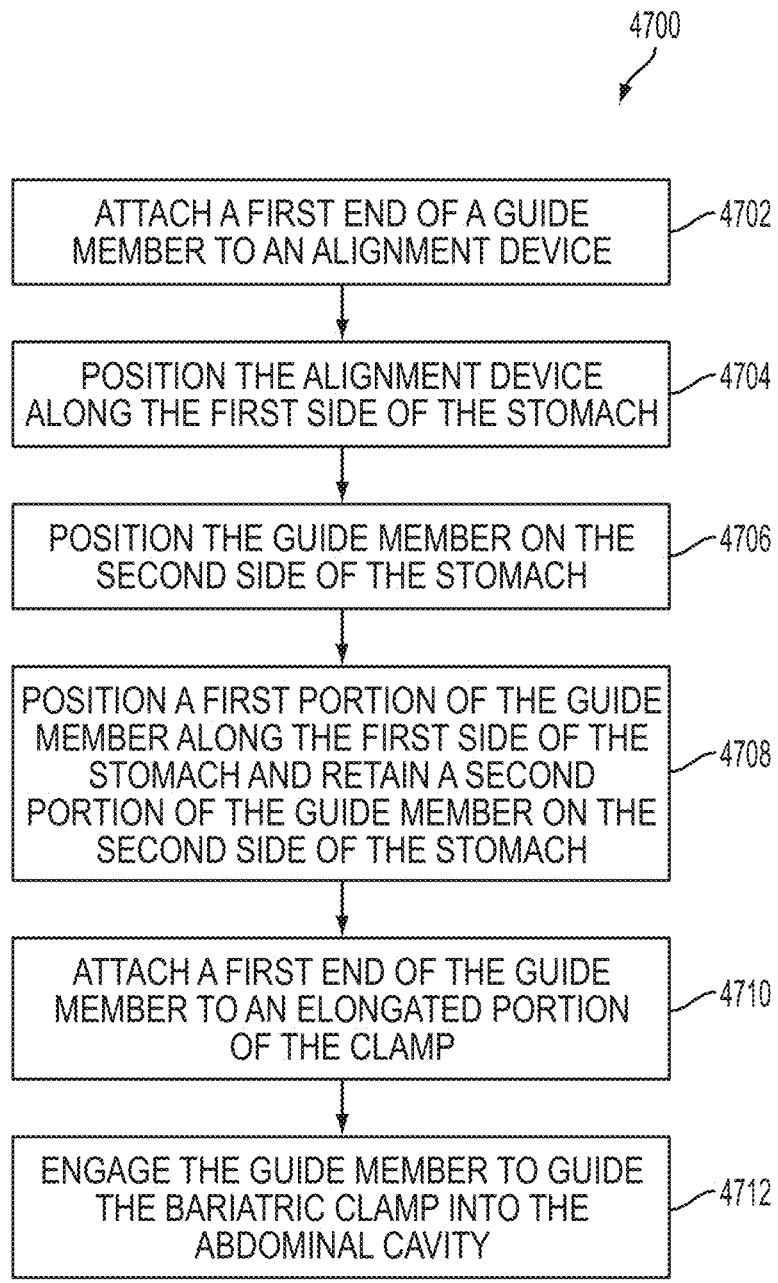
FIG. 47 is a flow diagram illustrating a method of inserting a bariatric clamp into the abdominal cavity of the patient.

At block 4508 of FIG. 45, the bariatric clamp 4100 is inserted into the abdominal cavity in the substantially expanded or opened position discussed herein. FIG. 47 provides a flow diagram 4700 illustrating one embodiment of a method for inserting the bariatric clamp 4100 into the abdominal cavity in the opened position. The method illustrated in FIG. 47 implements an alignment device (e.g., Gold finger, clamp, forceps, etc.) to position a guide member (e.g., suture, string, thread, twine, wire, etc.), wherein the guide member is used to guide the bariatric clamp 4100 as it is inserted into the abdominal cavity and/or positioned adjacent the stomach. While describing the method of FIG. 47, reference is made to FIGS. 48(*a*) and 48(*b*), which illustrate various views of the patient's stomach 4800. FIG. 48(*a*) illustrates an overview perspective of a first side 4810, top 4815 and bottom 4817 of the patient's stomach 4800. FIG. 48(*b*) illustrates a profile view of the stomach 4800 as viewed along line A-A in FIG. 48(*a*). The profile view shows the first side 4810, top 4815 and bottom 4817 of the stomach 4800 and a second side 4820 of the stomach 4800. In some embodiments, the first side 4810 may be the posterior side of the stomach and the second side 4820 may be the anterior side of the stomach, however in other embodiments, the first side 4810 may be the anterior side of the stomach and the second side 4820 may be the posterior side of the stomach.

Referring briefly to FIGS. 49(*a*) and 49(*b*), an example embodiment of an alignment device, or tool 4900 is shown having an end member 4910 disposed at a distal end of the tool 4900, and a handle 4920 disposed at a proximal end of the tool 4900. The end member 4910 is disposed at the end of a shaft portion 4915 of the tool 4900 and, in some embodiments, includes an opening 4912 for receiving and/or retaining a guide member (e.g., suture). As explained in greater detail below, the tool 4900 may be used to assist with positioning the guide member through a tunnel or path created along a side of the stomach and around the top of the stomach. In some embodiments, the end member 4910 may be articulated in an upward direction with reference to the horizontal shaft portion 4915 as shown in FIG. 49(*a*), and may also be articulated to be positioned in-line with the shaft portion 4915 as shown in FIG. 49(*b*). Articulation of the end member 4910 may be controlled by actuating the handle 4920 as shown in FIGS. 49(*a*) and 49(*b*).

In the method of FIG. 47, the alignment device is used to position the guide member so that it may be used to guide the bariatric clamp 4100 into the abdominal cavity, and into position as further described below. At block 4702, a first end of the guide member is attached to a distal end of the alignment device (or the first end of the guide member is grasped using the distal end of the alignment device), and the alignment device is inserted into the abdominal cavity (e.g., through a trocar). At block 4704, the alignment device is positioned along the first side 4810 of the stomach 4800 by traversing the distal end of the alignment device along the first side 4810 of the stomach towards the top 4815 of the stomach 4800. Once positioned at the top 4815 of the stomach 4800 (e.g., at location 4805), the distal end of the alignment device (e.g., the end member 4910 of tool 4900) is positioned (e.g., articulated, extended, etc.) so that a portion of the guide member is accessible from the second side 4820 of the stomach 4800, while the a portion of the alignment device (e.g., the shaft portion 4915 of tool 4900) remains positioned along the first side 4810 of the stomach 4800. At block 4706, the guide member is then positioned on the second side 4820 of the stomach 4800 (for example, using a clamp or forceps), while the first end of the guide member remains attached to the distal end of the alignment device (e.g., the end member 4910 of tool 4900).

Figure 48A:
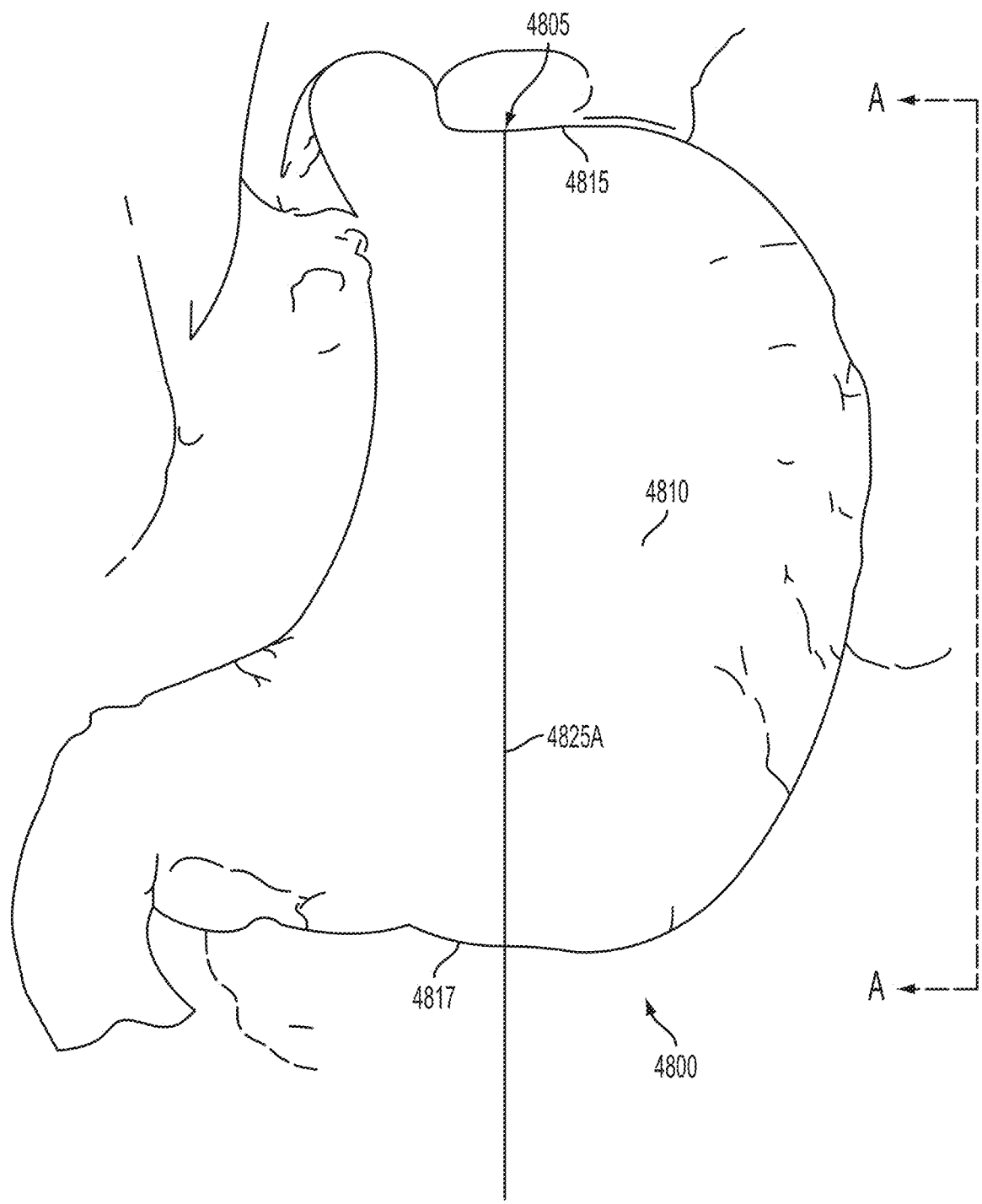
FIGS. 48(a) and 48(b) illustrate various views of a patient's stomach.
Figure 48B:
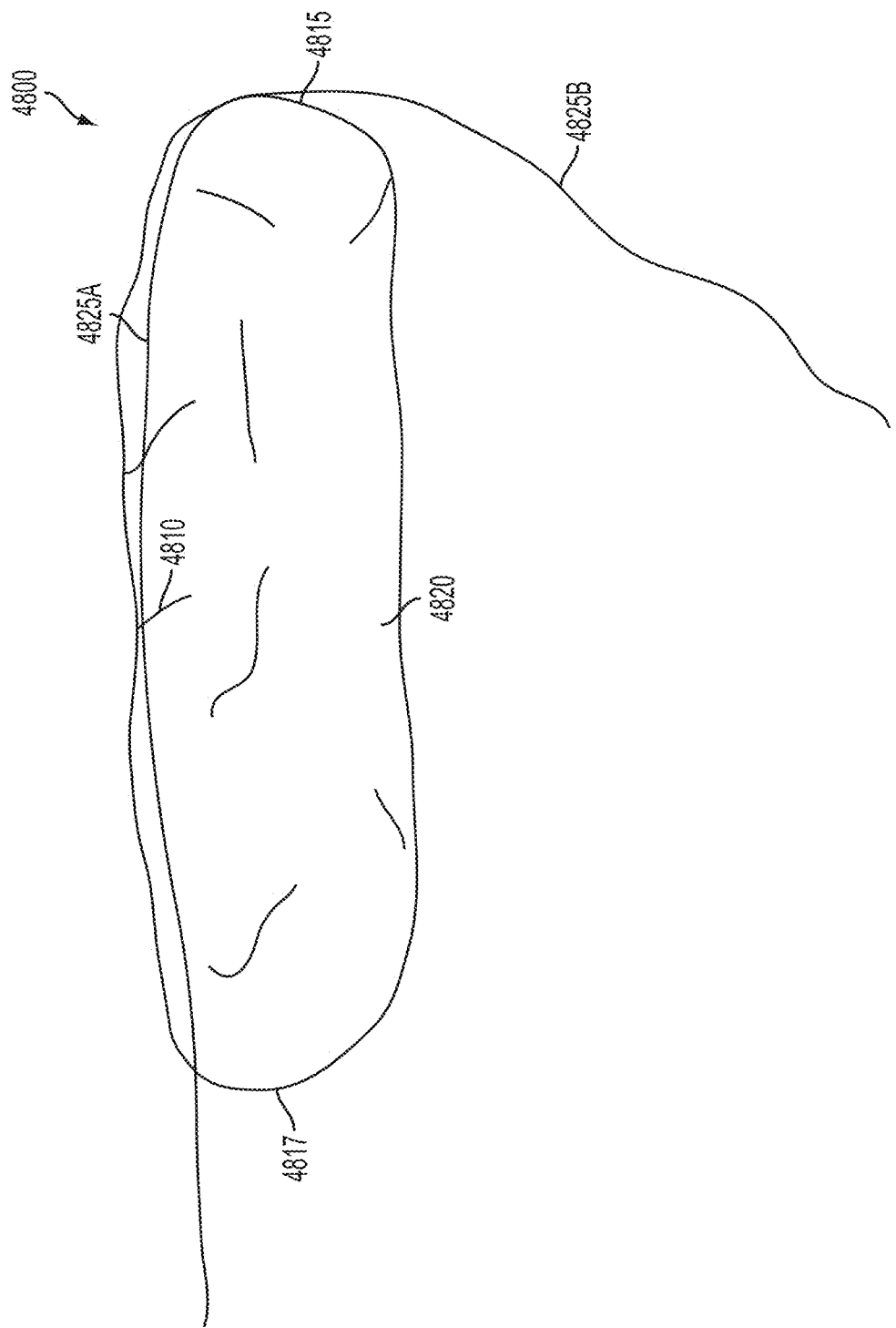

At block 4708, the alignment device is withdrawn from the first side 4810 of the stomach 4800 (and preferably withdrawn from the abdominal cavity) by traversing the first side 4810 of the stomach in a direction towards the bottom 4817 of the stomach 4800 such that a first portion 4825A of the guide member is positioned or aligned along the first side 4810 of the stomach 4800, while a second portion 4825B of the guide member is retained (for example, using a clamp or forceps) on the second side 4820 of the stomach 4800. FIGS. 48(a) and 48(b) illustrate the first portion of the guide member 4825A and the second portion of the guide member 4825B, in accordance with the present embodiment. In this embodiment, the first portion of the guide member is aligned such that the position of the first portion of the guide member is relatively consistent with the location at which an elongated portion 4102/4104 of the clamp 4100 will be positioned adjacent the first side 4810 of the stomach 4800.

At block 4710, the first end of the guide member is then disconnected from the alignment device and attached to one of the first or second elongated portions 4102 or 4104 of the bariatric clamp 4100. In some embodiments, this may be accomplished by attaching the guide member through the secondary opening 4112 and/or around the fastener portion 4108 of the second elongated portion 4104 of the clamp 4100. In other embodiments, this may be accomplished by attaching the guide member to the engagement portion 4114 of the first elongated portion 4102. At block 4712, with the first end of the guide member attached to either the first elongated portion 4102 or the second elongated portion 4104, and the clamp 4100 positioned in the substantially expanded position, the second portion of the guide member 4825B is engaged to guide the bariatric clamp 4100 into the abdominal cavity. In some embodiments, this may be accomplished by pulling on the second portion of the guide member with surgical tools (e.g., forceps, clamps, etc.) to extract the first portion of the guide member 4825A from the first side 4810 of the stomach 4800 while feeding the bariatric clamp 4100 into a trocar while the clamp 4100 remains in the substantially expanded position.

Referring again to FIG. 45, the first or second elongated portion 4102/4104 of the clamp 4100 attached to the guide member at block 4710 is then positioned adjacent the first side 4810 of the stomach 4800 at block 4510, while the clamp 4100 remains in an opened position. In some embodiments, this may be accomplished by continuing to engage the second portion of the guide member 4825B until the respective first or second elongated portion 4102 or 4104 is positioned adjacent the first side 4810 of the stomach. At this time, the guide member may be disconnected from the first or second elongated portion 4102 or 4104 and removed from the abdominal cavity. Additionally, other surgical tools (e.g., clamps, forceps, scissors, etc.) may be used to position the first or second elongated portion 4102 or 4104 adjacent the first side 4810 of the stomach 4800. The remaining elongated portion is then positioned adjacent the second side 4820 of the stomach 4800 at block 4512. The clamp 4100 should be positioned so that the bight portion 4106 of the clamp 4100 is abutting the bottom 4817 of the stomach 4800. In some embodiments, surgical tools may be used to engage the remaining elongated portion and to properly position the elongated portion adjacent the second side 4820 of the stomach 4800. Although the method is described in accordance with a preferred embodiment, it should be understood that, in some embodiments, the clamp 4100 may be installed in an sequence wherein blocks 4510 and 4512 are performed in reversed order.

At block 4514, the bariatric clamp 4100 is closed to partition the stomach in accordance with the disclosure provided above with respect to the various embodiments of the bariatric (or surgical) clamps. In some embodiments, this may include stretching the tissue of the stomach along the length of the clamp 4100 to eliminate folds in the stomach tissue. In some embodiments, closing the clamp 4100 may also include securing the clamp 4100 in the closed position. For example, closing and securing the bariatric clamp 4100 of FIG. 41(a) may include using a tool to engage the fastener portion 4108 (for example, at the secondary opening 4112) to position the fastener portion 4108 such that the engagement portion 4114 engages one of the primary openings 4110.

In some embodiments, closing the bariatric clamp 4100 may also include affixing the first elongated portion 4102 to the side of the stomach adjacent the first elongated portion 4102, and/or affixing the second elongated portion 4104 to the side of the stomach adjacent the second elongated portion 4104 to prevent unwanted migration or displacement of portions of the clamp 4100. In some embodiments, this may be accomplished by suturing the first and second elongated portions 4102 and 4104 to their respective sides of the stomach. For example, the first elongated portion 4102 may be sutured to the first side of the stomach (assuming the clamp 4100 is installed such that the first side of the stomach is adjacent the first elongated portion 4102) by suturing through the overmolded portion of the first elongated portion 4102. Similarly, the second elongated portion 4104 may be sutured to the second side of the stomach (assuming the clamp 4100 is installed such that the second side of the stomach is adjacent the second elongated portion 4104) by suturing through the overmolded portion of the second elongated portion 4104.

Figure 55:
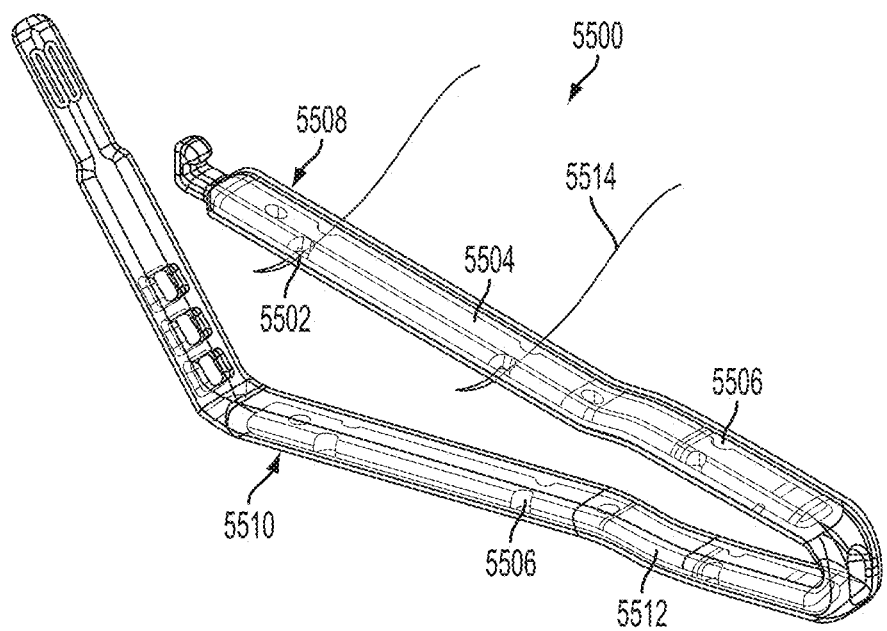
FIG. 55 illustrates an embodiment of the disclosed clamp having suturing needles embedded in the polymer overmolding.

An example of one such embodiment is illustrated in FIG. 55, which illustrates a clamp 5500, similar to the clamp 4100 discussed herein, having curved suturing needles 5502 embedded or encapsulated within the polymer overmolding of the bariatric clamp 5500 and used to anchor the first elongated portion 5508 and/or second elongated portion 5510 to the stomach once the clamp 5500 is properly installed and positioned. In some embodiments, the substrate members (e.g., first substrate member 5504) may be modified to accommodate the placement of the suturing needles 5502. For example, as shown in FIG. 55, the first substrate member 5504 and second substrate member 5512 include various recesses 5506 to accommodate placement of the suturing needles. In some embodiments, a clamp modified such as that shown in FIG. 55 may be inserted into the abdominal cavity of the patient having the curved suturing needles 5502 embedded or encapsulated within the polymer overmolding of the bariatric clamp and having sutures 5514 coupled to the curved suturing needles 5502. In such an embodiment, once the first and/or second elongated portions 5508 and/or 5510 are properly positioned, pressure may be applied to the needles 5502 or elongated portion of the clamp such that the needles 5502 protrude from the polymer overmolding and into the adjacent walls of the stomach to suture the respective first and/or second elongated portions 5508 and/or 5510 to the stomach. In some embodiments, the suture needles 5502 may be manipulated using the suture(s) 5514 attached to the respective needle 5502. In some embodiments, instead of applying pressure to the needles 5502 as discussed above, the needles 5502 may be extracted from the polymer overmolding by manipulating the needles 5502 with the attached suture(s) 5514. Referring briefly to FIG. 46, the clamp may, in some embodiments, include one or more visual indicators 4602 for defining locations where sutures may be applied to or embedded within the clamp.

In some embodiments, the bariatric clamp may be attached to and positioned on the exterior surface of the patient's stomach using one or more toggle suture assemblies that are either partially or fully positioned from the exterior of the stomach to the stomach wall or from the exterior wall of the stomach to the interior of the stomach, depending on a desired implementation of a toggle suture. For example, the embodiment of the clamp 5500 illustrated in FIG. 55 may be modified such that the curved needles 5502 in FIG. 55 are replaced by a toggle suture or toggle suture assembly (such as a toggle suture assembly known in the art). In some embodiments, one or more toggle suture assemblies may be temporarily inserted into the clamp 5500 at various locations (e.g., at the recesses 5506) or, in other embodiments, may be lock molded, machined, or installed at desired locations on the bariatric clamp to assist with installation of the clamp on the patient's stomach. In some embodiments, the toggle suture assemblies can be retroactively installed in a pre-manufactured clamp 5500. In one embodiment, various toggle suture assemblies are provided adjacent the first and second ends of the bariatric clamp, such as adjacent the flexible hinge and/or the connection point where the bariatric clamp is closed, and along the first and second elongated members and the bight portion, as desired.

It should be appreciated that the bariatric clamp and/or sutures may be implemented using known or available absorbable materials, such as bio-absorbable materials (e.g., catgut suture), that provide desirable or suitable mechanical or structural properties and integrity for a desired or needed period of time prior to being absorbed or disintegrating to an unacceptable level. Either natural or synthetically absorbable materials may be used. Poly glycol, for example, may be used in certain implementations.

In some embodiments, the method illustrated in FIG. 45 may further include adjusting a length of the bariatric clamp as discussed above with respect to the clamps illustrated in FIGS. 42(*a*), 42(*b*), 43(*a*), 43(*b*), 44(*a*) and 44(*b*). Depending upon the particular embodiment of the clamp, the length of the bariatric clamp may be adjusted in a variety of ways. For example, in the embodiments discussed above with respect to FIGS. 42(*a*), 42(*b*), 43(*a*) and 43(*b*), the length of the clamp may be adjusted by adjusting the length of the first elongated portion and/or the second elongated portion. In the embodiments discussed above with respect to FIGS. 44(*a*) and 44(*b*), the length of the clamp may be adjusted by adjusting the positions of the first and second retention features with respect to the receiving portions of the first and second elongated members. Regardless of which clamp is used, the length may be adjusted at any point during the clamp installation. However, it is preferable to adjust the length of the clamp prior to securing the clamp to the patient's stomach. Nevertheless, the clamp may also be uninstalled by reversing any of the steps discussed above (e.g., by removing sutures affixing any portions of the clamp to the stomach), so that the clamp may be removed or adjusted, wherein such adjustments may include adjusting the length of the clamp as discussed herein, or adjusting a position of the clamp on the stomach.

In some embodiments, the method for installing a bariatric clamp may further include ensuring proper installation of the bariatric clamp 4100. This may include measuring a pressure applied on the stomach by the clamp 4100. In some embodiments, the pressure may be measured by placing one or more pressure transducers between the clamp 4100 and one of the sides of the stomach. In some embodiments, a pressure in the range of 0-2 or 0-3 inHg may be desired. Additionally, ensuring proper installation may, in some embodiments, include inserting a radiopaque fluid such as, for example, Barium into the stomach and observing the fluid, for example, via x-ray imaging to determine proper flow between the various regions of the stomach.

Once installation of the clamp is complete, the surgical equipment may be removed, and the internal organs repositioned in their natural positions. Other precautions may be taken including, for example, cleaning or cauterizing any bleeding tissue to prevent clotting.

A number of additional and alternative embodiments of the surgical clamps, installation tools and methods for installing can have characteristics that are different from those described above. For example, it is envisioned that a surgical clamp not intended for bariatric surgery might not have a passage forming section, and that such a clamp might be smaller or larger, depending on the purpose of the clamp. For example, the clamp can be one-tenth of an inch in length to partition a blood vessel, or twenty-two centimeters in length to partition a stomach. Moreover, the clamp can be configured to partition any internal organ, and can vary in length accordingly between these two example lengths, or be longer or shorter as required. Also, the guide members might have one or more protrusions aligned with the engagement feature and configured for insertion into the slot formed in the bight portion of the clamp. Moreover, it is envisioned that the installation tool can be integrated with an endoscope and/or surgical robot, and that appropriate robotic elements can be included in place of or in addition to those described above. These and other features can be included in various combinations without departing from the scope of the invention as defined in the following claims.

What is claimed is:

1. A bariatric clamp comprising a partition-forming section and a passage-forming section, the bariatric clamp configured to be positioned in an open position and in a first closed position and a second closed position, wherein the partition-forming section comprises a first elongated member and a second elongated member separated by at least a first distance; and wherein the passage-forming section comprises a bight portion, the bight portion comprising:

a first bend section at a distal end of the first elongated member and comprising a first member extending in a first direction at least partially away from a longitudinal axis of the bariatric clamp;

a second bend section at a distal end of the second elongated member and comprising a second member extending in a second direction at least partially away from the longitudinal axis of the bariatric clamp;

a third member extending away from the first bend section that extends in the first direction at least partially away from the longitudinal axis of the bariatric clamp, and a fourth member extending away from the second bend section that extends in the second direction at least partially away from the longitudinal axis of the bariatric clamp, the third member and the fourth member separated by at least a second distance;

an engagement portion disposed adjacent the first elongated member;

a fastener portion disposed adjacent the second elongated member, wherein the fastener portion includes two or more openings operable to receive at least a portion of the engagement portion to selectably retain the bariatric clamp in the first closed position and in the second closed position; and a flexible hinge joining the third and fourth members, the flexible hinge elastically stretchable in a direction perpendicular to the longitudinal axis of the bariatric clamp, wherein, when the bariatric clamp is in the first closed position, the second distance is greater than the first distance, and the first distance may be adjusted by disengaging the engagement portion from the fastener portion, and reengaging the engagement portion with the fastener portion to retain the bariatric clamp in the second closed position that is different from the first closed position.

2. The bariatric clamp of claim 1, further comprising: an aperture at least partially defined by the passage-forming section and at least a portion of the partition-forming section, the aperture having at least one dimension that is greater at the passage-forming section than at the partition-forming section.

3. The bariatric clamp of claim 2, wherein the aperture is larger in a first dimension than in a second dimension, the second dimension orthogonal to the first dimension.

4. The bariatric clamp of claim 1, wherein the first elongated member has a first thickness between an inner surface and an outer surface of the first elongated member, and wherein the second elongated member has a second thickness between an inner surface and an outer surface of the second elongated member.

5. The bariatric clamp of claim 1, wherein the engagement portion is integrated with the first elongated member.

6. The bariatric clamp of claim 1, wherein the engagement portion includes a hook feature disposed towards the proximal end of the first elongated member.

7. A bariatric clamp having a central longitudinal axis extending from a proximal end to an opposite distal end of the bariatric clamp, the bariatric clamp comprising:

a first elongated member;

a first bent portion connected to a distal end of the first elongated member;

a second elongated member connected to the first bent portion, a third elongated member;

a second bent portion connected to a distal end of the third elongated member;

a fourth elongated member connected to the second bent portion;

wherein the second elongated member and the fourth elongated member include a polymer overmold; and a bight member connecting the second elongated member to the fourth elongated member, wherein the polymer overmold extends through the bight member from the second elongated member to the fourth elongated member, the bight member elastically stretchable in a direction that is perpendicular to the central longitudinal axis of the bariatric clamp when the bariatric clamp is in a closed position.

8. The bariatric clamp of claim 7, wherein the bight member comprises a hinge flexible in at least two degrees of freedom.

9. The bariatric clamp of claim 7, wherein the bight member comprises a hinge flexible in at least three degrees of freedom.

10. A bariatric clamp having a longitudinal axis between a proximal end and a distal end, the bariatric clamp comprising:

a first elongated portion having a first substrate member at least partially overlaid by a first polymer portion;

a second elongated portion having a second substrate member at least partially overlaid by a second polymer portion; and a bight portion comprising a third polymer portion joining the first and second polymer portions of the first and second elongated portions respectively, the bight portion elastically stretchable in a direction substantially perpendicular to the longitudinal axis of the bariatric clamp when the bariatric clamp is in a closed position, wherein the first polymer portion, the second polymer portion, and the third polymer portion together form a single polymer portion.

11. The bariatric clamp of claim 10, further comprising a coupling disposed towards a distal end of the first and second elongated portions, and the coupling configured to couple the distal end of the first elongated portion with the distal end of the second elongated portion.

12. The bariatric clamp of claim 10, further comprising a fastener portion disposed adjacent the first elongated portion, and an engagement portion disposed adjacent the second elongated portion, the fastener portion comprising one or more openings operable to receive at least a portion of the engagement portion.

* * * * *